(12) United States Patent
Kawada et al.

US011607667B2

(10) Patent No.: US 11,607,667 B2
(45) Date of Patent: Mar. 21, 2023

(54) ABSORPTION AGENT AND ABSORBENT ARTICLE

(71) Applicant: NIPPON SHOKUBAI CO., LTD., Osaka (JP)

(72) Inventors: Hiroki Kawada, Hyogo (JP); Taku Iwamura, Hyogo (JP); Koji Tachi, Hyogo (JP); Makiko Masuda, Hyogo (JP); Yasuhisa Nakashima, Hyogo (JP); Kazushi Torii, Hyogo (JP); Yukihiro Kasano, Hyogo (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 381 days.

(21) Appl. No.: 16/762,994

(22) PCT Filed: Nov. 14, 2018

(86) PCT No.: PCT/JP2018/042172
§ 371 (c)(1),
(2) Date: May 11, 2020

(87) PCT Pub. No.: WO2019/098244
PCT Pub. Date: May 23, 2019

(65) Prior Publication Data
US 2020/0398253 A1   Dec. 24, 2020

(30) Foreign Application Priority Data

Nov. 16, 2017  (JP) .............................. JP2017-220864
May 31, 2018  (JP) .............................. JP2018-105508

(51) Int. Cl.
| B01J 20/26 | (2006.01) |
| A61F 13/53 | (2006.01) |
| B01J 20/04 | (2006.01) |
| B01J 20/28 | (2006.01) |
| C08F 220/06 | (2006.01) |
| A61F 13/15 | (2006.01) |
| B65G 31/04 | (2006.01) |
| B65G 65/48 | (2006.01) |

(52) U.S. Cl.
CPC ............ *B01J 20/267* (2013.01); *A61F 13/53* (2013.01); *B01J 20/043* (2013.01); *B01J 20/28016* (2013.01); *C08F 220/06* (2013.01); *A61F 2013/15463* (2013.01); *A61F 2013/530591* (2013.01); *A61F 2013/530686* (2013.01); *A61F 2013/530693* (2013.01); *A61F 2013/530751* (2013.01); *B65G 31/04* (2013.01); *B65G 65/48* (2013.01); *C08F 2800/20* (2013.01); *C08F 2810/20* (2013.01)

(58) Field of Classification Search
CPC ........ B01J 20/26; B01J 20/267; B01J 20/043; B01J 20/28016; A61F 13/53; A61F 2013/15463; A61F 2013/530591; A61F 2013/530686; A61F 2013/530693; A61F 2013/530751; C08F 220/06; C08F 2800/20; C08F 2810/20; B65G 31/04; B65G 65/48
USPC ......................................................... 252/194
See application file for complete search history.

(56) References Cited

U.S. PATENT DOCUMENTS

| 4,988,239 A | 1/1991 | Firth |
| 5,051,041 A | 9/1991 | Firth |
| 5,355,993 A | 10/1994 | Hay |
| 5,381,886 A | 1/1995 | Hay |
| 5,402,876 A | 4/1995 | Hay |
| 5,485,909 A | 1/1996 | Hay |
| 2003/0190198 A1 | 10/2003 | Baer et al. |
| 2004/0028485 A1 | 2/2004 | Baer et al. |
| 2005/0118423 A1 | 6/2005 | Adachi et al. |
| 2005/0209352 A1 | 9/2005 | Dairoku et al. |
| 2006/0157322 A1 | 7/2006 | Baer et al. |
| 2007/0066167 A1 | 3/2007 | Wada et al. |
| 2007/0084700 A1 | 4/2007 | Baer et al. |
| 2007/0141338 A1 | 6/2007 | Ishizaki et al. |
| 2008/0142340 A1 | 6/2008 | Baer et al. |
| 2010/0119312 A1 | 5/2010 | Nagashima et al. |
| 2012/0184670 A1 | 7/2012 | Kobayashi et al. |
| 2015/0129799 A1 | 5/2015 | Kobayashi et al. |

(Continued)

FOREIGN PATENT DOCUMENTS

| CN | 1934170 A | 3/2007 |
| CN | 102548654 A | 7/2012 |
| CN | 204027530 U | 12/2014 |

(Continued)

OTHER PUBLICATIONS

Office Action from corresponding Indian Application No. 202017023800 dated Sep. 8, 2021.

(Continued)

*Primary Examiner* — Edward M Johnson
(74) *Attorney, Agent, or Firm* — Harness Dickey & Pierce P.L.C.

(57) ABSTRACT

Provided is a water-absorbing agent that causes no or little fluctuation of feed rate when fed with use of a feeder. A water-absorbing agent containing a water-absorbing resin as a main component, the water-absorbing agent satisfying the following (a) and (b): (a) K-index is 70 or more; and (b) Moisture absorption blocking ratio, after 30 minutes of standing at a temperature of 25° C. and a relative humidity of 80% RH, is 70 weight % or less, the K-index being defined by the following equation: K-index=100−(−438+3.6×angle of repose+3.5×angle of difference+7.9×compressibility rate+290×bulk density (EDANA method)).

13 Claims, 6 Drawing Sheets

(56) References Cited

U.S. PATENT DOCUMENTS

2017/0014801 A1  1/2017  Ikeuchi et al.

FOREIGN PATENT DOCUMENTS

| | | |
|---|---|---|
| CN | 105771945 A | 7/2016 |
| EP | 3056268 A1 | 8/2016 |
| JP | S6065184 A | 4/1985 |
| JP | 5503492 | 6/1993 |
| JP | 2001-137704 A | 5/2001 |
| JP | 3548575 B2 | 7/2004 |
| JP | 2004-261796 A | 9/2004 |
| JP | 3659645 B2 | 6/2005 |
| JP | 2005-522391 A | 7/2005 |
| JP | 2006-528119 A | 12/2006 |
| JP | 2009-511393 A | 3/2009 |
| JP | 201132422 A | 2/2011 |
| JP | 2013-39804 A | 2/2013 |
| JP | 2014-73448 A | 4/2014 |
| JP | 6068745 B2 | 1/2017 |
| WO | 2004/096304 A1 | 11/2004 |
| WO | 2005/075070 A1 | 8/2005 |
| WO | 2006/109844 A1 | 10/2006 |
| WO | 2008/120742 A1 | 10/2008 |
| WO | 2014/162843 A1 | 10/2014 |
| WO | 2015053372 A1 | 4/2015 |
| WO | WO-2015108084 A1 | 7/2015 |
| WO | WO-2015129917 A1 | 9/2015 |
| WO | 2017/170605 A1 | 10/2017 |

OTHER PUBLICATIONS

Office Action from corresponding Chinese Application No. 201880074112.8 dated Apr. 30, 2021.
Office Action from corresponding Japanese Application No. 2019-554260 dated Dec. 14, 2021.
International Preliminary Report on Patentability for corresponding PCT Application No. PCT/JP2018/042172 dated May 19, 2020.
International Search Report for corresponding PCT Application No. PCT/JP2018/042172 dated Feb. 19, 2020.
Office Action from corresponding Japanese Application No. 2019-554260 dated Mar. 1, 2022.

ABSORPTION AGENT AND ABSORBENT ARTICLE

TECHNICAL FIELD

The present invention relates to a water-absorbing agent and an absorbent article.

BACKGROUND ART

Water-absorbing resin (Super Absorbent Polymer, or SAP) is a water-swellable, water-insoluble polymer gelling agent. Water-absorbing resin is used for various applications. For example, water-absorbing resin is used in sanitary materials such as disposable diapers, sanitary napkins, and incontinence articles for adults, agricultural and horticultural water retaining agents, industrial waterproofing agents, and the like.

When a disposable diaper (major application of SAP) is produced, a water-absorbing agent that contains a SAP (raw material) as a main component is fed. When such a feeding is carried out, generally, an apparatus to meter and convey the water-absorbing agent is used. For example, Non-patent Literature 1 (Handbook of Filters, $4^{th}$ Edition, page 281 "3.9 Feeding" George Wypych, ChemTec Publishing, Toronto, 2016 (the first edition was published in 1993)) discloses a rotary feeder, a screw feeder, a table feeder, and a belt feeder, which are examples of the above-mentioned apparatus. Non-patent Literature 1 also discloses, as an apparatus designed to accurately feed a bulk material, a bulk solid pump (BSP/Bulk Solids Pump™, also called "Bulk Solids Pump") manufactured by Coperion K-tron.

Patent Literature 1 (U.S. Pat. No. 5,051,041) and Patent Literature 2 (Published Japanese Translation of PCT International Application, Tokuhyohei, No. 5-503492) each disclose a multiple-choke apparatus to convey and meter a particulate material. Patent Literature 3 (U.S. Pat. No. 5,355,993), Patent Literature 4 (Japanese Patent No. 3548575) and Patent Literature 5 (Japanese Patent No. 3659645) each disclose an apparatus for conveying a particulate material, which can be used both for conveying and metering solid material in atmospheric conditions and against atmospheric pressure. Patent Literature 6 (Published Japanese Translation of PCT International Application, Tokuhyo, No. 2005-522391), Patent Literature 7 (Published Japanese Translation of PCT International Application, Tokuhyo, No. 2006-528119), and Patent Literature 8 (Published Japanese Translation of PCT International Application, Tokuhyo, No. 2009-511393) each disclose a feeder that includes a housing and a drive rotor that has one or more drive disks. These are examples of an apparatus using the foregoing bulk solid pump (hereinafter referred to as "BSP-type apparatus").

On the other hand, there are disclosed water-absorbing agents to be fed by various feeders. For example, Patent Literature 9 (International Publication No. WO2006/109844) discloses a water-absorbing agent that can be conveyed by a screw feeder with improved stability due to its specific moisture content, specific frictional electrification charge, and the like. For example, Patent Literature 10 (International Publication No. WO2008/120742) discloses a water-absorbing agent that can be conveyed by air in good condition and that is prevented from decreasing in the effect of a liquid permeability improving agent. This water-absorbing agent is obtained by adding an organic surface-crosslinking agent, the liquid permeability improving agent, and a lubrication improving agent in the order named to a water-absorbing resin. For example, Patent Literature 11 (International Publication No. WO2005/075070) discloses a water-absorbing agent that has an improved flowability when in a dry state and that is prevented from suffering from blocking and caking in a moistened state due to its specific particle diameter, specific compressibility rate, and the like. For example, Patent Literature 12 (International Publication No. WO2004/096304) discloses a superabsorbent polymer having an improved relationship between gel bed permeability and fluid retention capacity due to its containing unsaturated-acid-group-containing monomers, a crosslinking agent, water-insoluble inorganic powder, and the like.

CITATION LIST

Patent Literature

[Patent Literature 1]
Specification of U.S. Pat. No. 5,051,041
[Patent Literature 2]
Published Japanese Translation of PCT International Application, Tokuhyohei, No. 5-503492
[Patent Literature 3] Specification of U.S. Pat. No. 5,355,993
[Patent Literature 4]
Japanese Patent No. 3548575
[Patent Literature 5]
Japanese Patent No. 3659645
[Patent Literature 6]
Published Japanese Translation of PCT International Application, Tokuhyo, No. 2005-522391
[Patent Literature 7]
Published Japanese Translation of PCT International Application, Tokuhyo, No. 2006-528119
[Patent Literature 8]
Published Japanese Translation of PCT International Application, Tokuhyo, No. 2009-511393
[Patent Literature 9]
International Publication No. WO2006/109844
[Patent Literature 10]
International Publication No. WO2008/120742
[Patent Literature 11]
International Publication No. WO2005/075070
[Patent Literature 12]
International Publication No. WO2004/096304

Non-Patent Literature

[Non-patent Literature 1]
Handbook of Filters, 4th Edition, page 281 "3.9 Feeding" George Wypych, ChemTec Publishing, Toronto, 2016

SUMMARY OF INVENTION

Technical Problem

When continuously fed with use of a feeder, some water-absorbing agents are stable in feed rate and others are unstable in feed rate, and thereby stable production is hindered. Furthermore, changes in temperature, humidity, and/or the like during feeding may result in changes in the degree of aggregation of water-absorbing agent particles and the degree of adhesion of the water-absorbing agent to an apparatus, resulting in unstable feed rate.

It is known that the Carr's flowability index, relating to the flowability and jet flowability of particulate material, is used as an indicator in order to reduce the fluctuation of feed rate. However, the inventors of the present invention have found that the Carr's flowability index cannot be applied to all kinds of feeders and that, in a case where a specific feeder is used (e.g., a BSP-type apparatus which is a positive displacement pump for conveying particulate material is used), there is no correlation between the fluctuation of feed rate and the Carr's flowability index.

With regard to the above issues, the water-absorbing agents disclosed in Patent Literatures 9 to 11 still have some room for improvement in regard to the fluctuation of feed rate in a case where a specific feeder is used. Furthermore, the superabsorbent polymer disclosed in Patent Literature 12 contains water-insoluble inorganic powder and the like in order to ensure water permeability, and therefore is difficult to achieve the necessary level of powder flowability that is necessary when the superabsorbent polymer is subjected to, for example, a BSP-type apparatus.

As such, there have been a demand for a new indicator that can be used also in a case where a specific feeder such as a BSP-type apparatus is used, and a demand for a water-absorbing agent that can be obtained based on the indicator and that is stable in feed rate.

In view of the above issues, a main object of an aspect of the present invention is to provide a water-absorbing agent that causes no or little fluctuation of feed rate when fed with use of a feeder.

An object of another aspect of the present invention is to provide an accurate feeding method in which the amount of flow per unit time shows no or little fluctuation and the feed rate is stable as compared to conventional methods of feeding a water-absorbing agent.

Solution to Problem

The inventors of the present invention conducted diligent study to attain the above objects, and found that, in a case where a feeder used in the present invention is a so-called BSP-type apparatus (i.e., a positive displacement feeding apparatus), bulk density, compressibility rate, and angle of repose of powder in the apparatus are important factors relating to the flow of the powder, and that, by taking these factors into consideration, it is possible to obtain a correlation equation with highly improved predictivity. The inventors also found that a water-absorbing agent having a specific index obtained using the correlation equation and having a specific moisture absorption flowability is highly stable in feed rate. The inventors further found that, when a water-absorbing agent having a specific performance is conveyed with use of a specific feeder, the feed rate is stable (the feed mount per unit time shows no or little fluctuation), and that this makes it possible to achieve accurate feed rate of a water-absorbing agent (i.e., the rate at which a water-absorbing agent is fed shows no or little fluctuation).

Specifically, an embodiment of the present invention is a water-absorbing agent containing a water-absorbing resin as a main component, the water-absorbing agent satisfying the following (a) and (b):
  (a) K-index is 70 or more; and
  (b) Moisture absorption blocking ratio, after 30 minutes of standing at a temperature of 25° C. and a relative humidity of 80% RH, is 70 weight % or less,
  the K-index being defined by the following equation:

$$K\text{-index}=100-(-438+3.6\times\text{angle of repose}+3.5\times\text{angle of difference}+7.9\times\text{compressibility rate}+290\times\text{bulk density (EDANA method)}).$$

Advantageous Effects of Invention

An aspect of the present invention brings about an effect of making it possible to provide a water-absorbing agent that causes no or little fluctuation of feed rate when fed with use of a feeder.

Another aspect of the present invention brings about the following effect: it is possible to provide an accurate feeding method in which the amount of flow per unit time shows no or little fluctuation and the feed rate is stable as compared to conventional methods of feeding a water-absorbing agent, by, when carrying out continuous feeding of a water-absorbing agent containing SAP as a main component with use of a specific feeder, employing a water-absorbing agent satisfying K-index≥70.

DESCRIPTION OF EMBODIMENTS

Figure 1:
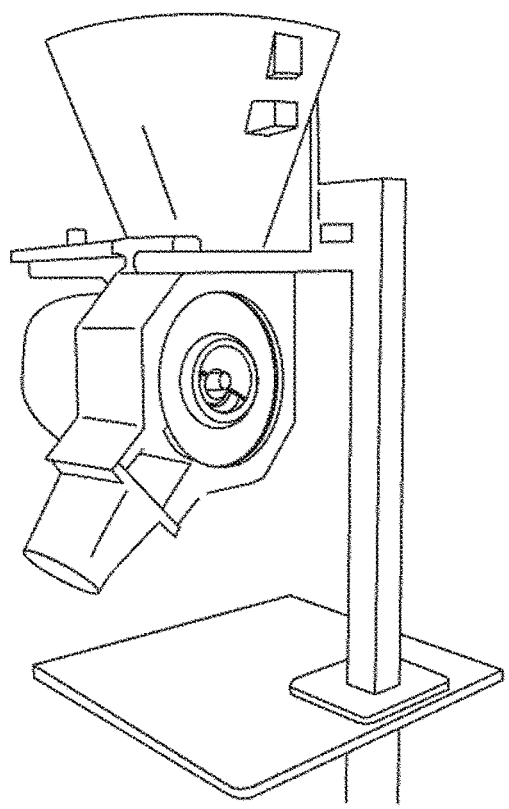
FIG. 1 is a perspective view illustrating an example of a feeder for use in the present invention.

The following description will discuss the present invention based on the best mode of the present invention. Throughout the present specification, any expression in a singular form should be understood to encompass the concept of its plural form unless particularly mentioned otherwise. Therefore, the article specifying a single form (e.g., "a", "an", "the") should be understood to encompass the concept of its plural form unless particularly mentioned otherwise. In addition, any term used in the present specification should be understood as ordinarily used in this technical field unless particularly mentioned otherwise. Therefore, unless defined otherwise, all of the technical terms and scientific terms used in the present specification mean as generally understood by a person skilled in the technical field to which the present invention belongs. If there is any conflict in meaning, the present specification (including the definitions) takes priority.

Embodiment 1

[1-1] Definitions of Terms (1-1-1) Water-Absorbing Resin

The term "water-absorbing resin" as used in Embodiment 1 refers to a water-swellable, water-insoluble polymer gelling agent that satisfies the following physical properties. Specifically, the term "water-absorbing resin" refers to a polymer gelling agent that satisfies the following physical properties: CRC (centrifuge retention capacity) defined in ERT 441.2-02 as "water-swelling property" is 5 g/g or more, and Ext (extractable) defined in ERT470.2-02 as "water-insolubility" is 50 weight % or less.

The water-absorbing resin can be designed as appropriate according to its purpose of use, and is not limited to any particular design. The water-absorbing resin is preferably a hydrophilic crosslinked polymer that has been obtained by crosslinking and polymerizing unsaturated monomers having a carboxyl group. The water-absorbing resin is not limited to a form in which the water-absorbing resin is wholly (that is, 100 weight %) a polymer, and can be a water-absorbing resin composition containing an additive and the like within a range in which the above-described physical properties (CRC and Ext) are satisfied.

The term "water-absorbing resin" as used in Embodiment 1 may refer to not only an end product but also an intermediate produced during a process of producing the water-absorbing resin (e.g., a hydrogel polymer after polymerization, a dried polymer after drying, a water-absorbing resin powder before surface crosslinking, or the like). In addition, the water-absorbing resin and the water-absorbing resin composition described above will also be collectively referred to as "water-absorbing resin". Examples of forms the water-absorbing resin include a sheet form, a fiber form, a film form, a particulate form, and a gel form. The water-absorbing resin of Embodiment 1 is preferably a particulate water-absorbing resin.

(1-1-2) Water-Absorbing Agent

The term "water-absorbing agent" as used in the present specification means a gelling agent which contains a water-absorbing resin as a main component and absorbs a water-based liquid. An example of a water-absorbing agent is one that is suitably used as a hygienic material for absorption of a water-based liquid.

The term "water-absorbing agent" as used in the present specification especially means a water-absorbing agent in the form of particles (powder). The term "water-absorbing agent in the form of particles (i.e., particulate water-absorbing agent)" is used to refer to a single particle of the particulate water-absorbing agent or an aggregate of a plurality of particles of the particulate water-absorbing agent. The term "particulate" means having the form of particles. A particle is a small grain-shaped solid or liquid object with a measurable size (according to the Glossary of Technical Terms in Japanese Industrial Standards, fourth edition, page 2002). In the present specification, a particulate water-absorbing agent may be simply referred to as "water-absorbing agent".

Note that the "water-based liquid" is not limited to water. Examples of the water-based liquid include urine, blood, sweat, feces, waste fluid, moisture, vapor, ice, a mixture of water and an organic solvent and/or an inorganic solvent, rain water, and ground water. The water-based liquid is thus not limited to any particular one, provided that the water-based liquid contains water. Preferable examples include urine, menstrual blood, sweat, and other body fluids.

(1-1-3) Polyacrylic Acid (Salt)

The term "polyacrylic acid (salt)" as used in Embodiment 1 refers to polyacrylic acid and/or a salt thereof, and refers to a polymer that contains, as a main component, a repeating unit of acrylic acid and/or a salt thereof (hereinafter referred to as "acrylic acid (salt)") and that contains a graft component as an optional component.

The term "main component" means that the acrylic acid (salt) is used (contained) ordinarily in an amount of 50 mol % to 100 mol %, preferably of 70 mol % to 100 mol %, more preferably of 90 mol % to 100 mol %, and even more preferably of substantially 100 mol %, relative to the total amount of monomers for use in polymerization (excluding an internal crosslinking agent).

(1-1-4) EDANA and ERT

The term "EDANA" is an acronym for the European Disposables and Nonwovens Associations. The term "ERT" is an acronym for EDANA Recommended Test Methods, which are European standard (de facto international standard) measuring methods for water-absorbing resin. For Embodiment 1, physical properties of water-absorbing resin are measured in conformity with the ERT master copy (2002 revised version; known literature) unless otherwise specified.

(1-1-5) CRC (ERT441.2-02)

The term "CRC" is an acronym for "centrifuge retention capacity", and means a fluid retention capacity without pressure (hereinafter referred to also as "fluid retention capacity") of a water-absorbing agent or of a water-absorbing resin.

Specifically, the CRC refers to a fluid retention capacity (unit: g/g) measured after 0.2 g of a water-absorbing agent or a water-absorbing resin contained in a nonwoven fabric bag is immersed in a large excess of a 0.9 weight % aqueous sodium chloride solution for 30 minutes so as to be allowed to freely swell, and then the water-absorbing resin is drained in a centrifuge (250 G).

Note that the CRC of a hydrogel polymer (hereinafter referred to as "gel CRC") was measured in the same manner as described above, except that the weight of a sample (water-absorbing agent or water-absorbing resin) and the free swelling period were changed to 0.4 g and 24 hours, respectively. In calculation of numerical values in the measurement, the weight of a resin solid content of a hydrogel polymer was used as the weight of the water-absorbing resin. In a case where each side of the hydrogel polymer had a size of 5 mm or more, the hydrogel polymer was, before the measurement, cut with use of scissors or the like so that the side had a size of 1 mm or less.

(1-1-6) AAP (ERT442.2-02)

The term "AAP" is an acronym for "absorption against pressure", and means a fluid retention capacity under pressure of a water-absorbing agent or a water-absorbing resin.

Specifically, "AAP" refers to a fluid retention capacity (unit: g/g) measured after 0.9 g of a water-absorbing agent or water-absorbing resin has been swollen in a large excess of a 0.9 weight % aqueous sodium chloride solution for 1 hour under a load of 4.83 kPa (49 g/cm$^2$, 0.7 psi). Note that in some cases the measurement may be carried out under a load of 2.06 kPa (21 g/cm$^2$, 0.3 psi).

Also note that ERT 442.2-02 uses the term "Absorption Under Pressure (AUP)", which refers to substantially the same thing as "AAP".

(1-1-7) PSD (ERT420.2-02)

The term "PSD" is an acronym for "particle size distribution", and means a particle size distribution of a water-absorbing agent or a water-absorbing resin. The particle size distribution is measured by sieve classification.

Note that the weight average particle diameter (D50), particle size distribution, and the logarithmic standard deviation (σζ) of particle size distribution are measured according to the same method as described in "(3) Mass-Average Particle Diameter (D50) and Logarithmic Standard Deviation (σζ) of Particle Diameter Distribution", which is a method disclosed in U.S. Pat. No. 7,638,570 or according to a method described later in the "(f) Logarithmic standard deviation (σζ) of particle size distribution" section in the [Measurement of physical properties of particulate water-absorbing agent or water-absorbing resin] section.

(1-1-8) Moisture Content (ERT430.2-02)

The term "moisture content" means a moisture content of a water-absorbing agent or a water-absorbing resin.

Specifically, a "moisture content" refers to a value (unit: weight %) calculated from a drying loss obtained by drying 4.0 g of a water-absorbing agent or a water-absorbing resin at 105° C. for 3 hours. Note that in some cases, measurement may be carried out under a condition in which the amount of the water-absorbing resin and the drying temperature are 1.0 g and 180° C., respectively.

(1-1-9) Ext (ERT470.2-02)

The term "Ext" is an abbreviation for "Extractables", and means a water-soluble content (water-soluble component amount) of a water-absorbing agent or water-absorbing resin.

Specifically, the "Ext" refers to the amount (unit: weight %) of a polymer dissolved in an aqueous solution after adding 1.0 g of a water-absorbing agent or water-absorbing resin to 200 ml of a 0.9 weight % aqueous sodium chloride solution and stirring the resulting mixture at 500 rpm for 16 hours. The amount of the dissolved polymer is measured by pH titration.

(1-1-10) Non-Uniformly Pulverized Shape

The term "non-uniformly pulverized shape" indicates a crushed or pulverized substance obtained by crushing a gel of a crosslinked polymer obtained through aqueous solution polymerization or by pulverizing a dried material of such a gel (preferably obtained by pulverizing a dried material). This crushed or pulverized substance is pulverized particles having non-uniform shape. The crushed or pulverized substance is preferably a crushed or pulverized substance obtained by aqueous solution polymerization. In contrast, spherical and/or ellipsoidal primary particles and sausage-shaped primary particles which are obtained by, for example, reversed phase suspension polymerization or droplet polymerization (carried out by, for example, spraying monomers), or granulated versions of those primary particles, are not in the "non-uniformly pulverized shape".

(1-1-11) Moisture Absorption Flowability

The "moisture absorption flowability" as used in Embodiment 1 evaluates blocking, caking, or powder flowability of a water-absorbing agent after the water-absorbing agent was left to stand for 30 minutes at an air temperature of 25° C. and a relative humidity of 80% RH. The moisture absorption flowability is evaluated based on "Moisture Absorption Blocking Ratio" (B.R.).

A particulate water-absorbing agent or water-absorbing resin of the present invention has a "moisture absorption blocking ratio (B.R.)" of preferably 0 weight % to 70 weight %, more preferably 0 weight % to 50 weight %, even more preferably 0 weight % to 40 weight %, particularly preferably 0 to 30 weight %, most preferably 0 weight % to 10 weight %. If the "moisture absorption blocking ratio (B.R.)" is more than 70 weight %, then the particulate water absorbing agent or water-absorbing resin is difficult to handle in humid conditions. This may pose a problem that, during production of a thin absorbent body for hygienic material, for example, the particulate water-absorbing agent or water-absorbing resin aggregates in a transport pipe in a production plant and therefore the transport pipe clogs and/or the particulate water-absorbing agent or water-absorbing resin cannot be uniformly mixed with hydrophilic fibers.

(1-1-12) Angle of Repose, Angle of Difference, Compressibility Rate, Bulk Density (EDANA Method), and Relevant Parameters In the present specification, the parameters used in the following correlation equation and related parameters are defined as below. These parameters are measured and calculated as described later in the "Measurement of powder property parameters" section.

Correlation equation $$K\text{-index}=100-(-438+3.6\times\text{angle of repose}+3.5\times\text{angle of difference}+7.9\times\text{compressibility rate}+290\times\text{bulk density (EDANA method)})$$

"Angle of repose": The angle between the horizontal plane and the slope of a powder pile formed by allowing a water-absorbing agent to fall freely.

"Angle of difference": Angle of repose−angle of fall (Angle of fall: After the angle of repose is formed, a shock is applied to the powder pile to collapse it. The angle of fall is the angle between the slope of the collapsed pile and the horizontal plane.)

"Compressibility rate": (Tight bulk density-loose bulk density)/tight bulk density×100.

("Loose bulk density": The packing density of a water-absorbing agent in a cup, measured after allowing the water-absorbing agent to fall freely into the cup.) ("Tight bulk density": The bulk density of the sample filled in the cup, measured after tapping down the sample after the loose bulk density was measured.)

"Bulk density (EDANA method)": Loose bulk density measured using an apparatus specified in the EDANA manual.

"Angle of spatula": Powder is piled up on a spatula blade, and then the blade is pulled up. The angle of spatula is the angle between the slope of the powder pile on the blade and the blade.

(1-1-13) Probe Insertion Work (PIW), and Probe Insertion Distance (PID)

The definition of the "probe insertion work (PIW)" is as follows. A probe (metal rod), which is an insertion member, is inserted vertically into a tightly packed water-absorbing agent or water-absorbing resin by 20 mm. The work done when the probe is inserted to a depth of 20 mm is the "probe insertion work (PIW)".

The definition of the "probe insertion distance (PID)" is as follows. A probe (metal rod), which is an insertion member, is vertically inserted into a tightly packed water-absorbing agent or water-absorbing resin. The length of a portion, which is thus inserted in the tightly packed water-absorbing agent or water-absorbing resin, of the probe is the "probe insertion distance (PID)". These are measured by the measurement method "probe insertion test" described later.

(1-1-14) Feed (Verb), Feed (Noun), and Feed Rate

In the present specification, the term "feed" (verb) means supplying a water-absorbing agent (or bulk material) with use of a supplying apparatus (feeder). Accordingly, the term "feed" (noun) refers to a water-absorbing agent (or bulk material) which is supplied from and discharged from the supplying apparatus (feeder), instead of meaning a water-absorbing agent (or bulk material) that is initially introduced into the supplying apparatus (feeder).

The term "feed rate" refers to the rate at which a water-absorbing agent (or bulk material) is supplied from and discharged from a supplying apparatus (feeder), instead of meaning the rate at which the water-absorbing agent (or bulk material) is initially introduced into the feeder.

(1-1-5) Other

In the present specification, any range of "X to Y" denotes "X or more and Y or less". Unless otherwise noted, the unit of weight "t (ton)" denotes "metric ton", and the unit "ppm" denotes "ppm by weight". Furthermore, the terms "weight" and "mass" are used synonymously, the terms "parts by weight" and "parts by mass" are used synonymously, and "weight %" and "mass %" are used synonymously. Further, " . . . acid (salt)" means " . . . acid and/or salt thereof", and "(meth)acrylic" means "acrylic and/or methacrylic".

For convenience, "liter" may be referred to as "l" or "L", and "weight %" may be referred to as "wt %". Furthermore, in a case where trace components are measured, values equal to or less than a detection limit is indicated as N.D. (Non Detected).

[1-2] Water-Absorbing Agent

A water-absorbing agent in accordance with Embodiment 1 contains a water-absorbing resin as a main component, and satisfies the following conditions (a) and (b):

(a) K-index is 70 or more; and
(b) Moisture absorption blocking ratio, after 30 minutes of standing at a temperature of 25° C. and a relative humidity of 80% RH, is 70 weight % or less.

As used herein, the "K-index" is an index obtained from the following correlation equation:

$$K\text{-index}=100-(-438+3.6\times\text{angle of repose}+3.5\times\text{angle of difference}+7.9\times\text{compressibility rate}+290\times\text{bulk density (EDANA method)}).$$

Note that the water-absorbing agent is not particularly limited as to its form, provided that the above conditions (a) and (b) are satisfied. The water-absorbing agent may be in the form of fibers or a gel. The water-absorbing agent is preferably in the form of particles (also called "in the form of powder"), and is more preferably in the form of particles having a particle size distribution falling within the range described later.

A water-absorbing agent in accordance with Embodiment 1, which satisfies both the conditions (a) and (b), causes no or little fluctuation of feed rate and is not easily affected by changes in feed conditions (temperature, humidity, and the like), and can be stably and accurately supplied at a desired feed rate, even when continuously fed with use of a positive displacement supplying apparatus. Accordingly, absorbent bodies produced from the water-absorbing agent in accordance with Embodiment 1 have no or little variation in performance and the like and ensure stable quality.

(1-2-1) Composition of Water-Absorbing Agent

A water-absorbing agent in accordance with Embodiment 1 contains a water-absorbing resin as a main component. More specifically, a water-absorbing agent in accordance with Embodiment 1, when in a dry state containing no water, contains a water-absorbing resin in an amount of at least 50 weight %, preferably 60 weight % or more, more preferably 70 weight % or more, even more preferably 80 weight % or more, and particularly preferably 90 weight % or more. The upper limit of the amount of the water-absorbing resin contained may be 100 weight %, and may be, for example, 99 weight %, 97 weight %, or about 95 weight %. The water-absorbing agent may contain some commonly-used additive(s) in addition to the water-absorbing resin. The water-absorbing agent may further contain water in addition to such an additive(s). Furthermore, the water-absorbing agent may be composed of a water-absorbing resin composition that is composed of the water-absorbing resin, an additive(s), and/or water.

Examples of the water-absorbing resin, contained as a main component in the water-absorbing agent in Embodiment 1, include polyacrylic acid (salt)-based resins, polysulfonic acid (salt)-based resins, maleic anhydride (salt)-based resins, polyacrylamide-based resins, polyvinyl alcohol-based resins, polyethylene oxide-based resins, polyaspartic acid (salt)-based resins, polyglutamic acid (salt)-based resins, polyalginic acid (salt)-based resins, starch-based resins, and cellulose-based resins. The water-absorbing resin in Embodiment 1 is preferably a polyacrylic acid (salt)-based resin.

(1-2-2) K("KONA")-Index

In the present specification, the term "K-index" is an abbreviation for "KONA-index". The term "KONA" is a Japanese word which means "powder".

In Embodiment 1, four parameters calculated based on measurement carried out on the water-absorbing agent, and equivalent parameters thereof, were studied closely. As a result, it was found that the following equation is most appropriate:

$$K\text{-index}=100-(-438+3.6\times\text{angle of repose}+3.5\times\text{angle of difference}+7.9\times\text{compressibility rate}+290\times\text{bulk density (EDANA method)}),$$

and therefore the equation (which may be referred to as "correlation equation (K-index)") was employed.

The above "equivalent parameters" refer to parameters that can be derived from the respective four parameters (bulk density, compressibility rate, angle of repose, and angle of difference) calculated based on the measurement carried out on the water-absorbing agent or water-absorbing resin or refer to parameters indicating substantially the same properties as those indicated by the four parameters (for example, the parameter "bulk density" can be used substantially synonymously with "bulk density" and "apparent specific gravity"). Errors that are derived when such equivalent parameters are used instead of the four parameters calculated based on measurement carried out on the water-absorbing agent or water-absorbing resin are tolerated. Alternatively, a water-absorbing agent or water-absorbing resin intrinsically having the properties indicated by these parameters may be purchased and used as appropriate. Alternatively, a water-absorbing agent or water-absorbing resin, whose four parameters calculated based on the measurement carried out on the water-absorbing agent or water-absorbing resin or whose equivalent parameters thereof are presented by a supplier, may be purchased and used as appropriate. For example, a water-absorbing agent or water-absorbing resin, whose bulk density (EDANA method) is presented by a water-absorbing resin manufacturer, may be purchased and used as appropriate. As such, in Embodiment 1, the scope of the correlation equation (K-index) includes variations in which the above equivalent parameters of a water-absorbing agent containing a water-absorbing resin as a main component are used. Specifically, the scope of the correlation equation (K-index) includes variations which are different from the correlation equation (K-index) in that one or more of the four parameters (selected from the group consisting of bulk density, compressibility rate, angle of repose, and angle of difference), which are used in the correlation equation (K-index), of a water-absorbing agent containing a water-absorbing resin as a main component is/are replaced by an equivalent parameter(s).

In another aspect of Embodiment 1, the scope of the correlation equation (K-index) includes variations in which one or more but not all of the four parameters of a water-absorbing agent containing a water-absorbing resin as a main component is/are used. Specifically, the scope of the correlation equation (K-index) includes variations in which at least one, at least two, or at least three of the four parameters (selected from the group consisting of bulk density, compressibility rate, angle of repose, and angle of difference), which are used in the correlation equation (K-index), of a water-absorbing agent containing a water-absorbing resin as a main component is/are used. The scope of the correlation equation (K-index) also includes variations in which one or more of these parameter(s) is/are replaced by an equivalent parameter(s).

In one preferred embodiment, preferred ranges (upper limits and lower limits) of the parameters in the correlation equation (K-index) are as follows. It should be understood that, provided that the requirements concerning the correlation equation (K-index) are satisfied, every combination of an upper limit and a lower limit of each of the four parameters, and any value between the upper limit and the lower limit (the upper limit and the lower limit inclusive), are encompassed in the scope of Embodiment 1.

Bulk density (EDANA method): Examples of preferred lower limit include 0.5 g/mL, 0.53 g/mL, 0.55 g/mL, and 0.57 g/mL, and examples of preferred upper limit include 0.9 g/mL, 0.85 g/mL, 0.82 g/mL, and 0.80 g/mL.

Compressibility rate: Examples of preferred lower limit include 5%, 7%, 9%, and 10%, and examples of preferred upper limit include 20%, 18%, 16%, and 14%.

Angle of repose: Examples of preferred lower limit include 25°, 27°, 29°, and 30°, and examples of preferred upper limit include 45°, 43°, 41°, and 40°.

Angle of difference: Examples of preferred lower limit include 2°, 5°, 6°, and 8°, and examples of preferred upper limit include 20°, 18°, 16°, and 15°.

Preferred ranges of each parameter, which satisfy the requirements concerning the K-index, are as follows. Typically, a preferred range of the bulk density (EDANA method) is 0.5 g/mL to 0.9 g/mL, a preferred range of the compressibility rate is 5% to 20%, a preferred range of the angle of repose is 25° to 45°, and a preferred range of the angle of difference is 2° to 20°. In Embodiment 1, it is preferable that at least one, at least two, at least three, particularly four of the four parameters fall within the above ranges. It is more preferable that the bulk density, the degree of compaction, the angle of repose, and the angle of difference are controlled to fall within the above ranges. This makes it possible to obtain a water-absorbing agent that satisfies (a) K-index≥70 and (b) moisture absorption blocking ratio≤70 weight %. A method of adjusting each parameter is not particularly limited. Each parameter can be adjusted by, for example, a method by which the particle size distribution of the water-absorbing resin is controlled or a method by which the type and amount of an additive(s) used (optional) are controlled.

Note that the Carr's flowability index can be calculated using various parameters of a water-absorbing agent. However, when the water-absorbing agent was continuously fed with use of a positive displacement supplying apparatus, there appeared no correlation between the fluctuation of feed rate and the Carr's flowability index, and the Carr's flowability index was found to be inappropriate as an indicator in the present invention. That is, there appeared no correlation between the standard deviation σ of feed rate and the Carr's flowability index. In contrast, it was found that, with use of the K-index of the present invention, a value that has a higher correlation with the fluctuation of feed rate than the Carr's flowability index does can be derived and that the standard deviation σ can be estimated.

In Embodiment 1, the K-index of a water-absorbing agent is K-index≥70, preferably K-index≥75, more preferably K-index≥80. When the K-index of the water-absorbing agent is 70 or more, the standard deviation σ of the rate (feed rate) at which the water-absorbing agent is fed from the feeder is small, making it possible to reduce the fluctuation of feed amount per unit time. In a case where K-index≥75 or K-index≥80, the tendency of reducing the fluctuation of feed amount per unit time is more noticeable, and therefore such K-indices are more preferred. The upper limit of the K-index is, for example, 150, preferably 120, more preferably 110, particularly preferably 100, most preferably 95.

Note, here, that the four parameters of a water-absorbing agent, employed when calculating the K-index, may be any values obtained by a measurement method known in this field, may be values presented by a supplier, or may be values available from some other information source. Alternatively, a water-absorbing agent or water-absorbing resin, whose measured or calculated four parameters are provided by a supplier, may be purchased and used as appropriate. For example, with regard to bulk density (EDANA method), a water-absorbing agent or water-absorbing resin whose bulk density (EDANA method) is presented by a water-absorbing resin manufacturer may be purchased and used as appropriate.

Note that the standard deviation σ (unit: g/min) of feed rate is a value calculated by a method described later in the Examples section.

(1-2-3) Moisture Absorption Blocking Ratio (B.R./Blocking Ratio)

A water-absorbing agent in accordance with Embodiment 1 has the "K-index" falling within the foregoing range, and also has a low moisture absorption blocking ratio falling within a specific range (in other words, high anti-caking ratio).

A water-absorbing agent in accordance with Embodiment 1 has a moisture absorption blocking ratio (B.R.) of 70 weight % or less, preferably 50 weight % or less, more preferably 40 weight % or less, even more preferably 30 weight % or less, even more preferably 20 weight % or less, particularly preferably 10 weight % or less. The lower limit, in calculation principle, is 0 weight %.

According to the above arrangement, when the K-index and the moisture absorption blocking ratio (B.R.) of a water-absorbing agent are controlled to be 70 or more and 70 weight % or less, respectively, the feed rate of the water-absorbing agent can be kept constant without having to strictly control the conditions (such as humidity) under which feeding is carried out. Accordingly, the water-absorbing agent can be used stably without being influenced by conditions under which the water-absorbing agent is fed (e.g., conditions under which an apparatus for producing a thin absorbent body for hygienic material is operated).

When the moisture absorption blocking ratio (B.R.) of the water-absorbing agent is greater than 70 weight %, the degree of aggregation of water-absorbing agent particles and the degree of adhesion of the particles to an apparatus change as the conditions such as humidity change. This can result in unstable feed rate. Furthermore, under humid conditions, the water-absorbing agent is likely to become difficult to handle and the water-absorbing agent aggregates in a transport pipe in a production plant. This may result in a problem that the transport pipe clogs and/or the water-absorbing agent cannot be uniformly mixed with other components such as hydrophilic fibers.

Note that the moisture absorption blocking ratio (B.R.) in the present invention is a value calculated by a method described later in the Examples section.

(1-2-4) Powder Flowability (F.R./Flow-Rate)

The powder flowability (F.R.) of a water-absorbing agent in accordance with Embodiment 1 is preferably 10.0 g/s or more, more preferably 10.5 g/s or more, even more preferably 11.0 g/s or more, particularly preferably 11.5 g/s or more, most preferably 12.0 g/s or more. The upper limit of the powder flowability (F.R.) is preferably 15.0 g/s or less, more preferably 14.5 g/s or less, even more preferably 14.0 g/s or less, particularly preferably 13.5 g/s or less, most preferably 13.0 g/s or less.

When the powder flowability (F.R.) of the water-absorbing agent falls within the above range, the water-absorbing agent receives the actions of appropriate pressure application and/or pressure release within a positive displacement supplying apparatus, and is supplied at a stable feed rate.

Note that, in Embodiment 1, the powder flowability (F.R.) is a value calculated by a method described later in the Examples section. A method of calculating powder flowability (F.R.) will be described later in detail in the Examples section.

(1-2-5) Surface Tension

A water-absorbing agent in accordance with Embodiment 1 has a surface tension (in other words, the surface tension of an aqueous dispersion of the water-absorbing agent) of preferably 65 mN/m or more, more preferably 68 mN/m or more, even more preferably 70 mN/m or more. The upper limit of the surface tension is not particularly limited, and is, generally, preferably 75 mN/m or less.

A surface tension of the water-absorbing agent falling within the above range provides an advantage that the amount of liquid returning from an absorbent article containing the water-absorbing agent when the absorbent article is in actual use (such an amount of liquid is usually called "re-wet") is small and that the absorbent body is superior for use in sanitary material such as a disposable diaper.

Note that, in Embodiment 1, the surface tension of the water-absorbing agent is a value calculated by a method described later in the Examples section.

(1-2-6) Diffusing Absorbency (DAP/Diffusing Absorbency Under Pressure)

A "diffusing absorbency (DAP)" in Embodiment 1 refers to a physical property value for evaluating an absorption amount of a water-absorbing resin, and takes account of diffusion ability of a water-based liquid in a case where a water-absorbing resin has a high basis weight and is in a state where particles of the water-absorbing resin are in close contact due to an external force.

The diffusing absorbency in Embodiment 1 is calculated from a measured value obtained by measurement under a load of 1.96 kPa after 10 minutes from a start of absorption. A measuring method will be described later in detail in the Examples section.

The diffusing absorbency of the water-absorbing agent in accordance with Embodiment 1 is preferably 15 g/g or more, more preferably 18 g/g or more, most preferably 20 g/g or more. Typically, a diffusing absorbency of a water-absorbing agent which has been subjected to a surface-crosslinking treatment is 15 g/g or more. However, some water-absorbing agents, though not common, have a low diffusing absorbency. Furthermore, the diffusing absorbency of the water-absorbing agent sometimes decreases under the influence of an additive(s) added after the surface-crosslinking treatment. A water-absorbing agent having a diffusing absorbency of 15 g/g or more has a good diffusion property in an absorbent body and is capable of exhibiting sufficient performance as an absorbent body. The upper limit of the diffusing absorbency of the water-absorbing agent is not particularly limited, and is preferably higher. From the viewpoint of balance with other physical properties, the upper limit of the diffusing absorbency is typically about 40 g/g or less (35 g/g or less or 30 g/g or less).

(1-2-7) Probe Insertion Work (PIW)

With regard to the probe insertion work (PIW) of a water-absorbing agent in accordance with Embodiment 1, a method of measuring the probe insertion work (PIW) in a probe insertion test will be detailed later in the Examples section. A lower probe insertion work (when a probe (metal rod) is inserted by 20 mm) indicates a lower coefficient of internal friction and lower frictional force of the water-absorbing agent as powder, and thus indicates higher lubrication of the water-absorbing agent.

It is preferable that PIW≤30000 gf×mm, because there is a tendency that fluctuation of the amount of the water-absorbing agent fed from the feeder per unit time is small and the water-absorbing agent can be supplied more stably. It is more preferable that PIW≤20000 gf×mm, because such a tendency becomes more noticeable.

In one preferred embodiment, the probe insertion work (PIW) is preferably 100 gf×mm or more, more preferably 1000 gf×mm or more, even more preferably 4000 gf×mm or more. The probe insertion work (PIW) is preferably 30000 gf×mm or less, more preferably 20000 gf×mm or less, even more preferably 15000 gf×mm or less, 13000 gf×mm or less, 10000 gf×mm or less, particularly preferably 8000 gf×mm or less.

(1-2-8) Moisture Content

The moisture content of a water-absorbing agent in accordance with Embodiment 1 is a value (unit: weight %) calculated from a drying loss obtained by drying the water-absorbing agent at 180° C. for 3 hours. The moisture content of the water-absorbing agent is preferably 10 weight % or less, more preferably 7 weight % or less, even more preferably 5 weight % or less. The lower limit of the moisture content of the water-absorbing agent is preferably 0.5 weight % or more, more preferably 1.0 weight % or more, even more preferably 1.5 weight % or more, particularly preferably 2.0 weight % or more.

It is preferable that the moisture content of the water-absorbing agent is 10 weight % or less, because the water-absorbing agent can be easily controlled to satisfy the above conditions (a) K-index≥70 and (b) moisture absorption blocking ratio≤70 weight % and, in addition, reductions in fluid retention capacity without pressure and fluid retention capacity under pressure are prevented or reduced, and also the water-absorbing resin is easy to handle. It is preferable that the moisture content of the water-absorbing agent is 0.5 weight % or more, because reductions in fluid retention capacity under pressure that would be caused by mechanical damage during, for example, conveyance are prevented or reduced.

Note that, in Embodiment 1, the moisture content of the water-absorbing agent is a value calculated by a method described later in the Examples section.

(1-2-9) Particle Size Distribution

Water-absorbing resin powder and water-absorbing agent obtained in the present invention have, in order to satisfy the above conditions (a) K-index≥70 and (b) moisture absorption blocking ratio≤70 weight %, a weight average particle diameter (D50) of preferably 200 μm to 600 μm, more preferably 200 μm to 550 μm, even more preferably 250 μm to 500 μm, particularly preferably 350 μm to 450 μm. The proportion of particles having a particle diameter less than 150 μm is preferably 10 weight % or less, more preferably 5 weight % or less, even more preferably 1 weight % or less. The proportion of particles having a particle diameter of 850 μm or more is preferably 5 weight % or less, more preferably 3 weight % or less, even more preferably 1 weight % or less. The lower limit of the proportion of particles having a particle diameter less than 150 μm, and the lower limit of the proportion of particles having a particle diameter of 850 μm or more, are preferably smaller. Each of the proportions is preferably 0 weight %, but may be about 0.1 weight %. Furthermore, the logarithmic standard deviation (σζ) of particle size distribution is preferably 0.20 to 0.50, more preferably 0.25 to 0.40, even more preferably 0.27 to 0.35. Note that the particle size distribution is measured with use of standard sieves in accordance with a measuring method disclosed in U.S. Pat. No. 7,638,570 and a measuring method disclosed in EDANA ERT 420.2-02.

(1-2-10) Other Physical Properties

In a case where a water-absorbing agent in accordance with Embodiment 1 is used for a sanitary material (such as disposable diaper), it is preferable that at least one, preferably at least two including AAP, most preferably all of the following physical properties (a) to (c) of the water-absorbing agent are controlled to fall within desired ranges.

The water-absorbing agent in accordance with Embodiment 1 is not particularly limited as to its form, and is preferably in the form of particles. The following description will discuss physical properties of the water-absorbing agent or water-absorbing resin. The physical properties below are measured in conformity with EDANA method unless otherwise specified.

(a) CRC (Fluid Retention Capacity without Pressure)

The CRC (fluid retention capacity without pressure) of a water-absorbing agent in accordance with Embodiment 1 is 30 g/g to 50 g/g, preferably 31 g/g to 50 g/g, 32 g/g to 50 g/g, 33 g/g to 50 g/g, 34 g/g to 50 g/g, 35 g/g to 50 g/g, 36 g/g to 50 g/g, 30 g/g to 49 g/g, 30 g/g to 48 g/g, 30 g/g to 47 g/g, 30 g/g to 46 g/g, 30 g/g to 45 g/g, 30 g/g to 44 g/g, 30 g/g to 43 g/g, 30 g/g to 42 g/g, 30 g/g to 41 g/g, 30 g/g to 40 g/g, 30 g/g to 39 g/g, or 30 g/g to 38 g/g.

If the CRC is less than 5 g/g, then an absorption amount is small. This renders a water-absorbing agent unsuitable as an absorbent body of a sanitary material such as a disposable diaper. If the CRC is more than 70 g/g, then a rate at which, for example, a body fluid such as urine or blood is absorbed decreases. This renders a water-absorbing agent unsuitable for use in, for example, a disposable diaper having a high water absorption speed. Note that CRC can be controlled with use of, for example, an internal crosslinking agent and/or a surface-crosslinking agent.

(b) Gel CRC

The CRC of a hydrogel polymer before gel-crushing (referred to as "gel CRC") is preferably 33 g/g or more. A gel CRC of less than 10 g/g or of more than 45 g/g is not preferable because it becomes difficult to control the particle shape and the particle size distribution during the gel-crushing. In order to achieve such a gel CRC, an added amount of crosslinking agent during polymerization, polymerization concentration, or the like may be controlled as appropriate. Note that it is a well-known fact that a water-absorbing agent or a water-absorbing resin preferably has a high gel CRC. It was found in Embodiment 1 that a gel CRC of more than 45 g/g makes it difficult to control the particle shape and the particle size distribution.

(c) Fluid Retention Capacity Under Pressure 0.7 Psi (AAP0.7)

The fluid retention capacity under pressure 0.7 psi (AAP0.7) of a water-absorbing agent in accordance with Embodiment 1 is preferably 15 g/g or more, more preferably 18 g/g or more, even more preferably 20 g/g or more, particularly preferably 22 g/g or more, most preferably 24 g/g or more. The upper limit is not particularly limited, and is preferably 30 g/g or less.

In a case where the AAP0.7 is less than 15 g/g, the amount of liquid returning from an absorbent body when a pressure is exerted on the absorbent body (such an amount is usually called "re-wet") is large, and therefore such a water-absorbing agent is not suitable as an absorbent body of a sanitary material such as a disposable diaper. Note that the AAP0.7 of the water-absorbing agent can be controlled by, for example, controlling particle size or with use of a surface-crosslinking agent.

(1-2-11) Additive

A water-absorbing agent in accordance with Embodiment 1 preferably contains at least one additive selected from the following group, from the viewpoint of improvement in water absorption speed, liquid permeability, moisture absorption flowability, and the like of the water-absorbing agent and also for adjusting the K-index of the water-absorbing agent. That is, the water-absorbing agent preferably contains at least one additive selected from the group consisting of polyvalent metal salts, surfactants, hydrophilic polymer compounds, cationic polymers, chelating agents, inorganic reducing agents, and hydroxycarboxylic acid compounds.

In particular, for the purpose of adjusting the K-index, the water-absorbing agent preferably contains at least one additive selected from the group consisting of polyvalent metal salts, surfactants, and hydrophilic polymer compounds, and more preferably contains at least one additive including a polyvalent metal salt. It is more preferable that the water-absorbing agent contains two kinds of additive selected from the group consisting of polyvalent metal salts, surfactants, and hydrophilic polymer compounds. It is particularly preferable that the water-absorbing agent contains all the three kinds of additive in combination. According to this arrangement, since the water-absorbing agent contains at least one additive selected from the group consisting of polyvalent metal salts, surfactants, and hydrophilic polymer compounds, the K-index and the moisture absorption blocking ratio can be easily controlled to fall within desired ranges. This makes it possible to reduce the fluctuation of feed rate.

In the present invention, it was found that a water-absorbing agent satisfying the conditions (a) K-index≥70 and (b) moisture absorption blocking ratio≤70 weight % attains the foregoing object. In order to obtain a water-absorbing agent in accordance with the present invention, it is important to prepare the water-absorbing agent so that the novel parameters, K-index and moisture absorption blocking ratio, satisfy the conditions (a) K-index≥70 and (b) moisture absorption blocking ratio≤70 weight %. A method for producing the water-absorbing agent in accordance with the present invention is not particularly limited. The water-absorbing agent is preferably produced by a later-described technique so that the water-absorbing agent, which contains a water-absorbing resin as a main component, satisfies the conditions (a) K-index≥70 and (b) moisture absorption blocking ratio≤70 weight %. For example, the water-absorbing agent in accordance with the present invention is produced by a technique by which the moisture content and particle size distribution of the water-absorbing agent are controlled or by a technique by which the amount of an additive(s) (optional) and when the additive(s) (optional) is/are added are controlled.

On the contrary, inorganic fine particles such as water-insoluble inorganic powder may cause a reduction in flowability of the water-absorbing agent as powder, and therefore the amount of inorganic fine particles used as an additive(s) in the water-absorbing agent in accordance with Embodiment 1 is preferably smaller or it is preferable that no such additives are used. The amount of inorganic fine particles used (added) is preferably less than 0.5 weight %, more preferably less than 0.1 weight %, even more preferably less than 0.05 weight %, particularly preferably less than 0.01 weight %, relative to 100 parts by weight of water-absorbing resin powder. It is most preferable that no inorganic fine particles are used.

(1. Polyvalent Metal Salt)

A polyvalent metal salt suitable for use in Embodiment 1 is a divalent or more metal salt which is in the form of powder. Given that the water-absorbing agent produced in the present invention is used in an absorbent body for hygienic material such as a diaper, it is preferable to select a polyvalent metal salt that does not color the water-absorbing agent and that is less toxic to human bodies.

Examples of a polyvalent metal salt that can be used in the present invention include water-insoluble polyvalent metal salts such as metallic soap and hydrotalcite. For maintaining effects of the polyvalent metal salt efficiently for the long term, it is preferable to select a water-soluble polyvalent metal salt that can dissolve in deionized water having ordinary temperature (25° C.) at a concentration of 5 weight % or more. It is more preferable to select and use a polyvalent metal salt that can dissolve in deionized water having ordinary temperature (25° C.) at a concentration of 10 weight % or more, even more preferably 20 weight % or more.

Examples of a polyvalent metal salt that can be used in the present invention include water-insoluble polyvalent metal salts such as metallic soap and hydrotalcite, and also include water-soluble polyvalent metal salts such as aluminum chloride, polyaluminum chloride, aluminum sulfate, aluminum nitrate, potassium aluminum bis(sulfate), sodium aluminum bis(sulfate), potassium alum, ammonium alum, sodium alum, sodium aluminate, calcium chloride, calcium nitrate, magnesium chloride, magnesium sulfate, magnesium nitrate, zinc chloride, zinc sulfate, zinc nitrate, zirconium chloride, zirconium sulfate, and zirconium nitrate. Also from the viewpoint of solubility with an absorbed liquid such as urine, it is preferable to use any of the foregoing water-soluble polyvalent metal salts in the form containing crystal water. Aluminum compounds are particularly preferred, among which aluminum chloride, polyaluminum chloride, aluminum sulfate, aluminum nitrate, potassium aluminum bis(sulfate), sodium aluminum bis(sulfate), potassium alum, ammonium alum, sodium alum, and sodium aluminate are preferred as a water-soluble polyvalent metal salt. Aluminum sulfate is particularly preferred. Hydrated crystalline powder such as powder of aluminum sulfate octadecahydrate and aluminum sulfate tetradeca-, pentadeca-, hexadeca-, heptadeca-, and octadecahydrates can be most suitably used. One of such polyvalent metal salts may be used individually or two or more of them may be used in combination.

A polyvalent metal salt that can be used in the present invention is preferably in the form of particles. The particle diameter of the polyvalent metal salt is preferably smaller than the particle diameter of the water-absorbing resin powder from the viewpoint of mixing property. The weight average particle diameter of the polyvalent metal salt is preferably 500 µm or less, more preferably 400 µm or less. From the viewpoint of performance, the polyvalent metal salt is preferably in the form of particles 20 weight % or more, relative to the total amount of the polyvalent metal salt, of which have a particle diameter of 150 µm or less, and is most preferably in the form of particles 30 weight % or more, relative to the total amount of the polyvalent metal salt, of which have a particle diameter of 150 µm or less.

A polyvalent metal salt in accordance with the present invention (i) may be dry blended, in the form of powder, with the water-absorbing resin powder, but (ii) is preferably mixed with the water-absorbing resin powder in the following manner: the polyvalent metal salt is dissolved in water to obtain an aqueous solution or dispersed in water to obtain an aqueous dispersion and then the aqueous solution or the aqueous dispersion is mixed with the water-absorbing resin powder, particularly preferably dissolved in water to obtain an aqueous solution and then the aqueous solution is mixed with the water-absorbing resin powder. In the above case (ii), for the purpose of preventing polyvalent metal ions (e.g., aluminum ions) from penetrating and/or diffusing into the water-absorbing resin powder, the aqueous solution contains the polyvalent metal salt at a concentration of preferably 50 weight % or more, more preferably 60 weight % or more, even more preferably 70 weight % or more, even more preferably 80 weight % or more, particularly preferably 90 weight % or more, relative to saturated concentration of the polyvalent metal salt (saturated concentration at the temperature of liquid during mixing). Needless to say, the aqueous solution may contain the polyvalent metal salt at a concentration equal to the saturated concentration of the polyvalent metal salt.

In a case where a polyvalent metal salt is added, the amount of the polyvalent metal salt used (added) is, from the viewpoint of, for example, ensuring flowability in a dry state and in a moistened state, preferably 0.001 parts by weight to 10 parts by weight, more preferably 0.01 parts by weight to 5 parts by weight, even more preferably 0.1 parts by weight to 2 parts by weight, relative to 100 parts by weight of the water-absorbing resin powder. When the polyvalent metal salt is added to a water-absorbing resin or water-absorbing agent in an amount that falls within the above range, the K-index, moisture absorption blocking ratio, and the like are easily controlled to fall within desired ranges. When the amount of the polyvalent metal salt added is more than 10 parts by weight, absorption properties such as CRC and AAP may decrease.

A method of adding a polyvalent metal salt to a water-absorbing resin or water-absorbing agent is, for example, a method by which, in any step of a process for producing the water-absorbing resin or water-absorbing agent, a polyvalent metal salt is added once or twice or more times. Specifically, the polyvalent metal salt can be added in any of the following production steps: monomer preparation, polymerization, gel-crushing (optional), drying, pulverizing after drying, classification, surface-crosslinking, fine powder recovery, sizing, granulation, and the like. A preferred method is a method by which a polyvalent metal salt is added to a water-absorbing resin after polymerization and after drying. A typical example is a method by which a polyvalent metal salt is added to water-absorbing resin powder concurrently with or before or after surface-crosslinking. A polyvalent metal salt as-is may be added in any step, or may be dissolved in a liquid (or water) to obtain a solution (or an aqueous solution) or dispersed into water to obtain an aqueous dispersion and then the solution or dispersion may be added. A polyvalent metal salt or its solution alone may be added in any step, or a polyvalent metal salt or its solution may be added together with some other additive discussed earlier. In a case where a plurality of additives are added, such additives may be dissolved in a liquid to obtain a single solution or may be mixed together and then the solution or the mixture may be added. Alternatively, the additives may be added separately from each other. In a case where a plurality of additives are added, the order in which the additives are added is not particularly limited.

Addition of a polyvalent metal salt to a water-absorbing resin or water-absorbing agent, particularly addition of a polyvalent metal salt to particle surfaces, makes it possible to prevent or reduce variations of powder flowability resulting from temperature and humidity changes, and makes it possible to keep the powder flowability substantially the same as that at room temperature even when, for example, heated and kept hot.

(2. Surfactant)

A water-absorbing agent in accordance with the present invention may contain a surfactant.

The term "surfactant" as used in the present invention refers to an agent whose molecules have both a hydrophilic portion and a lipophilic (hydrophobic) portion and which is strongly adsorbed on a surface of an object due to the balance between hydrophilicity and hydrophobicity to modify a surface property of that object.

Examples of a surfactant for use in Embodiment 1 include anionic surfactants, nonionic surfactants, cationic surfactants, and amphoteric surfactants.

The surfactant for use in the present invention is not particularly limited as to its HLB (hydrophile-lipophile balance). The HLB is within the range of preferably from 8 to 18, more preferably from 9 to 17, even more preferably from 10 to 17. When the HLB falls within the above range, the flowability and bulk density of the water-absorbing agent can be improved more suitably.

Examples of the anionic surfactant include fatty acid salts such as mixed fatty acid sodium soap, tack dry beef tallow fatty acid sodium soap, stearic acid sodium soap, oleic acid potassium soap, and castor oil potassium soap; alkyl sulfate ester salts such as sodium lauryl sulfate, higher alcohol sodium sulfate, and triethanolamine lauryl sulfate; alkyl benzene sulfonates such as sodium dodecylbenzenesulfonate; alkyl naphthalene sulfonates such as sodium alkylnaphthalenesulfonates; alkyl sulfosuccinates such as sodium dialkylsulfosuccinates; alkyl diphenyl ether disulfonates such as sodium alkyl diphenyl ether disulfonates; alkyl phosphates such as potassium alkyl phosphates; polyoxyethylene alkyl (or alkyl allyl) sulfates such as sodium polyoxyethylene lauryl ether sulfate, sodium polyoxyethylene alkyl ether sulfates, triethanolamine sulfate salts of polyoxyethylene alkyl ethers, and sodium polyoxyethylene alkyl phenyl ether sulfates; special reaction type anionic surfactants; special carboxylic acid type surfactants; naphthalene sulfonic acid formalin condensates such as a sodium salt of β-naphthalenesulfonic acid formalin condensate and a sodium salt of special aromatic sulfonic acid formalin condensate; special polycarboxylic acid type polymer surfactants; and polyoxyethylene alkyl phosphate esters.

Examples of the nonionic surfactant include polyoxyethylene alkyl ethers such as polyoxyethylene lauryl ether, polyoxyethylene cetyl ether, polyoxyethylene stearyl ether, polyoxyethylene oleyl ether, and polyoxyethylene higher alcohol ether; polyoxyethylene alkyl aryl ethers such as polyoxyethylene nonyl phenyl ether; polyoxyethylene derivatives; sorbitan fatty acid esters such as sorbitan monolaurate, sorbitan monopalmitate, sorbitan monostearate, sorbitan tristearate, sorbitan monooleate, sorbitan trioleate, sorbitan sesquioleate, and sorbitan distearate; polyoxyethylene sorbitan fatty acid esters such as polyoxyethylene sorbitan monolaurate, polyoxyethylene sorbitan monolaurate, polyoxyethylene sorbitan monopalmitate, polyoxyethylene sorbitan monostearate, polyoxyethylene sorbitan tristearate, polyoxyethylene sorbitan monooleate, and polyoxyethylene sorbitan trioleate; polyoxyethylene sorbitol fatty acid ester such as polyoxyethylene sorbitol tetraoleate; glycerin fatty acid esters such as glycerol monostearate, glycerol monooleate, and self-emulsifying glycerol monostearate; polyoxyethylene fatty acid esters such as polyethylene glycol monolaurate, polyethylene glycol monostearate, polyethylene glycol distearate, and polyethylene glycol monooleate; polyoxyethylene alkylamine; polyoxyethylene hydrogenated castor oil; and alkyl alkanol amide.

Examples of the cationic surfactants and the amphoteric surfactants include alkyl amine salts such as coconut amine acetate and stearylamine acetate; quaternary ammonium salts such as lauryl trimethyl ammonium chloride, stearyl trimethyl ammonium chlorite, cetyl trimethyl ammonium chloride, distearyl dimethyl ammonium chloride, and alkyl benzyl dimethyl ammonium chlorides; alkyl betaines such as lauryl betaine, stearyl betaine, and lauryl carboxymethyl hydroxyethyl imidazolinium betaine; and amine oxides such as lauryl dimethyl amine oxide. Use of a cationic surfactant also makes it possible to impart antibacterial property to a resulting hydrophilic polymer.

Another example of the surfactant in the present invention is a fluorine-based surfactant. With use of a fluorine-based surfactant, it is also possible to impart antibacterial property. Examples of the fluorine-based surfactant include various surfactants, one of which is a fluorine-based surfactant obtained by replacing hydrogen of a lipophilic group of a general surfactant with fluorine to obtain a perfluoro alkyl group. Such a fluorine-based surfactant makes it possible to significantly enhance surface activity.

There are four kinds of the foregoing fluorine-based surfactant which have respective different hydrophilic groups: anionic fluorine-based surfactant, nonionic fluorine-based surfactant, cationic fluorine-based surfactant, and amphoteric fluorine-based surfactant. In many cases, their lipophilic groups are fluorocarbon chains of the same structure. Furthermore, a carbon chain, which is a lipophilic group, can either be a linear chain or a branched chain.

Representative examples of the fluorine-based surfactant include the following surfactants.

Representative examples of the fluorine-based surfactant include fluoroalkyl ($C_2$-$C_{10}$) carboxylic acids, disodium N-perfluorooctane sulfonyl glutamate, sodium 3-[fluoroalkyl ($C_6$-$C_{11}$) oxy]-1-alkyl ($C_3$-$C_4$) sulfonates, sodium 3-[ω-fluoroalkanoyl ($C_6$-$C_8$)—N-ethylamino]-1-propanesulfonates, N-[3-(perfluorooctanesulfonamide) propyl]-N, N-dimethyl-N-carboxymethylene ammonium betaine, fluoroalkyl ($C_{11}$-$C_{20}$) carboxylic acids, perfluoroalkyl carboxylic acids ($C_7$-$C_{13}$), perfluorooctanesulfonic acid diethanolamide, perfluoroalkyl ($C_4$-$C_{12}$) sulfonates (Li, K, Na), N-propyl-N-(2-hydroxyethyl)perfluorooctanesulfonamide, perfluoroalkyl ($C_6$-$C_{10}$) sulphonamidopropyl trimethyl ammonium salts, perfluoroalkyl ($C_6$-$C_{10}$)—N-ethylsulfonylglycine salts (K), bis(N-perfluorooctylsulfonyl-N-ethylaminoethyl) phosphate, monoperfluoroalkyl ($C_6$-$C_{16}$) ethyl phosphates, perfluoroalkyl quaternary ammonium iodide (trade name: Fluorad FC-135, cationic fluorine-based surfactant manufactured by Sumitomo 3M Ltd.), perfluoroalkyl alkoxylate (trade name: Fluorad FC-171, nonionic surfactant manufactured by Sumitomo 3M Ltd.), and potassium salts of perfluoroalkylsulfonic acid (trade name: Fluorad FC-95 and FC-98, anionic surfactants manufactured by Sumitomo 3M Ltd.).

In the present invention, an organometallic surfactant can be used as well. An organometallic surfactant used in the present invention contains, in a main chain or side chain of its molecule, a metal such as Si, Ti, Sn, Zr, and Ge. The organometallic surfactant preferably contains Si in the main chain of its molecule. The organometallic surfactant is more preferably a siloxane-based surfactant. Representative examples of the organometallic surfactant include surfactants mentioned at page 34 of Yoshida, Kondo, Ogaki, and Yamanaka's "Shinban: Kaimenkasseizai handobukku" (New edition: Surfactant Handbook) published by Kogaku Tosho in 1966.

The surfactant for use in the present invention is not limited to the above surfactants. The surfactant is, among the above surfactants, preferably a nonionic surfactant, particularly preferably sorbitan fatty acid ester or polyoxyethylene sorbitan fatty acid ester, in terms of safety.

A method of adding a surfactant is, for example, a method by which, in any of the steps of a process for producing a water-absorbing resin or water-absorbing agent, a surfactant is added once or twice or more times. Specifically, the surfactant can be added in any of the following production steps: monomer preparation, polymerization, gel-crushing (optional), drying, pulverizing after drying, classification, surface-crosslinking, fine powder recovery, sizing, granulation, and the like. Preferably, a surfactant may be used, when polymerization is carried out, to thereby control foaming polymerization. Alternatively, a surfactant may be used, when gel-crushing is carried out, to thereby accelerate gel-crushing and enhance gel flowability. A more preferred method is a method by which a surfactant is added to a water-absorbing resin or water-absorbing agent after polymerization and after drying. A surfactant as-is may be added in any step, or may be dissolved in a liquid (or water) to obtain a solution (or an aqueous solution) or dispersed into water to obtain an aqueous dispersion and then the solution or dispersion may be added. A surfactant or its solution alone may be added in any step, or a surfactant or its solution may be added together with some other additive discussed earlier. In a case where a plurality of additives are added, such additives may be dissolved in a liquid to obtain a single solution or may be mixed together and then the solution or the mixture may be added. Alternatively, the additives may be added separately from each other. In a case where a plurality of additives are added, the order in which the additives are added is not particularly limited.

In a case where a surfactant is added, the amount of the surfactant used (added) is, from the viewpoint of ensuring, for example, flowability in a dry state and in a moistened state, preferably more than 0 parts by weight and 0.2 parts by weight or less, more preferably 0.0001 parts by weight to 0.2 parts by weight, even more preferably 0.0005 parts by weight to 0.1 parts by weight, particularly preferably 0.001 parts by weight to 0.05 parts by weight, most preferably 0.001 parts by weight to 0.01 parts by weight, relative to 100 parts by weight of the water-absorbing resin. By adding the surfactant to a water-absorbing resin or water-absorbing agent in an amount that falls within the above range, and by further adding the surfactant to the water-absorbing resin powder after drying, it is easy to control the K-index, moisture absorption blocking ratio, and the like to fall within desired ranges. When the amount of the surfactant added is more than 0.2 parts by weight, the surface tension of an absorbed liquid decreases, and the resulting effect may not be worth the amount added. This is uneconomical.

(3. Hydrophilic Polymer Compound)

A water-absorbing agent in accordance with the present invention may contain a hydrophilic polymer compound (which is other than water-absorbing resin and a soluble polymer obtained therefrom).

The term "hydrophilic polymer compound" in the present invention refers to a polymer compound that dissolves in 100 g of water having a temperature of 25° C. in an amount of 1 g or more. The scope of the meaning of the term "hydrophilic polymer compound" in the present invention includes: compounds which have a lower molecular weight than that of generally known polymers and in which the number of repeating units is 100 or less (so-called oligomers); and compounds containing, in its molecule, a group having repeating units. The term "hydrophilic polymer compound" is used to mean any of a group of compounds whose molecular weight is a certain number or greater (more preferably, a certain number or greater and a certain number or less).

The lower limit of the molecular weight of the hydrophilic polymer compound is preferably 200 or more, more preferably 300 or more, even more preferably 400 or more. The upper limit of the molecular weight of the hydrophilic polymer compound is preferably 10000 or less, more preferably 5000 or less, even more preferably 1000 or less. The number of repeating units is not particularly limited, provided that the molecular weight falls within the above range.

With regard to the structure of the hydrophilic polymer compound, the hydrophilic polymer compound may have a linear chain and/or a branched chain. From the viewpoint of, for example, ensuring water-absorption property and flowability, the hydrophilic polymer compound more preferably has a linear chain structure. The hydrophilic polymer compound even more preferably has a structure in which repeating units are ethoxyl groups (—$CH_2$—$CH_2$—O—) or propoxyl groups (—$CH_2$—$CH_2$—$CH_2$—O—), particularly preferably has a structure in which repeating units are ethoxyl groups (—$CH_2$—$CH_2$—O—). It is more preferable that such a structure forms a main chain, and particularly preferable that the structure occupies 70 weight % or more of the hydrophilic polymer compound.

The hydrophilic polymer compound is preferably a compound that has a certain melting point or lower. The melting point is preferably 100° C. or lower, more preferably 70° C.

or lower, even more preferably 50° C. or lower, particularly preferably 30° C. or lower. A melting point in the above described range is preferable because the effect of the present invention can be advantageously brought about and it becomes easy to handle the hydrophilic polymer compound.

The hydrophilic polymer compound can be any of cationic, anionic, and nonionic compounds, and is preferably a nonionic compound. Specifically, examples of the hydrophilic polymer compound include polyvinyl alcohol, polyethylene oxide, polyethylene glycol, polypropylene glycol, polyacrylamide, polyacrylic acid, sodium polyacrylate, polyvinylamine, polyethyleneimine, methyl cellulose, carboxymethyl cellulose, hydroxyethyl cellulose, hydroxypropyl cellulose, dextrin, sodium alginate, and starch. Among these, polyethylene glycol and polypropylene glycol are preferred. Polyethylene glycol is particularly preferred.

The hydrophilic polymer may be modified (e.g., alkyl-modified, ether-modified, carboxylalkyl-modified) if needed. Note, however, that the hydrophilic polymer compound is more preferably unmodified. For example, polyethylene glycol may be a derivative such as methoxypolyethylene glycol but is more preferably unmodified polyethylene glycol.

In a case where the hydrophilic polymer compound is added, the amount of the hydrophilic polymer compound used (added) is, from the view point of ensuring, for example, flowability in a dry state and in a moistened state, preferably 1.0 part by weight or less, more preferably 0.1 parts by weight or less, even more preferably 0.05 parts by weight or less, particularly preferably 0.01 parts by weight or less, most preferably 0.005 parts by weight or less, relative to 100 parts by weight of the water-absorbing resin. The amount of the hydrophilic polymer compound used (added) is preferably 0.0001 parts by weight or more, more preferably 0.0005 parts by weight or more, particularly preferably 0.001 parts by weight or more, relative to 100 parts by weight of the water-absorbing resin. When the amount of the hydrophilic polymer compound added falls within the above range, the K-index, moisture absorption blocking ratio, and the like are easily controlled to fall within desired ranges.

A method of adding a hydrophilic polymer compound to a water-absorbing resin or water-absorbing agent is, for example, a method by which, in any step of a process for producing the water-absorbing resin or water-absorbing agent, a hydrophilic polymer compound is added once or twice or more times. Specifically, the hydrophilic polymer compound can be added in any of the following production steps: monomer preparation, polymerization, gel-crushing (optional), drying, pulverizing after drying, classification, surface-crosslinking, fine powder recovery, sizing, granulation, and the like. A hydrophilic polymer compound may be used as a component for graft polymerization to obtain a water-absorbing resin, and may be used to accelerate gel-crushing. A more preferred method is, for example, a method by which a hydrophilic polymer compound is added to a water-absorbing resin after polymerization and after drying. A hydrophilic polymer compound as-is may be added in any step, or may be dissolved in a liquid (or water) to obtain a solution (or an aqueous solution) or dispersed into water to obtain an aqueous dispersion and then the solution or dispersion may be added. A hydrophilic polymer compound or its solution alone may be added in any step, or a hydrophilic polymer compound or its solution may be added together with some other additive discussed earlier. In a case where a plurality of additives are added, such additives may be dissolved in a liquid to obtain a single solution or may be mixed together and then added and then the solution or the mixture may be added. Alternatively, the additives may be added separately from each other. In a case where a plurality of additives are added, the order in which the additives are added is not particularly limited.

(4. Cationic Polymer)

A cationic polymer suitably usable in Embodiment 1 may be, specifically, any of compounds disclosed in International Publication No. 2011/040530, and may be used in any of the amounts disclosed therein.

(5. Chelating Agent)

A chelating agent suitably usable in Embodiment 1 may be, specifically, any of compounds disclosed under "[2] Chelating Agent" of International Publication No. 2011/040530, and may be used in any of the amounts disclosed thereunder. The addition of a chelating agent makes it possible to, for example, prevent coloration and deterioration of the water-absorbing agent.

(6. Inorganic Reducing Agent)

An inorganic reducing agent suitably usable in Embodiment 1 may be, specifically, any of compounds disclosed under "[3] Inorganic reducing agent" of International Publication No. WO 2011/040530 and may be used in any of the amounts disclosed thereunder. The addition of an inorganic reducing agent makes it possible, for example, to prevent coloration of the water-absorbing agent, to reduce the amount of residual monomers, and to prevent deterioration of the water-absorbing agent.

(7. Hydroxycarboxylic Acid Compound)

A hydroxycarboxylic acid compound suitably usable in Embodiment 1 is, for example, a carboxylic acid containing a hydroxyl group in its molecule or a salt of the carboxylic acid. An example of such a hydroxycarboxylic acid compound is a hydroxy-carboxylic acid containing a hydroxyl group at its alpha position, e.g., lactic acid, citric acid, or the like. Specifically, the hydroxycarboxylic acid compound may be any of compounds disclosed under "[6] α-hydroxycarboxylic acid compound" of International Publication No. WO 2011/040530, and may be used in any of the amounts disclosed thereunder. The addition of a hydroxycarboxylic acid compound makes it possible to, for example, prevent coloration of the water-absorbing agent.

(8. Other Additive)

For the purpose of imparting various functions to a water-absorbing resin, a commonly-used additive(s) other than the foregoing additives may be added. Examples of the commonly-used additive include: compounds having a phosphorus atom; oxidizers; organic reducing agents; organic powder such as metallic soap; deodorant agents; antibacterial agent; pulp; and thermoplastic fibers.

The amount of the commonly-used additive(s) used (added) is determined appropriately according to its purpose of use, and therefore is not particularly limited. The total amount of the commonly-used additive(s) used (added) is preferably 3 parts by weight or less, more preferably 1 part by weight or less, relative to 100 parts by weight of the water-absorbing resin powder. The commonly-used additive(s) may be mixed with a water-absorbing resin in any step that is different from the step in which the foregoing additive(s) is/are added.

(1-2-12) Shape of Water-Absorbing Agent

In general, a water-absorbing agent is not particularly limited as to its form, provided that the foregoing conditions (a) K-index$\geq$70 and (b) moisture absorption blocking ratio$\leq$70 weight % are satisfied, and may be, for example, in the form of fibers or a gel. The water-absorbing agent is preferably in the form of particles (also called: in the form of powder), and more preferably in the form of particles having any of the particle size distributions described later. Examples of the shape of such a particulate water-absorbing agent include: spherical and/or ellipsoidal primary particles and sausage-shaped primary particles which are obtained by reversed phase suspension polymerization disclosed in FIGS. 1 and 2 of U.S. Pat. No. 5,244,735; granulated versions of spherical and/or ellipsoidal primary particles, such as particles agglomerated together, e.g., agglomerated beads as disclosed in FIG. 1 on page 75 of NON WOVENS WORLD October-November 2000 (published by Marketing Technology Service, Inc.); and non-uniformly pulverized shape derived from crushing a hydrogel polymer obtained via polymerization of an aqueous monomer solution, such as crystals disclosed in FIGS. 2, 3, and 4 of U.S. Pat. No. 5,981,070 and FIG. 1 on page 75 of the foregoing NON WOVENS WORLD October-November 2000, and granulated versions thereof.

A water-absorbing agent in Embodiment 1 is preferably a particulate water-absorbing agent which is in the form other than the form of spherical primary particles. The water-absorbing agent in Embodiment 1 is more preferably in the form other than the form of oval spherical (ellipsoidal) primary particles, even more preferably in the form of particles having a non-uniformly pulverized shape derived from granulating spherical particles and ellipsoidal particles. Alternatively, the water-absorbing agent is even more preferably in the form of particles having a non-uniformly pulverized shape derived from crushing a hydrogel polymer obtained via polymerization of an aqueous monomer solution (i.e., in the form of particles having a non-uniformly pulverized shape) or in the form of a granulated version thereof. The water-absorbing agent is particularly preferably in the form of particles having a non-uniformly pulverized shape or in the form of a granulated version thereof.

The particulate water-absorbing agent is preferably in the form other than the form of spherical primary particles and/or other than the form of ellipsoidal primary particles, because, when an absorbent article or the like is produced using such a particulate water-absorbing agent, the particulate water-absorbing agent can be well mixed with a fiber material such as pulp and does not easily fall off an absorbent body which is a mixture of the water-absorbing agent and the fiber material. As such, when a water-absorbing agent in the form other than the form of spherical primary particles and/or other than the form of ellipsoidal primary particles is used, the water-absorbing agent can be uniformly distributed within the absorbent body.

(1-2-13) Powder Properties of Water-Absorbing Agent

It is preferable that a water-absorbing agent in Embodiment 1 has a small coefficient of internal friction or a small angle of internal friction and thereby has a small angle of repose. The water-absorbing agent in Embodiment 1 also has a small moisture absorption blocking ratio. The water-absorbing agent, therefore, is poor in adhesion, is in a powder form, and shows excellent flowability both in a dry state (in which a moisture content is 0 weight % to 20 weight % or in which a moisture content is 0 weight % to 10 weight %) and in a moistened state. The coefficient of internal friction and the angle of internal friction can be found by a shear test on particle layers. The shear test on powder can be carried out with use of an apparatus such as a shear-box apparatus, a ring-shear apparatus, or a parallel-plate apparatus, examples of which include a Jenike Shear Cell.

It is generally known that spherical primary particles and/or ellipsoidal primary particles obtained by a reversed phase suspension polymerization have high flowability. On the other hand, even in cases of particles having "non-uniform" shape (i.e., particles having a shape that is not spherical primary particles and that is not oval spherical primary particles) (e.g., particles having non-uniformly pulverized shape produced by an aqueous solution polymerization or particles obtained by, after a reversed phase suspension polymerization, granulating the obtained spherical primary particles and/or ellipsoidal primary particles), the powder flowability of such particles is such that, due to their non-uniform shape, the coefficient of internal friction is high and flowability is very low.

Therefore, the above water-absorbing agent composed of particles having a high coefficient of internal friction incurs increases in transport resistance during air flow conveyance, transport resistance during conveyance using a paddle-type conveyor, and transport resistance during conveyance using a screw-type conveyor. That is, according to conventional techniques, when handling particles having a "non-uniform" shape (i.e., shape other than spherical primary particles and other than oval spherical primary particles), a production apparatus and a conveyor are clogged with such a water-absorbing agent, thus causing excessive load and resulting in frequent halts of these apparatuses.

Furthermore, conventionally, addition of inorganic fine particles such as water-insoluble powder to a water-absorbing agent is generally carried out in order to ensure flowability in a moistened environment. A water-absorbing agent having such inorganic fine particles added thereto is poor in flowability in a dry state, particularly in a dry state in which a moisture content is 0 weight % to 20 weight %. This results in increases in frequency of clogging of the production apparatus and conveyor with the water-absorbing agent and frequency of halts of such apparatuses due to excessive load.

However, the water-absorbing agent in Embodiment 1, whose K-index and moisture absorption blocking ratio are controlled to fall within the foregoing specific ranges, shows very high powder flowability in a tightly packed state, even when the water-absorbing agent has a shape other than the shape of spherical primary particles and other than the shape of oval spherical primary particles.

As such, the water-absorbing agent in Embodiment 1 has both improved moisture absorption flowability and improved powder flowability, and also achieves very high flowability. The water-absorbing agent in Embodiment 1 also shows high powder flowability when in its dry state, and therefore makes it possible to alleviate mechanical damage and thereby prevent or reduce reductions in fluid retention capacity under pressure and moisture absorption flowability which would result from mechanical damage.

As such, the water-absorbing agent in Embodiment 1 has high powder flowability as described above. Therefore, use of the water-absorbing agent is effective in simplification of a hopper, a powder storage tank, and the like for use in, for example, a process for producing an absorbent body or the like.

[1-3] Method for Producing Water-Absorbing Agent

In the present invention, it was found that a water-absorbing agent satisfying the conditions (a) K-index≥70 and (b) moisture absorption blocking ratio≤70 weight % attains the foregoing object. In order to obtain a water-absorbing agent in accordance with the present invention, it is important to prepare the water-absorbing agent so that the novel parameters, K-index and moisture absorption blocking ratio, satisfy the conditions (a) K-index≥70 and (b) moisture absorption blocking ratio≤70 weight %. A method for producing a water-absorbing agent in accordance with the present invention is not particularly limited. The water-absorbing agent is preferably produced by a later-described technique so that the water-absorbing agent, which contains a water-absorbing resin as a main component, satisfies the conditions (a) K-index≥70 and (b) moisture absorption blocking ratio≤70 weight %.

(a) K-index is 70 or more.

(b) Moisture absorption blocking ratio, after 30 minutes of standing at a temperature of 25° C. and a relative humidity of 80% RH, is 70 weight % or less.

As used herein, the "K-index" is defined by the following correlation equation:

$$K\text{-index}=100-(-438+3.6\times\text{angle of repose}+3.5\times\text{angle of difference}+7.9\times\text{compressibility rate}+290\times\text{bulk density (EDANA method)}).$$

The water-absorbing agent in accordance with the present invention is produced by, for example, a technique by which the moisture content and particle size distribution of the water-absorbing agent are controlled and/or by a technique by which the amount of an additive(s) (optional) and when the additive(s) (optional) is/are added are controlled. Alternatively, two or more water-absorbing resins may be mixed (especially dry-blended) to thereby prepare a water-absorbing agent satisfying the above conditions (a) and (b). For example, two water-absorbing resins having respective different shapes, obtained by respective totally different production methods such as reversed phase suspension polymerization and aqueous solution polymerization, may be mixed to obtain a water-absorbing agent in accordance with the present invention.

The following description will discuss production steps (1-3-1) to (1-3-8) for producing a water-absorbing agent in accordance with Embodiment 1.

(1-3-1) Step of Preparing Aqueous Monomer Solution

This step is a step of preparing an aqueous solution containing a monomer (e.g., an acrylic acid (salt)) as a main component (this solution is hereinafter referred to as an "aqueous monomer solution"). It is also possible to use a monomer slurry liquid, provided that a water-absorbing resin to be produced will not have degraded water absorption performance. For convenience of description, however, this section describes an aqueous monomer solution.

The term "main component" means monomer (e.g., acrylic acid (salt)) that occupies usually 50 mol % or more, preferably 70 mol % or more, more preferably 90 mol % or more (with an upper limit value of 100 mol %) relative to the total amount of monomers used for a polymerization reaction of a water-absorbing resin (excluding an internal crosslinking agent).

(1. Acrylic Acid)

In Embodiment 1, it is preferable that an acrylic acid and/or an acrylic acid salt (hereinafter referred to as "acrylic acid (salt)") is used as a monomer from the viewpoint of physical properties of a water-absorbing agent to be produced and productivity.

The "acrylic acid" may be a known acrylic acid, and may contain, as a polymerization inhibitor, preferably a methoxyphenol, more preferably p-methoxyphenol. The "acrylic acid" only needs to be contained in an amount of preferably 200 ppm or less, more preferably 10 ppm to 160 ppm, even more preferably 20 ppm to 100 ppm, from the viewpoint of polymerizability of the acrylic acid and the color of a water-absorbing agent to be produced. An impurity in the acrylic acid, in Embodiment 1, may be any of compounds disclosed in U.S. Patent Application Publication No. 2008/0161512.

The "acrylic acid (salt)" is produced by neutralizing the above acrylic acid with a basic composition below. The acrylic acid (salt) may be a commercially available acrylic acid (salt) (for example, sodium acrylate) or may be produced by neutralizing an acrylic acid in a plant for producing a water-absorbing agent.

(2. Basic Composition)

In Embodiment 1, the term "basic composition" refers to a composition containing a basic compound, such as a commercially available aqueous sodium hydroxide solution.

Specific examples of the basic compound include carbonates or bicarbonates of alkali metals, hydroxides of alkali metals, ammonia, and organic amines. Among these, the basic compound preferably has strong basicity from the viewpoint of physical properties of a water-absorbing agent to be obtained. That is, the basic compound is preferably a hydroxide of an alkali metal, such as sodium hydroxide, potassium hydroxide, or lithium hydroxide, and is more preferably sodium hydroxide.

(3. Neutralization)

In Embodiment 1, neutralization can be neutralization of an acrylic acid (before polymerization), neutralization of a crosslinked hydrogel polymer obtained by crosslinking and polymerizing an acrylic acid (after polymerization) (hereinafter referred to as "later neutralization"), or a combination of the neutralization of an acrylic acid and the neutralization of a crosslinked hydrogel polymer obtained by crosslinking and polymerizing an acrylic acid. These neutralizations are not limited to any particular type, and can be of a continuous type or a batch type. Among these, a continuous type is preferable from the viewpoint of production efficiency and the like.

Note that with regard to conditions such as a neutralization apparatus, a neutralization temperature, and a retention time, the conditions disclosed in International Publication No. 2009/123197 and U.S. Patent Application Publication No. 2008/0194863 can be applied to Embodiment 1.

A neutralization rate in Embodiment 1 is preferably 10 mol % to 90 mol %, more preferably 40 mol % to 85 mol %, even more preferably 50 mol % to 80 mol %, and particularly preferably 60 mol % to 75 mol %, relative to monomers' acid groups. At a neutralization rate of less than 10 mol %, a fluid retention capacity may be lowered significantly. On the contrary, in a case where the neutralization rate is higher than 90 mol %, it may not be possible to obtain a water-absorbing resin having a high fluid retention capacity under pressure.

The neutralization rate also applies to the later neutralization. The neutralization rate can also apply to a neutralization rate for a water-absorbing agent which is an end product. Note that a neutralization rate of 75 mol % means a mixture of 25 mol % of an acrylic acid and 75 mol % of an acrylic acid salt. The mixture is referred to also as a partially neutralized acrylic acid.

(4. Other Monomer(s))

In Embodiment 1, "other monomer(s)" refers to a monomer(s) other than the acrylic acid (salt), and a water-absorbing agent can be produced by using the other monomer(s) in combination with the acrylic acid (salt).

Examples of the other monomer(s) include unsaturated monomers which are water-soluble or hydrophobic. Specifically, any of compounds disclosed in U.S. Patent Application Publication No. 2005/0215734 (except an acrylic acid) can be used in Embodiment 1.

(5. Internal Crosslinking Agent)

An internal crosslinking agent for use in Embodiment 1 may be any of compounds disclosed in U.S. Pat. No. 6,241,928. One of the compounds or two or more of the compounds is/are selected in view of reactivity.

From the viewpoint of, for example, the water absorption performance of a water-absorbing resin to be produced, the internal crosslinking agent is preferably a compound having two or more polymerizable unsaturated groups, more preferably a compound that is pyrolytic at a drying temperature below, even more preferably a compound having a (poly) alkylene glycol structural unit and two or more polymerizable unsaturated groups.

The polymerizable unsaturated groups are preferably an allyl group or a (meth)acrylate group, more preferably a (meth)acrylate group. The (poly)alkylene glycol structural unit is preferably polyethylene glycol. The number of alkylene glycol units in the (poly)alkylene glycol is preferably 1 to 100, more preferably 6 to 50.

Therefore, in Embodiment 1, preferably (poly)alkylene glycol di(meth)acrylate or (poly)alkylene glycol tri(meth) acrylate is used, and more preferably (poly)ethylene glycol di(meth)acrylate is used.

The internal crosslinking agent is used in an amount of preferably 0.0001 mol % to 10 mol %, more preferably 0.001 mol % to 1 mol % relative to the total amount of monomers. In a case where the amount used falls within the above ranges, a desired water-absorbing resin can be obtained. Note that in a case where the amount used is excessively small, gel strength tends to be lowered and consequently there tends to be an increase in water-soluble content. In a case where the used amount is excessively large, fluid retention capacity tends to be lowered. Therefore, the amount used that is excessively large or excessively small is not preferable.

In Embodiment 1, the following method is preferably used: An aqueous monomer solution to which a certain amount of internal crosslinking agent has been added in advance is prepared. Then, the aqueous monomer solution is simultaneously subjected to polymerization and to a crosslinking reaction. Alternatively, other than the above method, examples of a possible method include a method in which an internal crosslinking agent is added during or after the polymerization so that postcrosslinking is carried out, a method in which radical crosslinking is carried out with use of a radical polymerization initiator, and a method in which radiation crosslinking is carried out with use of active energy rays such as an electron ray and an ultraviolet ray. Alternatively, these methods may be used in combination.

(6. Other Substances Added to Aqueous Monomer Solution)

Embodiment 1 may include adding any substance below to the aqueous monomer solution during the preparation thereof from the viewpoint of improved physical properties for a water-absorbing resin to be produced.

Specific examples of such a substance include hydrophilic polymers such as starch, starch derivatives, cellulose, cellulose derivatives, polyvinyl alcohol, polyacrylic acids (salts), and crosslinked polyacrylic acids (salts). Any of such substances can be contained in an amount of preferably 50 weight % or less, more preferably 20 weight % or less, even more preferably 10 weight % or less, particularly preferably 5 weight % or less (with a lower limit value of 0 weight %). Alternatively, a carbonate, an azo compound, a foaming agent such as gas bubbles or the like, a surfactant, a chelating agent, a chain transfer agent, and/or the like may be added. Any of such substances can be contained in an amount of preferably 5 weight % or less, more preferably 1 weight % or less, even more preferably 0.5 weight % or less (with a lower limit value of 0 weight %).

The above substances are not necessarily added to the aqueous monomer solution, but can be added during the polymerization, or can be added both to the aqueous monomer solution and during the polymerization.

In a case where a water-soluble resin or a water-absorbing resin is used as the hydrophilic polymer, a graft polymer or a water-absorbing resin composition (for example, an starch-acrylic acid polymer or a PVA-acrylic acid polymer) can be obtained. These polymers and water-absorbing resin compositions are also encompassed in the scope of Embodiment 1.

(7. Monomer Component Concentration)

The above various substances are added when an aqueous monomer solution is prepared during the step of preparing an aqueous monomer solution. The aqueous monomer solution may contain a monomer component at any concentration. The concentration is preferably 10 weight % to 80 weight %, more preferably 20 weight % to 75 weight %, even more preferably 30 weight % to 70 weight %, from the viewpoint of physical properties of a water-absorbing resin.

In a case where aqueous solution polymerization or reversed phase suspension polymerization is employed, a solvent other than water can be used in combination with water as necessary. In such a case, the type of the solvent used is not limited to any particular one.

The "monomer component concentration" is a value obtained using Equation (1) below. The weight of the aqueous monomer solution does not include the weight of a graft component, water-absorbing resin, or a hydrophobic solvent used in reversed phase suspension polymerization.

$$\text{(Monomer component concentration (weight \%))} = \text{(weight of monomer component)/(weight of aqueous monomer solution)} \times 100 \quad (1).$$

(1-3-2) Polymerization Step

A polymerization step is a step of polymerizing an aqueous acrylic acid (salt)-based monomer solution obtained in the step of preparing an aqueous monomer solution to obtain a hydrogel polymer.

(1. Polymerization Initiator)

The polymerization initiator for use in Embodiment 1 is selected as appropriate in accordance with a form of polymerization or the like and is not limited to any particular one. Examples of the polymerization initiator include pyrolysis-type polymerization initiators, photolysis-type polymerization initiators, redox-type polymerization initiators containing a reducing agent for facilitating decomposition of any of those polymerization initiators. Specifically, used as the polymerization initiator is one of the polymerization initiators disclosed in U.S. Pat. No. 7,265,190, or two or more of the polymerization initiators disclosed in U.S. Pat. No. 7,265,190. Further, the polymerization initiator is preferably a peroxide or an azo compound, more preferably a peroxide, even more preferably a persulfate, from the viewpoint of the handleability of the polymerization initiator and the physical properties of the water-absorbing agent or the water-absorbing resin.

The amount of the polymerization initiator used is preferably 0.001 mol % to 1 mol %, more preferably 0.001 mol % to 0.5 mol %, relative to the amount of monomers. The amount of the reducing agent used is preferably 0.0001 mol % to 0.02 mol %, relative to the amount of monomers.

A polymerization reaction can be carried out by, instead of using the polymerization initiator, irradiating a monomer with an active energy ray such as a radial ray, an electron ray, or an ultraviolet ray. Alternatively, any of these active energy rays can be used in combination with a polymerization initiator.

(2. Form of Polymerization)

Polymerization to be applied to Embodiment 1 is not limited to any particular form. From the viewpoint of a water absorbent property, ease of control of polymerization, and the like, preferable examples of the polymerization include spray droplet polymerization, aqueous solution polymerization, and reversed phase suspension polymerization, more preferable examples of the polymerization include aqueous solution polymerization and reverse phase suspension polymerization, and even more preferable examples of the polymerization include aqueous solution polymerization. Among these, continuous aqueous solution polymerization is particularly preferable. The continuous aqueous solution polymerization can be any one of continuous belt polymerization and continuous kneader polymerization.

Specific examples of the form of continuous belt polymerization include those disclosed in U.S. Pat. Nos. 4,893,999, 6,241,928, and U.S. Patent Application Publication No. 2005/0215734. Specific examples of the form of continuous kneader polymerization include those disclosed in U.S. Pat. Nos. 6,987,151 and 6,710,141. In a case where these forms of continuous aqueous solution polymerization are employed, it is possible to improve efficiency with which a water-absorbing resin is produced.

Preferable examples of the form of the continuous aqueous solution polymerization include "high-temperature-initiating polymerization" and "high-concentration polymerization". The "high-temperature-initiating polymerization" is a form of polymerization in which polymerization is started while a temperature of an aqueous monomer solution is preferably 30° C. or higher, more preferably 35° C. or higher, even more preferably 40° C. or higher, and particularly preferably 50° C. or higher (upper limit value: boiling point). The "high-concentration polymerization" is a form of polymerization in which polymerization is carried out while a monomer concentration is preferably 30 weight % or more, more preferably 35 weight % or more, even more preferably 40 weight % or more, and particularly preferably 45 weight % or more (upper limit value: saturated concentration). Alternatively, it is possible to use these forms of polymerization in combination.

In Embodiment 1, polymerization can be carried out in an air atmosphere. From the viewpoint of color of a water-absorbing resin to be obtained, polymerization is carried out preferably in an atmosphere of an inert gas such as nitrogen or argon. In the case where polymerization is carried out in an atmosphere of an inert gas such as nitrogen or argon, an oxygen concentration is preferably controlled to be, for example, 1 volume % or less. Note that dissolved oxygen in an aqueous monomer solution is also preferably substituted with an inert gas (e.g., dissolved oxygen: less than 1 mg/l).

In Embodiment 1, alternatively, it is possible to carry out foaming polymerization in which polymerization is carried out while gas bubbles (particularly the inert gas or the like) are dispersed into an aqueous monomer solution.

In Embodiment 1, alternatively, it is possible to increase solid content concentration during polymerization. The degree of increase in solid content, as an index of an increase in such a solid content concentration, is defined by the following Equation (2). Note that the degree of increase in solid content concentration is preferably 1 weight % or more, more preferably 2 weight % or more.

(Degree of increase in solid content (weight %))=
(solid content concentration in polymer in the
form of hydrogel after polymerization (weight
%))−(solid content concentration in aqueous
monomer solution (weight %)),    Equation 2:

where the solid content concentration in an aqueous monomer solution is a value obtained by the following Equation (3) and where components in a polymerization system are an aqueous monomer solution, a graft component, a water-absorbing resin and other solid matters (e.g., water-insoluble fine particles and the like), and therefore exclude a hydrophobic solvent in reverse phase suspension polymerization.

(Solid content concentration in aqueous monomer
solution (weight %))={weight of (monomer
component+graft component+water-absorbing
resin+other solid matters)}/(weight of compo-
nents in polymerization system)×100    Equation (3):

(1-3-3) Gel-Crushing Step

A gel-crushing step is a step of gel-crushing a hydrogel polymer, which has been obtained by the polymerization step, with use of, for example, a kneader, a screw extruder such as a meat chopper, or a gel-crusher such as a cutter mill to obtain a hydrogel polymer in the form of particles. In a case where the polymerization step is carried out through kneader polymerization, such a step is equivalent to a combination of the polymerization step and the gel-crushing step which are carried out simultaneously. In a case where a hydrogel polymer in the form of particles is directly obtained through a polymerization process such as vapor phase polymerization or reverse phase suspension polymerization, the gel-crushing step may not be carried out.

With regard to gel-crushing conditions and forms other than above described, any of conditions and forms disclosed in International Publication No. WO 2011/126079 are preferably employed in Embodiment 1.

(1-3-4) Drying Step

A drying step is a step of drying the hydrogel polymer in the form of particles, which has been obtained by the polymerization step and/or the gel-crushing step, until a desired resin solid content is attained, so as to obtain a dried polymer. The resin solid content is calculated from drying loss (a change in weight after heating 1 g of the water-absorbing resin at 180° C. for three hours). The resin solid content is preferably 80 weight % or more, more preferably 85 weight % to 99 weight %, even more preferably 90 weight % to 98 weight %, particularly preferably 92 weight % to 97 weight %.

A drying method of drying the hydrogel polymer in the form of particles is not particularly limited. Examples of the drying method include thermal drying, hot air drying, drying under reduced pressure, fluidized bed drying, infrared drying, microwave drying, drum dryer drying, drying by azeotropic dehydration with a hydrophobic organic solvent, and high humidity drying by use of high temperature water vapor. The drying method is, among others, preferably hot air drying, more preferably band drying, in which hot air drying is performed on a through-flow belt, from the viewpoint of drying efficiency.

From the viewpoint of the color of a water-absorbing resin and drying efficiency, the hot air drying is performed at a drying temperature (temperature of hot air) of preferably 120° C. to 250° C., more preferably 150° C. to 200° C. Drying conditions other than the drying temperature (e.g., the air velocity of hot air and the drying time) can be set as appropriate in accordance with moisture content of the hydrogel polymer in the form of particles to be dried, total weight of the hydrogel polymer in the form of particles to be dried, and a desired resin solid content. In the case of band drying, the various conditions disclosed in, for example, International Publication No. 2006/100300, International Publication No. 2011/025012, International Publication No. 2011/025013, and International Publication No. 2011/111657 can be applied as necessary.

Setting the drying temperature, the drying time, and the like to be within these ranges makes it possible to obtain a water-absorbing resin whose CRC (fluid retention capacity), water-soluble content (Ext), and color are within desired ranges.

(1-3-5) Pulverizing Step and Classification Step

A pulverizing step and classification step are steps of pulverizing (pulverizing step) the dried polymer obtained in the drying step and adjusting (classification step) the particle size of a resulting pulverized polymer to have a particle size within a certain range so that a water-absorbing resin powder is obtained (for convenience, water-absorbing resin in a powder form before being subjected to surface crosslinking is referred to as "water-absorbing resin powder").

An apparatus used in the pulverizing step of Embodiment 1 can be, for example, a high-speed pulverizer such as a roll mill, a hammer mill, a screw mill, or a pin mill; a vibrating mill; a knuckle-type pulverizer; a cylindrical mixer; or the like. These apparatuses can be used in combination according to need.

A particle size adjusting method in the classification step of Embodiment 1 is not limited to a particular one and can be, for example, sieve classification with use of one or more JIS standard sieves (JIS Z8801-1 (2000)), airflow classification, or the like. Note that the particle size of water-absorbing resin is not limited to being adjusted during the pulverizing step and classification step, but may alternatively be adjusted as appropriate during the polymerization step (in particular, in reversed phase suspension polymerization or spray droplet polymerization) or some other step (for example, a granulation step or a fine powder recycling step).

(1-3-6) Surface-Crosslinking Step

A surface-crosslinking step is a step of forming a portion with a higher crosslinking density in a surface layer (that is, a portion, of the water-absorbing resin powder which is up to several tens of micrometers deep from the surface) of the water-absorbing resin powder produced through the above steps. This step includes a mixing substep, a heat treatment substep, and optionally a cooling substep.

In the surface-crosslinking step, a water-absorbing resin (water-absorbing resin particles) can be obtained which has been surface-crosslinked by radical crosslinking on the surface of the water-absorbing resin powder, surface polymerization on the surface of the water-absorbing resin powder, crosslinking reaction with a surface-crosslinking agent, or the like.

(1. Surface-Crosslinking Agent)

A surface-crosslinking agent used in Embodiment 1 is not limited to any particular one. Examples of the surface-crosslinking agent include organic surface-crosslinking agents and inorganic surface-crosslinking agents. Among others, an organic surface-crosslinking agent that is reactive with a carboxyl group is preferable, from the viewpoint of the physical properties of a water-absorbing resin and the handleability of the surface-crosslinking agent. For example, one of the surface-crosslinking agents disclosed in U.S. Pat. No. 7,183,456 can be used, or two or more of the surface-crosslinking agents disclosed in U.S. Pat. No. 7,183,456 can be used. Specifically, examples of the surface-crosslinking agent include: hydrophilic polymer compounds (such as ethylene glycol, diethylene glycol, and propylene glycol); epoxy compounds (such as ethylene glycol diglycidyl ether and polyethylene diglycidyl ether); haloepoxy compounds; polyamine compounds (such as ethylene diamine and diethylene triamine) or condensates of a polyamine compound and a haloepoxy compound; oxazoline compounds (such as 1,2-ethylenebisoxazoline and bisoxazoline); oxazolidinone compounds; polyvalent metal salts; alkylene carbonate compounds (such as ethylene carbonate); and cyclic urea compounds, and the like.

The amount of the surface-crosslinking agent used (or the total amount used in a case where a plurality of surface-crosslinking agents are used) is preferably 0.01 parts by weight to 10 parts by weight, more preferably 0.01 parts by weight to 5 parts by weight, relative to 100 parts by weight of the water-absorbing resin powder. The surface-crosslinking agent is preferably added as an aqueous solution. In such a case, the amount of water used is preferably 0.1 parts by weight to 20 parts by weight, more preferably 0.5 parts by weight to 10 parts by weight, relative to 100 parts by weight of the water-absorbing resin powder. In a case where a hydrophilic organic solvent is used according to need, the amount of the hydrophilic organic solvent used is preferably 10 parts by weight or less, more preferably 5 parts by weight or less, relative to 100 parts by weight of the water-absorbing resin powder.

It is possible to mix additives, which are added in a "remoistening step" described below, with the surface-crosslinking agent (aqueous solution) by adding each of the additives in a range of equal to or less than 5 parts by weight. Alternatively, it is possible to add the additives separately in a mixing substep described below.

(2. Mixing Substep)

A mixing substep is a step of mixing the water-absorbing resin powder and the surface-crosslinking agent. A method of mixing the surface-crosslinking agent is not limited to a particular one and can be a method in which a surface-crosslinking agent solution is prepared in advance, and the surface-crosslinking agent solution is mixed with the water-absorbing resin powder preferably by spraying or dropping the surface-crosslinking agent solution onto the water-absorbing resin powder, more preferably by spraying the surface-crosslinking agent solution onto the water-absorbing resin powder.

The above mixing may be performed with use of any apparatus. The apparatus is preferably a high-speed stirring mixer, more preferably a high-speed stirring continuous mixer.

(3. Heat Treatment Substep)

A heat treatment substep is a step of heating a mixture, which has been obtained in the mixing substep, so as to cause crosslinking reaction on a surface of the water-absorbing resin powder.

An apparatus for performing the crosslinking reaction is not limited to any particular one, and can be preferably a paddle dryer. A reaction temperature in the crosslinking reaction is set as appropriate according to a type of a used surface-crosslinking agent, and is preferably 50° C. to 300° C., more preferably 100° C. to 200° C.

(4. Cooling Substep)

A cooling substep is an optional step which is carried out after the heat treatment substep if needed.

An apparatus for carrying out the cooling is not limited to a particular one and is preferably an apparatus whose specification is identical with that of an apparatus used in the heat treatment substep, and more preferably a paddle dryer. This is because such an apparatus can be used as a cooling apparatus by replacing a heating medium with a cooling medium. Note that, according to need, the water-absorbing resin particles obtained in the heat treatment substep are force-cooled in the cooling substep to a temperature preferably of 40° C. to 80° C., and more preferably of 50° C. to 70° C.

(1-3-7) Remoistening Step

A remoistening step is a step of adding water, an aqueous solution, or an aqueous dispersion to the water-absorbing resin particles obtained in the surface-crosslinking step. That is, the remoistening step is a step of adding water again to a surface-crosslinked water-absorbing resin.

This step involves adding, to the surface-crosslinked water-absorbing resin as necessary, at least one additive selected from the group consisting of the foregoing polyvalent metal salts, surfactants, hydrophilic polymer compounds, cationic polymers, chelating agents, inorganic reducing agents, and hydroxycarboxylic acid compounds. In particular, this step involves adding preferably at least one additive, more preferably two kinds of additive, particularly preferably all three kinds of additives, selected from the group consisting of the foregoing polyvalent metal salts, surfactants, and hydrophilic polymer compounds. In a case where a plurality of additives are added, the order in which such additives are added is not particularly limited. For example, an aqueous solution in which a plurality of additives are dissolved together can be added to the surface-crosslinked water-absorbing resin particles. Alternatively, aqueous solutions in which a plurality of additives are dissolved respectively can be added to the surface-crosslinked water-absorbing resin particles. In a case where a plurality of aqueous solutions are added, such aqueous solutions may be added simultaneously or may be added one at a time.

Note that the above additive, when added, is preferably in the form of an aqueous solution or a slurry liquid; therefore, the surface-crosslinked water-absorbing resin particles are swollen by water again. Therefore, this step is referred to as "remoistening step". Further, as described earlier, the additive can be mixed with the water-absorbing resin powder simultaneously with the surface-crosslinking agent (aqueous solution).

(1-3-8) Other Steps

In Embodiment 1, in addition to the above described steps, it is possible to carry out a granulation step, a sizing step, a fine powder removal step, a fine powder recycling step, and/or the like according to need. Moreover, it is possible to further carry out one or more of a transportation step, a storing step, a packing step, a preserving step, and the like. Note that the "sizing step" encompasses a fine powder removal step subsequent to the surface-crosslinking step and a step of carrying out classification and pulverization in a case where a water-absorbing resin is aggregated to have a size larger than an intended size. The "fine powder recycling step" encompasses an aspect in which classified fine powder is added as-is before the classification step (especially, in polymerization step and/or gel-crushing step), and also a step of adding the fine powder, granulated into the form of a hydrogel polymer having a larger particle diameter, during any of the steps for producing the water-absorbing resin.

[1-4] Applications of Water-Absorbing Agent

Applications of the water-absorbing agent of Embodiment 1 are not particularly limited. However, the water-absorbing agent is preferably used in, for example, an absorbent body of sanitary materials which are absorbent articles such as disposable diapers, sanitary napkins, and incontinence pads. In particular, the water-absorbing agent of Embodiment 1 can be used for an absorbent body in high-concentration disposable diapers (i.e., disposable diapers each of which contains a large amount of the water-absorbing agent), which have heretofore had problems such as odor, caused by a raw material, and coloring. Further, in a case where the water-absorbing agent of Embodiment 1 is used as an upper layer part of the absorbent body, a significant effect can be expected.

An absorbent article in accordance with Embodiment 1 is an absorbent article which includes: an absorbent body which includes a water-absorbing agent and which is obtained by optionally shaping hydrophilic fibers into a sheet form; a liquid-permeable front sheet; and a liquid-impermeable back sheet. The absorbent body, if the hydrophilic fibers are not used, is formed by fixing a water-absorbing agent to paper and/or nonwoven fabric. The absorbent article in accordance with Embodiment 1, in particular, a disposable diaper for babies, a disposable diaper for adults, or a sanitary napkin, can be produced by, for example: preparing an absorbent body (absorbent core) by blending a fiber base material and a water-absorbing agent in accordance with Embodiment 1 and/or by sandwiching a water-absorbing agent in accordance with Embodiment 1 by fiber base materials; sandwiching the absorbent core by a liquid-permeable material (front sheet) and a liquid-impermeable material (back sheet); and, as necessary, providing an elastic member, diffusion layer, adhesive tape, and/or the like.

The amount of the water-absorbing agent contained in the absorbent body of the absorbent article (such an amount is referred to as "core concentration") is preferably 10 weight % or more, more preferably 20 weight % or more, particularly preferably 30 weight % or more, particularly preferably 70 weight % or more. The absorbent body is preferably pressed and shaped to a density of 0.06 g/cc or more and 0.50 g/cc or less and a basis weight of 0.01 g/cm$^2$ or more and 0.20 g/cm$^2$ or less. Examples of the fiber base material that can be used include hydrophilic fibers such as wood-ground pulp, cotton linter, crosslinked cellulose fibers, rayon, cotton, wool, acetate, and vinylon. Those obtained by air-laying these fibers are preferred.

Alternatively, as the absorbent body, it is possible to use an absorbent material such as a pulp fiber, in addition to the water-absorbing agent. In such a case, the amount (core concentration) of the water-absorbing agent contained in the absorbent body is preferably 30 weight % to 100 weight %, more preferably 40 weight % to 100 weight %, still more preferably 50 weight % to 100 weight %, further still more preferably 60 weight % to 100 weight %, particularly preferably 70 weight % to 100 weight %, and most preferably 75 weight % to 95 weight %.

In a case where the core concentration falls within the above range and the absorbent body is used as an upper layer part of an absorbent article, the absorbent article can maintain cleanness, i.e., a state of being white. Further, in such a case, the absorbent article is excellent in diffusion property with respect to a body fluid or the like such as urine or blood, and therefore improvement in absorption amount can be expected based on efficient liquid distribution.

Furthermore, a water-absorbing agent in accordance with Embodiment 1 can be used in various fields including, but not limited to, sheets for pets and waterproofing materials.

[1-5] Overview of Feeder

A feeder for use in Embodiment 1 is a feeder which is a volumetric or weight feeding apparatus for solid materials, and includes one or more drive disks therein. The one or more drive disks enable efficient feeding or efficient conveyance of solid materials. Examples of such a feeder include positive displacement pumps. A more preferred example is a feeder using a bulk solid pump (Bulk Solids Pump™, BSP) manufactured by Coperion K-tron. The feeder used in Embodiment 1 may be referred to as, for example, "bulk materials pump feeder".

A positive displacement pump is of a type that pushes a fluid from the sucking side to the discharge side utilizing a displacement of the volume of an enclosed space between a casing and a movable portion that is in contact with the inside of the casing. A pump of this type is capable of easily obtaining very high pressure. Furthermore, the amount of discharge therefrom is substantially proportional to the number of rotations, and changes only to a very small extent in response to changes in load.

The positive displacement pump, in general, means a conveyor apparatus for liquids; however, a bulk solid pump is one in which its system is adapted also for solids (see Coperion K-tron's webpage: https://www.coperion.com/en/products-services/process-equipment/feeders/bulk-solids-pump-feeders-bsp/ (visited on Apr. 3, 2017)). Therefore, a BSP is classified as a positive displacement pump. Note that the term "bulk solids" is a general term that refers to solid material in bulk, bulk solid, solid in bulk, or the like. The "Bulk Solids Pump™" is the name of a product manufactured by Coperion K-tron, which is a Coperion K-tron's original conveyor apparatus for solids with flowability. Note, however, that, although the BSP is a product name, it is generally known as the name of a conveyor apparatus for solids (see Handbook of Filters (page-281, 3-9 Feeding)). Also note that information such as the principle of material supply is available on Coperion K-tron's webpage (https://www.coperion.com/en/products-services/process-equipment/feeders/bulk-solids-pump-feeders-bsp/ (visited on Apr. 3, 2017)) and apte Inc.'s webpage (http://apte.jp/product/ktron/bsp.html (visited on Apr. 3, 2017)).

The feeder used in Embodiment 1 is more preferably a loss-in quantitative feeder (loss-in weight feeder) (also called "loss-in-weight type feeder"). As used herein, the term "loss-in" refers to a system in which: a feeder (supplying apparatus) integrally configured with a stock tank, in its entirety, is placed on a metering device; flow rate is detected from the loss in weight per unit time; and feed rate (discharge amount) is automatically controlled so that the detected flow rate matches a set value. Note that it is also preferable that, in the feeder used in Embodiment 1, the bulk solid pump is included in such a loss-in system.

Embodiment 2

The following description will discuss Embodiment 2 of the present invention in detail.

[2-1] Definitions of Terms

The same terms as those defined in Embodiment 1 of the present inventions are not described (defined) here.

(2-1-1) Particulate Water-Absorbing Agent

A "particulate water-absorbing agent" in accordance with Embodiment 2 of the present invention is suitably used in a hygienic material for absorbing a water-based liquid. A water-absorbing resin as a polymer is contained as a main component in a particulate water-absorbing agent. Specifically, the particulate water absorbing agent contains the water-absorbing resin in an amount of preferably 60 mass % to 100 mass %, 70 mass % to 100 mass %, 80 mass % to 100 mass %, or 90 mass % to 100 mass %. The particulate water-absorbing agent optionally further contains, as a non-polymer, water and/or an additive(s) (such as inorganic fine particles and/or polyvalent metal cations). A suitable moisture content is 0.2 mass % to 30 mass %. The scope of the particulate water-absorbing agent also encompasses a water-absorbing resin composition in which these components are contained.

The water-absorbing agent contains the water-absorbing resin in an amount up to approximately 100 mass %, more preferably 99 mass %, further preferably 97 mass %, particularly preferably 95 mass %, relative to the amount of the water-absorbing agent excluding water content. The water-absorbing agent preferably further contains water and/or an additive(s) (inorganic fine particles and/or polyvalent metal cations) described later.

Examples of the water-absorbing resin to be contained as a main component in the particulate water-absorbing agent include polyacrylic acid (salt)-based resins, polysulfonic acid (salt)-based resins, maleic anhydride (salt)-based resins, polyacrylamide-based resins, polyvinyl alcohol-based resins, polyethylene oxide-based resins, polyaspartic acid (salt)-based resins, polyglutamic acid (salt)-based resins, polyalginic acid (salt)-based resins, starch-based resins, and cellulose-based resins. The water-absorbing resin is preferably a polyacrylic acid (salt)-based resin.

(2-1-2) Liquid Permeability

The term "liquid permeability" of a particulate water-absorbing agent or a water-absorbing resin as used in the present invention refers to flowability of a liquid passing through a space between particles of a swollen gel of a water-absorbing resin under load or without load. The "liquid permeability" is measured typically as a Saline Flow Conductivity (SFC).

The term "SFC" refers to liquid permeability of a 0.69 weight % aqueous sodium chloride solution in a particulate water-absorbing agent or in a water-absorbing resin under a load of 2.07 kPa, and is measured in conformity with the SFC test method disclosed in U.S. Pat. No. 5,669,894.

(2-1-3) Moisture Absorption Flowability Improving Agent

The term "moisture absorption flowability improving agent" as used in the present invention refers to a compound or a composition which increases the moisture absorption flowability (B.R.) of a particulate water-absorbing agent or a water-absorbing resin in a case where the moisture absorption flowability improving agent is added to the particulate water-absorbing agent or the water-absorbing resin. Examples of the moisture absorption flowability improving agent include, but are not limited to, silicon dioxide, hydrotalcite, phosphates, and aluminum salts.

(2-1-4) Gel-Grinding Energy (GGE)

The term "gel-grinding energy" as used in the present invention refers to mechanical energy per unit weight (unit weight of a crosslinked hydrogel polymer), the mechanical energy being necessary for a gel-crushing device to gel-crush a crosslinked hydrogel polymer. The gel-grinding energy does not include energy with which to heat or cool a jacket, or energy of water or steam to be introduced. Note that "gel-grinding energy" is abbreviated as "GGE". In a case where the gel-crushing device is driven by a three-phase alternating current power, the GGE is calculated based on the following Equation (1).

GGE (J/g)={√3×voltage×electric current×power factor×motor efficiency}/{weight of crosslinked hydrogel polymer introduced into gel crusher per second}      Equation (1)

The "power factor" and the "motor efficiency" are each a value which is unique to the gel-crushing device and changes depending on, for example, an operation condition of the gel-crushing device and which ranges from 0 to 1. These values can be known by, for example, making inquiries to a manufacturer of the device or the like. In a case where the gel-crushing device is driven by a single-phase alternating current power, GGE can be calculated by replacing "√3" with "1" in the above Equation (1). Note that a unit of a voltage is [V], a unit of an electric current is [A], and a unit of weight of a crosslinked hydrogel polymer is [g/s]. GGE is measured by the method disclosed in International Publication, No. 2011/126079.

Since the mechanical energy to be applied to the crosslinked hydrogel polymer is important in the present invention, the gel-grinding energy is preferably calculated by subtracting an electric current value of the gel-crushing device during idling from an electric current value of the gel-crushing device during gel-crushing. In a case where gel-crushing is carried out with use of a plurality of gel-crushing devices, in particular, a sum of electric current values of the plurality of gel-crushing devices during idling is large. It is therefore suitable to calculate the gel-grinding energy by subtracting the electric current values of the plurality of gel-crushing devices during idling from current values of the plurality of gel-crushing devices during gel-crushing. In this case, the gel-grinding energy is calculated by the following Equation (2). Note that this gel-grinding energy is denoted as GGE (2) to be distinguished from the GGE described earlier.

GGE (2)(J/g)={√3×voltage×(electric current during gel-crushing−electric current during idling)×power factor×motor efficiency}/{weight of crosslinked hydrogel polymer introduced into gel crusher per second}      Equation (2)

The "power factor" and the "motor efficiency" during gel-crushing are applied to the GGE (2). Since the electric current value during idling is small, the values of the power factor and the motor efficiency during idling are defined approximately as in the Equation (2). For example, in a case where the amount of the crosslinked hydrogel polymer to be continuously supplied by a quantitative feeder is [t/hr], the "weight of crosslinked hydrogel polymer to be introduced into gel crusher per second [g/s]" in each of Equations (1) and (2) refers to a value obtained by converting [t/hr] into [g/s].

[2-2] Method for Producing Polyacrylic Acid (Salt)-Based Particulate Water-Absorbing Agent The following description will discuss steps (2-2-1) to (2-2-11) for producing a particulate water-absorbing agent in accordance with the present invention.

(2-2-1) Step of Preparing Aqueous Monomer Solution

A step of preparing aqueous monomer solution is a step of preparing an aqueous solution containing a monomer (e.g., an acrylic acid (salt)) as a main component (this solution is hereinafter referred to as an "aqueous monomer solution"). It is also possible to use a monomer slurry liquid, provided that a water-absorbing resin to be produced will not have degraded water absorption performance. For convenience of description, however, this section describes an aqueous monomer solution.

The term "main component" means that the acrylic acid (salt) is used (contained) in an amount of ordinarily 50 mol % or more, preferably of 70 mol % or more, more preferably of 90 mol % or more (with an upper limit of 100 mol %), relative to the total amount of monomers used for a polymerization reaction of a water-absorbing resin (excluding an internal crosslinking agent).

(1. Acrylic Acid)

For the present invention, it is preferable that an acrylic acid and/or an acrylic acid salt (hereinafter referred to as "acrylic acid (salt)") is used as a monomer from the viewpoint of physical properties of a particulate water-absorbing agent to be produced and productivity.

The "acrylic acid" may be a known acrylic acid, and may contain, as a polymerization inhibitor, preferably a methoxyphenol, more preferably p-methoxyphenol. The acrylic acid only needs to be contained in an amount of preferably 200 ppm or less, more preferably 10 ppm to 160 ppm, even more preferably 20 ppm to 100 ppm, from the viewpoint of polymerizability of the acrylic acid and the color of a particulate water-absorbing agent to be produced. An impurity in the acrylic acid for the present invention may be any of compounds disclosed in U.S. Patent Application Publication No. 2008/0161512.

The "acrylic acid salt" is produced by neutralizing the above acrylic acid with a basic composition below. The acrylic acid salt may be a commercially available acrylic acid salt (for example, sodium acrylate) or may be produced by neutralizing an acrylic acid in a plant for producing a particulate water-absorbing agent.

(2. Basic Composition)

In the present invention, the term "basic composition" refers to a composition containing a basic compound, such as a commercially available aqueous sodium hydroxide solution.

Specific examples of the basic compound include carbonates or bicarbonates of alkali metals, hydroxides of alkali metals, ammonia, and organic amines. Among these, the basic compound preferably has strong basicity from the viewpoint of physical properties of a particulate water-absorbing agent to be obtained. That is, the basic compound is preferably a hydroxide of an alkali metal, such as sodium hydroxide, potassium hydroxide, or lithium hydroxide, and is more preferably sodium hydroxide.

(3. Neutralization)

In the present invention, neutralization can be neutralization of an acrylic acid (before polymerization), neutralization of a crosslinked hydrogel polymer obtained by crosslinking and polymerizing an acrylic acid (after polymerization) (hereinafter referred to as "later neutralization"), or a combination of the neutralization of an acrylic acid and the neutralization of a crosslinked hydrogel polymer obtained by crosslinking and polymerizing an acrylic acid. These neutralizations are not limited to any particular type, and can be of a continuous type or a batch type. Among these, a continuous type is preferable from the viewpoint of production efficiency and the like.

Note that with regard to conditions such as a neutralization apparatus, a neutralization temperature, and a retention time, the conditions disclosed in International Publication No. 2009/123197 and U.S. Patent Application Publication No. 2008/0194863 can be applied to the present invention.

A neutralization rate in the present invention is preferably 10 mol % to 90 mol %, more preferably 40 mol % to 85 mol %, even more preferably 50 mol % to 80 mol %, and particularly preferably 60 mol % to 75 mol % relative to monomers' acid groups. At a neutralization rate of less than 10 mol %, a fluid retention capacity may be lowered significantly. On the contrary, in a case where the neutralization rate is higher than 90 mol %, it may not be possible to obtain a water-absorbing resin having a high fluid retention capacity under pressure.

The neutralization rate also applies to the later neutralization. The neutralization rate can also apply to a neutralization rate for a particulate water-absorbing agent which is an end product. Note that a neutralization rate of 75 mol % means a mixture of 25 mol % of an acrylic acid and 75 mol % of an acrylic acid salt. The mixture is referred to also as a partially neutralized acrylic acid.

(4. Other Monomer(s))

In the present invention, "other monomer(s)" refers to a monomer(s) other than the acrylic acid (salt), and a particulate water-absorbing agent can be produced by using the other monomer(s) in combination with the acrylic acid (salt).

Examples of the other monomer(s) include unsaturated monomers which are water-soluble or hydrophobic. Specifically, any of compounds disclosed in U.S. Patent Application Publication No. 2005/0215734 (except an acrylic acid) can be applied to the present invention.

(5. Internal Crosslinking Agent)

An internal crosslinking agent for use in the present invention may be any of compounds disclosed in U.S. Pat. No. 6,241,928. One of the compounds or two or more of the compounds is/are selected in view of reactivity.

From the viewpoint of, for example, the water absorption performance of a water-absorbing resin to be produced, the internal crosslinking agent is preferably a compound having two or more polymerizable unsaturated groups, more preferably a compound that is pyrolytic at a drying temperature below, even more preferably a compound having a (poly) alkylene glycol structural unit and two or more polymerizable unsaturated groups.

The polymerizable unsaturated groups are preferably an allyl group or a (meth)acrylate group, more preferably a (meth)acrylate group. The (poly)alkylene glycol structural unit is preferably polyethylene glycol. The number of alkylene glycol units in the (poly)alkylene glycol is preferably 1 to 100, more preferably 6 to 50.

Therefore, in the present invention, preferably (poly) alkylene glycol di(meth)acrylate or (poly)alkylene glycol tri(meth)acrylate is used, and more preferably (poly)ethylene glycol di(meth)acrylate is used.

The internal crosslinking agent is used in an amount of preferably 0.0001 mol % to 10 mol %, more preferably 0.001 mol % to 1 mol % relative to the total amount of monomers. In a case where the amount used falls within the above ranges, a desired water-absorbing resin can be obtained. Note that in a case where the amount used is excessively small, gel strength tends to be lowered and consequently there tends to be an increase in water-soluble content. In a case where the used amount is excessively large, fluid retention capacity tends to be lowered. Therefore, the amount used that is excessively large or excessively small is not preferable.

For the present invention, the following method is preferably used: An aqueous monomer solution to which a certain amount of internal crosslinking agent has been added in advance is prepared. Then, the aqueous monomer solution is simultaneously subjected to polymerization and to a crosslinking reaction. Alternatively, other than the above method, examples of a possible method include a method in which an internal crosslinking agent is added during or after the polymerization so that postcrosslinking is carried out, a method in which radical crosslinking is carried out with use of a radical polymerization initiator, and a method in which radiation crosslinking is carried out with use of active energy rays such as an electron ray and an ultraviolet ray. Alternatively, these methods may be used in combination.

(6. Other Substances Added to Aqueous Monomer Solution)

The present invention may include adding any substance below to the aqueous monomer solution during the preparation thereof from the viewpoint of improved physical properties for a water-absorbing resin to be produced.

Specific examples of such a substance include hydrophilic polymers such as starch, starch derivatives, cellulose, cellulose derivatives, polyvinyl alcohol, polyacrylic acids (salts), and crosslinked polyacrylic acids (salts). Any of such substances can be contained in an amount of preferably 50 weight % or less, more preferably 20 weight % or less, even more preferably 10 weight % or less, particularly preferably 5 weight % or less (with a lower limit value of 0 weight %). Alternatively, a carbonate, an azo compound, a foaming agent such as gas bubbles or the like, a surfactant, a chelating agent, a chain transfer agent, and/or the like may be added. Any of such substances can be contained in an amount of preferably 5 weight % or less, more preferably 1 weight % or less, even more preferably 0.5 weight % or less (with a lower limit value of 0 weight %).

The above substances are not necessarily added to the aqueous monomer solution, but can be added during the polymerization, or can be added both to the aqueous monomer solution and during the polymerization.

In a case where a water-soluble resin or a water-absorbing resin is used as the hydrophilic polymer, a graft polymer or a water-absorbing resin composition (for example, an starch-acrylic acid polymer or a PVA-acrylic acid polymer) can be obtained. These polymers and water-absorbing resin compositions are also encompassed in the scope of the present invention.

(7. Monomer Component Concentration)

The above various substances are added when an aqueous monomer solution is prepared during the step of preparing an aqueous monomer solution. The aqueous monomer solution may contain a monomer component at any concentration. The concentration is preferably 10 weight % to 80 weight %, more preferably 20 weight % to 75 weight %, even more preferably 30 weight % to 70 weight %, from the viewpoint of physical properties of a water-absorbing resin.

In a case where aqueous solution polymerization or reversed phase suspension polymerization is employed, a solvent other than water can be used in combination with water as necessary. In such a case, the type of the solvent used is not limited to any particular one.

The "monomer component concentration" is a value obtained using Equation (3) below. The weight of the aqueous monomer solution does not include the weight of a graft component, water-absorbing resin, or a hydrophobic solvent used in reversed phase suspension polymerization.

(Monomer component concentration (weight %))= (weight of monomer component)/(weight of aqueous monomer solution)×100    Equation (3):

(2-2-2) Polymerization Step

A polymerization step is a step of polymerizing an aqueous acrylic acid (salt)-based monomer solution obtained in the step of preparing the aqueous monomer solution, so that a crosslinked hydrogel polymer (hereinafter referred to as "hydrogel") is obtained.

(1. Polymerization Initiator)

The polymerization initiator for use in the present invention is selected as appropriate in accordance with a form of polymerization or the like and is not limited to any particular one. Examples of the polymerization initiator include pyrolysis-type polymerization initiators, photolysis-type polymerization initiators, redox-type polymerization initiators containing a reducing agent for facilitating decomposition of any of those polymerization initiators. Specifically, used as the polymerization initiator is one of the polymerization initiators disclosed in U.S. Pat. No. 7,265,190, or two or more of the polymerization initiators disclosed in U.S. Pat. No. 7,265,190. Further, the polymerization initiator is preferably a peroxide or an azo compound, more preferably a peroxide, even more preferably a persulfate, from the viewpoint of the handleability of the polymerization initiator and the physical properties of the particulate water-absorbing agent or the water-absorbing resin.

The amount of the polymerization initiator used is preferably 0.001 mol % to 1 mol %, more preferably 0.001 mol % to 0.5 mol %, relative to the amount of monomers. The amount of the reducing agent used is preferably 0.0001 mol % to 0.02 mol %, relative to the amount of monomers.

A polymerization reaction can be carried out by, instead of using the polymerization initiator, irradiating a monomer with an active energy ray such as a radial ray, an electron ray, or an ultraviolet ray. Alternatively, any of these active energy rays can be used in combination with a polymerization initiator.

(2. Form of Polymerization)

Polymerization to be applied to the present invention is not limited to any particular form. From the viewpoint of a water absorbent property, ease of control of polymerization, and the like, preferable examples of the polymerization include spray droplet polymerization, aqueous solution polymerization, and reversed phase suspension polymerization, more preferable examples of the polymerization include aqueous solution polymerization and reverse phase suspension polymerization, and even more preferable examples of the polymerization include aqueous solution polymerization. Among these, continuous aqueous solution polymerization is particularly preferable. The continuous aqueous solution polymerization can be any one of continuous belt polymerization and continuous kneader polymerization.

Specific examples of the form of continuous belt polymerization include those disclosed in U.S. Pat. Nos. 4,893,999, 6,241,928, and U.S. Patent Application Publication No. 2005/0215734. Specific examples of the form of continuous kneader polymerization include those disclosed in U.S. Pat. Nos. 6,987,151 and 6,710,141. In a case where these forms of continuous aqueous solution polymerization are employed, it is possible to improve efficiency with which a water-absorbing resin is produced.

Preferable examples of the form of the continuous aqueous solution polymerization include "high-temperature-initiating polymerization" and "high-concentration polymerization". The "high-temperature-initiating polymerization" is a form of polymerization in which polymerization is started while a temperature of an aqueous monomer solution is preferably 30° C. or higher, more preferably 35° C. or higher, even more preferably 40° C. or higher, and particularly preferably 50° C. or higher (upper limit value: boiling point). The "high-concentration polymerization" is a form of polymerization in which polymerization is carried out while a monomer concentration is preferably 30 weight % or more, more preferably 35 weight % or more, even more preferably 40 weight % or more, and particularly preferably 45 weight % or more (upper limit value: saturated concentration). Alternatively, it is possible to use these forms of polymerization in combination.

In the present invention, polymerization can be carried out in an air atmosphere. From the viewpoint of color of a water-absorbing resin to be obtained, polymerization is carried out preferably in an atmosphere of an inert gas such as nitrogen or argon. In the case where polymerization is carried out in an atmosphere of an inert gas such as nitrogen or argon, an oxygen concentration is preferably controlled to be, for example, 1 volume % or less. Note that dissolved oxygen in an aqueous monomer solution is also preferably substituted with an inert gas (e.g., dissolved oxygen: less than 1 mg/l).

In the present invention, alternatively, it is possible to carry out foaming polymerization in which polymerization is carried out while gas bubbles (particularly the inert gas or the like) are dispersed into an aqueous monomer solution.

In the present invention, alternatively, it is possible to increase solid content concentration during polymerization. The degree of increase in solid content, as an index of an increase in such a solid content concentration, is defined by the following Equation (4). Note that the degree of increase in solid content concentration is preferably 1 weight % or more, more preferably 2 weight % or more.

(Degree of increase in solid content (weight %))= (solid content concentration in hydrogel after polymerization (weight %))−(solid content concentration in aqueous monomer solution (weight %)), Equation (4):

where the solid content concentration in an aqueous monomer solution is a value obtained by the following Equation (5) and where components in a polymerization system are an aqueous monomer solution, a graft component, a water-absorbing resin and other solid matters (e.g., water-insoluble fine particles and the like), and therefore exclude a hydrophobic solvent in reverse phase suspension polymerization.

(Solid content concentration in aqueous monomer solution (weight %))={weight of (monomer component+graft component+water-absorbing resin+other solid matters)}/(weight of components in polymerization system)×100 Equation (5):

(2-2-3) Gel-Crushing Step

A gel-crushing step is a step of gel-crushing a hydrogel, which has been obtained by the polymerization step, with use of, for example, a kneader, a screw extruder such as a meat chopper, or a gel-crusher such as a cutter mill to obtain a hydrogel in the form of particles (hereinafter referred to as "particulate hydrogel"). In a case where the polymerization step is carried out through kneader polymerization, such a step is equivalent to a combination of the polymerization step and the gel-crushing step which are carried out simultaneously. In a case where a particulate hydrogel is directly obtained through a polymerization process such as vapor phase polymerization or reverse phase suspension polymerization, the gel-crushing step may not be carried out.

With regard to gel-crushing conditions and forms other than above described, any of conditions and forms disclosed in International Publication No. 2011/126079 can be preferably employed in the present invention.

(2-2-4) Drying Step

A drying step is a step of drying the particulate hydrogel, which has been obtained by the polymerization step and/or the gel-crushing step, until a desired resin solid content is attained, so as to obtain a dried polymer. The resin solid content is calculated from drying loss (a change in weight after heating 1 g of the water-absorbing resin at 180° C. for three hours). The resin solid content is preferably 80 weight % or more, more preferably 85 weight % to 99 weight %, even more preferably 90 weight % to 98 weight %, particularly preferably 92 weight % to 97 weight %.

A drying method of drying the particulate hydrogel is not particularly limited. Examples of the drying method include thermal drying, hot air drying, drying under reduced pressure, fluidized bed drying, infrared drying, microwave drying, drum dryer drying, drying by azeotropic dehydration with a hydrophobic organic solvent, and high humidity drying by use of high temperature water vapor. The drying method is, among others, preferably hot air drying, more preferably band drying, in which hot air drying is performed on a through-flow belt, from the viewpoint of drying efficiency.

From the viewpoint of the color of a water-absorbing resin to be produced and drying efficiency, the hot air drying is performed at a drying temperature (temperature of hot air) of preferably 120° C. to 250° C., more preferably 150° C. to 200° C. Drying conditions other than the drying temperature (e.g., the air velocity of hot air and the drying time) can be set as appropriate in accordance with moisture content of the particulate hydrogel to be dried, total weight of the particulate hydrogel to be dried, and a desired resin solid content. In the case of band drying, the various conditions disclosed in, for example, International Publication No. 2006/100300, International Publication No. 2011/025012, International Publication No. 2011/025013, and International Publication No. 2011/111657 can be applied as necessary.

Setting the drying temperature and the drying time to be within these ranges makes it possible to obtain a water-absorbing resin whose CRC (fluid retention capacity), water-soluble content (Ext), and color are within desired ranges (see the following section [3]).

(2-2-5) Pulverizing Step and Classification Step

A pulverizing step and classification step are steps of pulverizing (pulverizing step) the dried polymer obtained in the drying step and adjusting (classification step) the particle size of a resulting pulverized polymer to have a particle size within a certain range so that a water-absorbing resin powder is obtained (for convenience, water-absorbing resin in a powder form before being subjected to surface crosslinking is referred to as "water-absorbing resin powder").

An apparatus used in the pulverizing step of the present invention can be, for example, a high-speed pulverizer such as a roll mill, a hammer mill, a screw mill, or a pin mill; a vibrating mill; a knuckle-type pulverizer; a cylindrical mixer; or the like. These apparatuses can be used in combination according to need.

A particle size adjusting method in the classification step of the present invention is not limited to a particular one and can be, for example, sieve classification with use of one or more JIS standard sieves (JIS Z8801-1 (2000)), airflow classification, or the like. Note that the particle size of water-absorbing resin is not limited to being adjusted during the pulverizing step and classification step, but may alternatively be adjusted as appropriate during the polymerization step (in particular, in reversed phase suspension polymerization or spray droplet polymerization) or some other step (for example, a granulation step or a fine powder recycling step).

The water-absorbing resin powder obtained in the present invention has a weight average particle diameter (D50) of preferably 200 μm to 600 μm, more preferably 200 μm to 550 μm, even more preferably 250 μm to 500 μm, particularly preferably 350 μm to 450 μm. The water-absorbing resin powder contains particles with a particle diameter of less than 150 μm at a proportion of preferably 10 weight % or less, more preferably 5 weight % or less, even more preferably 1 weight % or less, and contains particles with a particle diameter of 850 μm or more at a proportion of preferably 5 weight % or less, more preferably 3 weight % or less, and even more preferably 1 weight % or less. A lower limit value of each of the proportions of such particles is preferably as low as possible and is desirably 0 weight %. Note, however, that a lower limit of each of the proportions of such particles can be approximately 0.1 weight %. The water-absorbing resin powder has a logarithmic standard deviation ($\sigma\zeta$) of a particle size distribution of preferably 0.20 to 0.50, more preferably 0.25 to 0.40, and still more preferably 0.27 to 0.35. Note that these particle sizes are measured with use of standard sieves in conformity with a measuring method disclosed in U.S. Pat. No. 7,638,570 and a measuring method disclosed in EDANA ERT 420.2-02.

The above particle sizes apply not only to water-absorbing resin subsequent to surface crosslinking (for convenience, hereinafter referred to also as "water-absorbing resin particle(s)"), but also to the particulate water-absorbing agent as a final product. Therefore, it is preferable to subject the water-absorbing resin particles to surface crosslinking (surface-crosslinking step) so that the particle size falling within the above described range is maintained, and it is more preferable to carry out particle size adjustment by carrying out a sizing step subsequent to the surface-crosslinking step.

(2-2-6) Surface-Crosslinking Step

A surface-crosslinking step is a step of forming a portion with a higher crosslinking density in a surface layer (that is, a portion, of the water-absorbing resin powder which is up to several tens of micrometers deep from the surface) of the water-absorbing resin powder produced through the above steps. This step includes a mixing substep, a heat treatment substep, and optionally a cooling substep.

In the surface-crosslinking step, a water-absorbing resin (water-absorbing resin particles) can be obtained which has been surface-crosslinked by radical crosslinking on the surface of the water-absorbing resin powder, surface polymerization on the surface of the water-absorbing resin powder, crosslinking reaction with a surface-crosslinking agent, or the like.

(1. Surface-Crosslinking Agent)

A surface-crosslinking agent used in the present invention is not limited to any particular one. Examples of the surface-crosslinking agent include organic surface-crosslinking agents and inorganic surface-crosslinking agents. Among others, an organic surface-crosslinking agent that is reactive with a carboxyl group is preferable, from the viewpoint of the physical properties of a water-absorbing resin and the handleability of the surface-crosslinking agent. For example, one of the surface-crosslinking agents disclosed in U.S. Pat. No. 7,183,456 can be used, or two or more of the surface-crosslinking agents disclosed in U.S. Pat. No. 7,183,456 can be used. Specifically, examples of the surface-crosslinking agent include polyhydric alcohol compounds, epoxy compounds, haloepoxy compounds, polyamine compounds, condensates of a haloepoxy compound and a polyamine compound, oxazoline compounds, oxazolidinone compounds, polyvalent metal salts, alkylene carbonate compounds, cyclic urea compounds, and the like.

The amount of the surface-crosslinking agent used (or the total amount used in a case where a plurality of surface-crosslinking agents are used) is preferably 0.01 parts by weight to 10 parts by weight, more preferably 0.01 parts by weight to 5 parts by weight, relative to 100 parts by weight of the water-absorbing resin powder. The surface-crosslinking agent is preferably added as an aqueous solution. In such a case, the amount of water used is preferably 0.1 parts by weight to 20 parts by weight, more preferably 0.5 parts by weight to 10 parts by weight, relative to 100 parts by weight of the water-absorbing resin powder. In a case where a hydrophilic organic solvent is used according to need, the amount of the hydrophilic organic solvent used is preferably 10 parts by weight or less, more preferably 5 parts by weight or less, relative to 100 parts by weight of the water-absorbing resin powder.

It is possible to mix additives, which are added in a "remoistening step" described below, with the surface-crosslinking agent (aqueous solution) by adding each of the additives in a range of equal to or less than 5 parts by weight. Alternatively, it is possible to add the additives separately in a mixing substep described below.

(2. Mixing Substep)

A mixing substep is a step of mixing the water-absorbing resin powder and the surface-crosslinking agent. A method of mixing the surface-crosslinking agent is not limited to a particular one and can be a method in which a surface-crosslinking agent solution is prepared in advance, and the surface-crosslinking agent solution is mixed with the water-absorbing resin powder preferably by spraying or dropping the surface-crosslinking agent solution onto the water-absorbing resin powder, more preferably by spraying the surface-crosslinking agent solution onto the water-absorbing resin powder.

The above mixing may be performed with use of any apparatus. The apparatus is preferably a high-speed stirring mixer, more preferably a high-speed stirring continuous mixer.

(3. Heat Treatment Substep)

A heat treatment substep is a step of heating a mixture, which has been obtained in the mixing substep, so as to cause crosslinking reaction on a surface of the water-absorbing resin powder.

An apparatus for performing the crosslinking reaction is not limited to any particular one, and can be preferably a paddle dryer. A reaction temperature in the crosslinking reaction is set as appropriate according to a type of a used surface-crosslinking agent, and is preferably 50° C. to 300° C., more preferably 100° C. to 200° C.

(4. Cooling Substep)

A cooling substep is an optional step which is carried out after the heat treatment substep if needed.

An apparatus for carrying out the cooling is not limited to a particular one and is preferably an apparatus whose specification is identical with that of an apparatus used in the heat treatment substep, and more preferably a paddle dryer. This is because such an apparatus can be used as a cooling apparatus by replacing a heating medium with a cooling medium. Note that, according to need, the water-absorbing resin particles obtained in the heat treatment substep are force-cooled in the cooling substep to a temperature preferably of 40° C. to 80° C., more preferably of 50° C. to 70° C.

(2-2-7) Remoistening Step

A remoistening step is a step of adding water, an aqueous solution, or an aqueous dispersion to the water-absorbing resin particles obtained in the surface-crosslinking step. That is, the remoistening step is a step of adding water again to a surface-crosslinked water-absorbing resin. The remoistening step here is a step of adding, as necessary, at least one additive selected from the group consisting of polyvalent metal salt compounds, polycationic polymers, chelating agents, inorganic reducing agents, hydroxycarboxylic acid compounds, and moisture absorption flowability improving agents which are present in water (these are described later).

Note that the above additive, when added, is preferably in the form of an aqueous solution or a slurry liquid; therefore, the water-absorbing resin particles are swollen by water again. Therefore, this step is referred to as "remoistening step". Further, as described earlier, the additive can be mixed with the water-absorbing resin powder simultaneously with the surface-crosslinking agent (aqueous solution).

(1. Polyvalent Metal Salt and/or Cationic Polymer)

In the present invention, a polyvalent metal salt and/or a cationic polymer is/are preferably added, from the viewpoint of improvement in water absorption speed, liquid permeability, moisture absorption flowability, and the like of the water-absorbing resin to be obtained.

The polyvalent metal salt and/or cationic polymer used in the present invention may be, specifically, any of compounds disclosed under "[7] Polyvalent metal salt and/or cationic polymer" of International Publication, No. 2011/040530, and may be used in any of the amounts disclosed thereunder.

(2. Chelating Agent)

In the present invention, a chelating agent is preferably added from the viewpoint of, for example, color of the water-absorbing resin to be obtained (coloration prevention) and prevention of deterioration of the water-absorbing agent.

The chelating agent used in the present invention may be, specifically, any of compounds disclosed under "[2] Chelating agent" of International Publication No. 2011/040530, and may be used in any of the amounts disclosed thereunder.

(3. Inorganic Reducing Agent)

In the present invention, an inorganic reducing agent is preferably added from the viewpoint of, for example, color (coloration prevention), deterioration prevention, and reduction in residual monomers in the water-absorbing resin to be obtained.

The inorganic reducing agent used in the present invention may be, specifically, any of compounds disclosed under "[3] Inorganic reducing agent" of International Publication No. 2011/040530, and may be used in any of the amounts disclosed thereunder.

(4. A-Hydroxycarboxylic Acid Compound)

In the present invention, an α-hydroxycarboxylic acid is preferably added from the viewpoint of, for example, color of the water-absorbing resin to be obtained (coloration prevention). Note that the "α-hydroxycarboxylic acid compound" is a carboxylic acid having a hydroxyl group in a molecule or is a salt thereof, and is a hydroxycarboxylic acid having a hydroxyl group at an alpha position.

The α-hydroxycarboxylic acid compound used in the present invention may be, specifically, any of compounds disclosed under "[6] a-hydroxycarboxylic acid compound" of International Publication No. 2011/040530, and may be used in any of the amounts disclosed thereunder.

(2-2-8) Step of Adding Polyvalent Metal Salt of Organic Acid

The particulate water-absorbing agent contains a water-absorbing resin and a polyvalent metal salt of an organic acid (hereinafter referred to as "organic acid polyvalent metal salt"), and may further contain some other compound other than the water-absorbing resin and the organic acid polyvalent metal salt (such other compound is hereinafter referred to as "other constituent").

The particulate water-absorbing agent, which is obtained by adding an organic acid polyvalent metal salt to a particulate water-absorbing resin and which has specific parameters, shows excellent flowability as powder both when in a dry state and in a moistened state and shows excellent absorption performance even when subjected to mechanical impact.

(1. Organic Acid Polyvalent Metal Salt)

An organic acid polyvalent metal salt in accordance with the present invention contains seven or more carbon atoms per molecule, and is composed of a metal salt (other than alkali metal salts) of a fatty acid, a petroleum acid, a polymer acid, or the like.

The organic acid of the organic acid polyvalent metal salt may be any organic acid, provided that the organic acid is organic matter that forms a salt with a polyvalent metal. The organic acid is preferably an organic carboxylic acid, an organic sulfonic acid, or an organic sulfinic acid. Among these, an organic carboxylic acid containing a carboxyl group in its molecule is particularly preferred. The number of carbon atoms of the organic acid polyvalent metal salt may be 7 or more, more preferably within the range of from 7 to 20, even more preferably 12 to 20.

In a case where an organic acid containing less than seven carbon atoms in its molecule is used as the above organic acid, the organic acid polyvalent metal salt dissolves in water to a greater extent, and, when a disposable diaper, an absorbent body or the like is in use, the organic acid polyvalent metal salt may flow into an absorbed liquid such as urine or blood. Therefore, an organic acid containing less than seven carbon atoms in a molecule is not preferred. Furthermore, in a case where the organic acid is an acid containing less than seven carbon atoms in its molecule such as oxalic acid or citric acid, a polyvalent metal salt of such an organic acid has a high degree of hardness and therefore, when subjected to mechanical impact, results in a decrease in absorbent property. Furthermore, use of oxalic acid is not preferred also from a safety point of view.

Examples of the organic carboxylic acid include saturated or unsaturated organic carboxylic acids and aromatic carboxylic acids. The organic carboxylic acid may contain a substituent group other than the carboxy group, examples of which include hydroxyl group and halogen. The organic carboxylic acid may be a polycarboxylic acid that contains a plurality of carboxy groups in its molecule, but is preferably a monocarboxylic acid.

Specific examples of the organic carboxylic acid include: long-chain or branched fatty acids such as caproic acid, octylic acid, octynoic acid, decanoic acid, lauric acid, myristic acid, palmitic acid, oleic acid, and stearic acid; petroleum acids such as benzoic acid, myristic acid, naphthenic acid, naphthoic acid, and naphthoxyacetic acid; and polymer acids such as poly(meth)acrylic acids and poly sulfonic acids. Preferred among those listed above are fatty acids such as caproic acid, octylic acid, octynoic acid, decanoic acid, lauric acid, myristic acid, palmitic acid, oleic acid, stearic acid, beef fatty acids and hydrogenated castor oil fatty acid, more preferred are fatty acids containing no unsaturated bonds in its molecule (long-chain saturated fatty acids) such as caproic acid, octylic acid, decanoic acid, lauric acid, myristic acid, palmitic acid, and stearic acid, and most preferred are long-chain fatty acids containing 12 to 20 carbon atoms in its molecule and containing no unsaturated bonds in its molecule (long-chain saturated fatty acids) such as lauric acid, myristic acid, palmitic acid, and stearic acid. The reason therefor is that, in a case where a fatty acid containing an unsaturated bond in its molecule is used, the particulate water-absorbing agent may, for example, change in color and issue an order when subjected to heat and/or oxidation during storage.

On the other hand, the metal salt of the organic acid polyvalent metal salt is not particularly limited, provided that the metal salt is other than alkali metal salts, i.e., provided that the metal salt is, for example, an alkaline earth metal salt or a transition metal salt. The metal salt is preferably a barium salt, a calcium salt, a magnesium salt, an aluminum salt, or a zinc salt, because these are easily available. Among these, a calcium salt, a magnesium salt, a zinc salt, and an aluminum salt are more preferred.

Accordingly, specific examples of the organic acid polyvalent metal salt include calcium laurate, magnesium laurate, zinc laurate, aluminum laurate, calcium myristate, magnesium myristate, aluminum myristate, zinc myristate, calcium palmitate, magnesium palmitate, aluminum palmitate, zinc palmitate, calcium stearate, magnesium stearate, zinc stearate, and aluminum stearate.

Furthermore, the organic acid polyvalent metal salt may be partially hydroxide or the like. More specifically, the organic acid polyvalent metal salt may have a salt structure represented by, for example, "(organic acid)$\times M^{n+}(OH)_{n-x}$", where $M^{n+}$ represents an n-valent metal ion species, x represents an integer of 1 to n, and n represents an integer of 2 or more.

Any combination the foregoing organic acids and any of the foregoing metal salts may be combined to obtain the foregoing organic acid polyvalent metal salt. Furthermore, one organic acid polyvalent metal salt may be used or a mixture of two or more organic acid polyvalent metal salts may be used.

The organic acid polyvalent metal salt is not limited to those in which all the acid groups are neutralized to salts, and may be any of those containing a small amount of organic acid or containing an excessive amount of polyvalent metal. Suitably usable among those listed above is a salt in which preferably 90 mol % or more of the total moles of acid groups (carboxyl groups) are neutralized. More suitably usable is a neutralized salt in which more preferably 95 mol % to 105 mol %, even more preferably 98 mol % to 102 mol %, particularly preferably 99 mol % to 101 mol % of the total moles of acid groups (carboxyl groups) are neutralized.

Note that, in a case where a polymer acid such as a polyacrylic acid is used as the organic acid, it is preferable that 95 mol % or more of the total moles of acid groups (carboxyl groups) of the polymer acid are neutralized (form a salt with a polyvalent metal) to from a neutralized salt. More preferably 98 mol % or more, even more preferably 99 mol % or more of the total moles of acid groups are neutralized. The molecular weight (weight average molecular weight) of the polymer acid used is usually 10,000 to 5,000,000, preferably 50,000 to 1,000,000.

The organic acid polyvalent metal salt is in a powder form, and is not particularly limited as to its particle diameter. Usually, the particle diameter of the organic acid polyvalent metal salt is preferably smaller than weight (mass) average particle diameter of the water-absorbing resin. Specifically, it is preferable that 90 mass % or more of the entire organic acid polyvalent metal salt contained in the particulate water-absorbing agent of the present invention has a particle diameter of more than 0 and 100 μm or less, more preferably 0.01 μm to 50 μm, even more preferably 0.01 μm to 10 μm.

The melting point of the organic acid polyvalent metal salt is preferably 20° C. or above and 250° C. or below, more preferably 40° C. or above and 250° C. or below, even more preferably 50° C. or above and 250° C. or below. Among those listed above, the melting point is particularly preferably 60° C. or above and 250° C. or below, more preferably 70° C. or above and 250° C. or below, most preferably 80° C. or above and 250° C. or below. In a case where the melting point of the organic acid polyvalent metal salt is 250° C. or above, the organic acid polyvalent metal salt becomes less adhesive to the surface of the water-absorbing resin, resulting in an increase in amount of the organic acid polyvalent metal salt falling off the water-absorbing resin. In a case where the melting point is 20° C. or below, the particulate water-absorbing agent obtained has poor flowability and becomes difficult to handle; therefore, a melting point of 20° C. or below is not preferred.

Specifically, in a case where a water-absorbing agent is handled in an industrial manner, a means to heat a hopper for preserving the water-absorbing agent, a conveyor line for the water-absorbing agent, and a quantitative feeder and the like and keep them hot is typically used in order to prevent the water-absorbing agent from absorbing moisture. These are usually heated and kept at a temperature of 30° C. to 80° C.

Many of the conventional additives such as polyethylene glycol and surfactants, used to improve powder properties, particularly flowability, of a water-absorbing agent in a moistened state or in a state in which the moisture content is 0 mass % to less than 20 mass %, typically have a low melting point or a low glass-transition temperature. Therefore, even if the flowability of the water-absorbing agent is excellent at room temperature, the additives melt due to heat coming from the production apparatus, conveyor line, and the like, and the water-absorbing agent as powder decreases in flowability and handleability, during, for example, production of the water-absorbing agent and a disposable diaper. On the contrary, according to the present invention, an organic acid polyvalent metal salt having a melting point falling within the above range is used; therefore, the water-absorbing agent, when heated, does not decrease in industrial handleability.

Note that, with regard to the melting point of the organic acid polyvalent metal salt, a measured melting point may be employed or a melting point disclosed in, for example, Chemical Unabridged Dictionary (*KAGAKU DAIJITEN*) (edited by Editorial Board for Chemical Unabridged Dictionary (*Kagaku Daijiten Henshu Iinkai*), issued by KYORITSU SHUPPAN CO., LTD.) or the like may be employed. For example, zinc stearate has a melting point of 128° C. to 130° C., aluminum stearate has a melting point of 103° C., calcium stearate has a melting point of 180° C., and magnesium stearate has a melting point of 200° C. As such, these organic acid polyvalent metal salts each have a melting point appropriate for use in a particulate water-absorbing agent of the present invention, and therefore are suitably used. Furthermore, an appropriate selection of an organic acid polyvalent metal salt to use makes it possible to adjust the melting point in a wide range. Note, however, that, in practice, it is preferable to select and use an organic acid polyvalent metal salt having a melting point that is equal to or above the temperature at which the particulate water-absorbing agent of the present invention is used.

The organic acid polyvalent metal salt is preferably poorly soluble or insoluble in deionized water at 25° C. For example, the organic acid polyvalent metal salt has a solubility of preferably 0 g/L or more and 10 g/L or less, more preferably 0 g/L or more and 5 g/L or less, even more preferably 0 g/L or more and 2 g/L or less, relative to 1000 mL of deionized water. An organic acid polyvalent metal salt having a solubility of more than 10 g/L is not preferred, because such an organic acid polyvalent metal salt may flow into an absorbed liquid such as urine or blood, as described earlier.

(2-2-9) Step of Adding Multicomponent Metal Compound

A method for producing a particulate water-absorbing agent in accordance with the present invention includes: a surface-crosslinking step; and a step of adding multicomponent metal compound (hereinafter may be referred to as "multicomponent metal compound addition step") including adding, to polyacrylic acid (salt)-based water-absorbing resin powder, a multicomponent metal compound in an amount of 0.01 mass % to 5 mass %, preferably 0.01 mass % to 3 mass %, more preferably 0.01 mass % to 1 mass %. The multicomponent metal compound has a hydrotalcite structure and contains two kinds of cation, i.e., divalent and trivalent metal cations, and a hydroxyl group.

In the multicomponent metal compound addition step, it is preferable that the water-absorbing resin powder and the multicomponent metal compound are dry-mixed, and it is more preferable that the surface-crosslinking step is carried out prior to and/or subsequently to the multicomponent metal compound addition step.

A preferred embodiment of a water-absorbing agent in accordance with the present invention contains the multicomponent metal compound in an amount of 0.01 mass % to 5 mass %, more preferably 0.01 mass % to 3 mass %, even more preferably 0.01 mass % to 1 mass %, and has a moisture absorption blocking ratio of 0 mass % to 30 mass %. A preferred embodiment of a water-absorbing agent in accordance with the present invention is produced by the above method and has a moisture absorption blocking ratio of 0 mass % to 30 mass %. Such a water-absorbing agent has high water absorption performance.

A multicomponent metal compound in accordance with the present invention not only is capable of reducing the amount of water-absorbing agent dust composed of the multicomponent metal compound and water-absorbing resin powder, but also has the ability to reduce the amount of dust that would increase because of the addition of inorganic fine particles other than the multicomponent metal compound. In addition, there is no need to use a third component, e.g., water, to add the multicomponent metal compound, and therefore the production process is simplified and also there is no need to take the effects of the third component into consideration. Furthermore, the multicomponent metal compound simply dry-mixed with the powder is highly adherent to the powder, and, in addition, the multicomponent metal compound itself, even in a small amount, provides a high moisture absorption blocking effect. This, in turn, prevents or reduces the loss of water absorption performance.

The water-absorbing agent containing the multicomponent metal compound is less likely to generate dust, less likely to cause moisture absorption blocking, and has high water absorption performance. This prevents or reduces worsening of work environment that would be caused by, for example, flying dust, in the process for producing the water-absorbing agent and in the process for producing an absorbent body using the water-absorbing agent.

(1. Multicomponent Metal Compound)

A multicomponent metal compound in accordance with the present invention is a multicomponent metal compound that contains two kinds of cation, i.e., divalent and trivalent metal cations, and a hydroxyl group, and further, causes no or little reduction in water absorption performance such as AAP of the water-absorbing agent and has the function of preventing or reducing moisture absorption blocking.

Examples of the divalent metal cation include $Mg^{2+}$, $Fe^{2+}$, $Zn^{2+}$, $Ca^{2+}$, $Ni^{2+}$, $Co^{2+}$, and $Cu^{2+}$, and, from the viewpoint of heat resistance and the like, $Mg^{2+}$ is preferred. Examples of the trivalent metal cation include $Al^{3+}$, $Fe^{3+}$, and $Mn^{3+}$, and, from the viewpoint of heat resistance and the like, $Al^{3+}$ is preferred. Therefore, in a preferred embodiment of the multicomponent metal compound, a divalent metal cation is magnesium cation, and a trivalent metal cation is aluminum cation.

The multicomponent metal compound preferably has a hydrotalcite-like structure that is represented by the following general formula (1) and that is known as a structure of a layered compound:

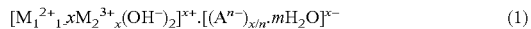

$$[M_1^{2+}{}_{1-x}M_2^{3+}{}_x(OH^-)_2]^{x+}\cdot[(A^{n-})_{x/n}\cdot mH_2O]^{x-} \quad (1)$$

where $M_1^{2+}$ represents a divalent metal cation, $M_2^{3+}$ represents a trivalent metal cation, $A^{n-}$ represents an n-valent anion, and $H_2O$ represents water.

With regard to the proportions of the divalent and trivalent metal cations in the general formula (1), x is preferably within the range of from 0.2 to 0.75, more preferably within the range of from 0.25 to 0.7, even more preferably within the range of from 0.25 to 0.5. Examples of the anion include $OH^-$, $F^-$, $Cl^-$, $Br^-$, $NO_3$—, $CO_3^{2-}$, $SO_4^{2-}$, $Fe(CN)_6^{3-}$, $CH_3COO$—, oxalate ion, and salicylate ion, and a preferred anion is carbonate anion. Furthermore, m in the general formula (1) is a number greater than 0. It is more preferable that $0<m\leq10$.

The multicomponent metal compound is not limited to any particular form, and can have a spherical form (including a powder form). The multicomponent metal compound preferably has a specific particle size. A volume average particle diameter is preferably 2 μm or less, more preferably 1.5 μm or less, even more preferably 1 μm or less. If the particle diameter is large, it is then necessary to add a large amount of the multicomponent metal compound in order to sufficiently obtain a dust reduction effect. This may impair the water absorption performance of a water-absorbing agent to be obtained. If the particle diameter is excessively small, then workability may decrease during the step of adding the multicomponent metal compound, and/or it may be impossible to obtain sufficient performance. Therefore, the volume average particle diameter is preferably 0.05 μm or more, more preferably 0.1 μm or more, even more preferably 0.3 μm or more. Note that the volume average particle diameter of the dust reducer can be measured by a "laser diffraction scattering method" (for example, measured using a particle size analyzer Microtrac MT3000II (product name) manufactured by NIKKISO CO., LTD.). The average particle diameter of the multicomponent metal compound adhering to the surface of a water-absorbing resin can be measured by a measuring method in which a scanning electron microscope (SEM) is used. This method will be described in Examples.

The multicomponent metal compound can further have an organic compound intercalated between layers thereof and/ or can be surface-treated so that the mixability with a resin or the like improves.

Examples of a preferable structural formula of the multicomponent metal compound include $Mg_6Al_2(OH)_{16}CO_3\cdot4H_2O$ and $Mg_4Al_2(OH)_{12}CO_3\cdot3H_2O$. Specifically, examples of a preferable structural formula of the multicomponent metal compound include DHT-4H and DHT-6 manufactured by Kyowa Chemical Industry Co., Ltd., STABIACE HT-1-NC and STABIACE HT-P manufactured by SAKAI CHEMICAL INDUSTRY CO., LTD.

Although a multicomponent metal compound may or may not be surface-treated, the multicomponent metal compound is more preferably not surface-treated. Specific examples of a surface-treating agent for use in the surface treatment include the following (a) through (j).

(a) Higher fatty acids such as stearic acid, oleic acid, erucic acid, palmitic acid, and lauric acid.

(b) Metal salts such as lithium salts, sodium salts, and potassium salts of any of the higher fatty acids (a) above.

(c) Anionic surfactants such as sulfate ester salts of higher alcohols (e.g., stearyl alcohol and oleyl alcohol), sulfate ester salts of polyethylene glycol ether, amide-bound sulfate ester salts, ether-bound sulfonates, ester-bound sulfonates, amide-bound alkyl aryl sulfonates, and ether-bound alkyl aryl sulfonates.

(d) The following phosphate esters: monoesters containing orthophosphoric acid, oleyl alcohol, stearyl alcohol, or the like; diesters containing orthophosphoric acid, oleyl alcohol, stearyl alcohol, or the like; and mixtures thereof, each of which is of an acid type, an alkali metal salt, an amine salt, or the like.

(e) Silane coupling agents such as vinylethoxysilane, γ-methacryloxypropyl trimethoxysilane, vinyltris(2-methoxyethoxy)silane, and γ-aminopropyl trimethoxysilane.

(f) Titanium coupling agents such as isopropyltriisostearoyl titanate, isopropyltris(dioctylpyrophosphate)titanate, and isopropyl tridecyl benzenesulfonyl titanate.

(g) Alkali coupling agents such as acetoalkoxyaluminum diisopropylate.

(h) Ethanolamines such as monoethanolamine, diethanolamine, and triethanolamine.

(i) n-propanolamines such as n-propanolamine, di-n-propanolamine, and tri-n-propanolamine.

(j) Isopropanolamines such as monoisopropanolamine, diisopropanolamine, and triisopropanolamine.

Among these, ethanolamines such as monoethanolamine, diethanolamine, and triethanolamine are preferable.

(2-2-10) Step of Adding Another Additive

In the present invention, an additive other than the above described additives can be added in order to give various functions to the water-absorbing resin Specifically, examples of such an additive include surfactants, compounds having a phosphorus atom, oxidizers, organic reducing agents, water-insoluble inorganic fine particles, organic powder such as metallic soap, deodorants, antibacterial agents, pulp, thermoplastic fibers, and the like. Note that the surfactant can be any of compounds disclosed in International Publication No. 2005/075070 in the present invention. Moreover, the water-insoluble inorganic fine particles can be any of compounds disclosed in "[5] Water-insoluble inorganic fine particles" of International Publication No. 2011/040530 in the present invention.

The amount of the additive used (added) is determined as appropriate according to a purpose of the additive, and is therefore not limited to a particular one. The amount used (added) of the additive is preferably 3 parts by weight or less, more preferably 1 part by weight or less, relative to 100 parts by weight of the water-absorbing resin powder. It is also possible to add the additive during a step other than the above step.

(2-2-11) Other Steps

In the present invention, in addition to the above described steps, it is possible to carry out a granulation step, a sizing step, a fine powder removal step, a fine powder recycling step, and the like according to need. Moreover, it is possible to further carry out one or more of a transportation step, a storing step, a packing step, a preserving step, and the like. Note that the "sizing step" encompasses a fine powder removal step subsequent to the surface-crosslinking step and a step of carrying out classification and pulverization in a case where a water-absorbing resin is aggregated to have a size larger than an intended size. The "fine powder recycling step" encompasses an aspect in which classified fine powder is added as-is before the classification step (especially, a polymerization step and/or gel-crushing step), and also a step of adding the fine powder, granulated into the form of a hydrogel having a larger particle diameter, during any of the steps for producing the water-absorbing resin.

[2-3] Physical Properties of Particulate Water-Absorbing Agent

In a case where the polyacrylic acid (salt)-based water-absorbing agent produced by the method in accordance with the present invention is used for a sanitary material (especially a disposable diaper), it is desirable to control at least one of the physical properties of (2-3-1) to (2-3-10), preferably two or more of the physical properties, including the AAP, of (2-3-1) to (2-3-10); more preferably three or more of the physical properties, including the AAP, of (2-3-1) to (2-3-10); and most preferably all of the physical properties of (2-3-1) to (2-3-10), such that the physical properties each fall within a desired range. Having physical properties which do not satisfy the below ranges may prevent sufficiently achieving effects of the present invention and achieving sufficient performance in a high-concentration disposable diaper.

The polyacrylic acid (salt)-based particulate water-absorbing agent produced by the method in accordance with the present invention is not limited to any particular shape, but is preferably particulate. In this section, physical properties of a particulate water-absorbing agent or a water-absorbing resin are discussed. The physical properties below are measured in conformity with EDANA method unless otherwise specified.

(2-3-1) CRC (Fluid Retention Capacity without Pressure)

The particulate water-absorbing agent of the present invention has a CRC (fluid retention capacity without pressure) of 30 g/g to 50 g/g, preferably 31 g/g to 50 g/g, 32 g/g to 50 g/g, 33 g/g to 50 g/g, 34 g/g to 50 g/g, 35 g/g to 50 g/g, 36 g/g to 50 g/g, 30 g/g to 49 g/g, 30 g/g to 48 g/g, 30 g/g to 47 g/g, 30 g/g to 46 g/g, 30 g/g to 45 g/g, 30 g/g to 44 g/g, 30 g/g to 43 g/g, 30 g/g to 42 g/g, 30 g/g to 41 g/g, 30 g/g to 40 g/g, 30 g/g to 39 g/g, or 30 g/g to 38 g/g.

If the CRC is less than 5 g/g, then an absorption amount is small. This renders a particulate water-absorbing agent unsuitable as an absorbent body of a sanitary material such as a disposable diaper. If the CRC is more than 70 g/g, then a rate at which, for example, a body fluid such as urine or blood is absorbed decreases. This renders a particulate water-absorbing agent unsuitable for use in, for example, a disposable diaper having a high water absorption speed. Note that CRC can be controlled with use of, for example, an internal crosslinking agent and/or a surface-crosslinking agent.

(2-3-2) Gel CRC

The CRC (gel CRC), before gel-crushing, of a hydrogel is preferably 33 g/g or more. A gel CRC before gel-crushing of less than 10 g/g or of more than 45 g/g is not preferable because it becomes difficult to control the particle shape and the particle size distribution during the gel-crushing. In order to achieve such a gel CRC, an added amount of crosslinking agent during polymerization, polymerization concentration, or the like may be controlled as appropriate. Note that it is a well-known fact that a particulate water-absorbing agent or a water-absorbing resin preferably has a high gel CRC. It was, however, found in the present invention that a gel CRC of more than 45 g/g makes it difficult to control the particle shape and the particle size distribution.

(2-3-3) Fluid Retention Capacity Under Pressure 0.7 Psi (AAP0.7)

The particulate water-absorbing agent in accordance with the present invention has a fluid retention capacity under pressure (AAP) of preferably 15 g/g or more, more preferably 18 g/g or more, even more preferably 20 g/g or more, particularly preferably 22 g/g or more, most preferably 24 g/g or more. The upper limit value of the AAP is not limited to any particular value, but is preferably 30 g/g or less.

If the AAP0.7 is less than 15 g/g, then the amount of liquid returning from an absorbent body when a pressure is exerted on the absorbent body (such an amount of liquid is usually called "re-wet") is large. This means that such a particulate water-absorbing agent is unsuitable as an absorbent body of a sanitary material such as a disposable diaper. Note that AAP can be controlled by controlling particle size, surface-crosslinking agent, or the like.

(2-3-4) Particle Size (Particle Size Distribution, Weight Average Particle Diameter (D50), and Logarithmic Standard Deviation ($\sigma\zeta$) of Particle Size Distribution)

The particulate water-absorbing agent of the present invention has a particle size (a particle size distribution, a weight average particle diameter (D50), and a logarithmic standard deviation ($\sigma\zeta$) of the particle size distribution) which is controlled so as to be the same as the particle size of the water-absorbing resin powder before being subjected to surface crosslinking.

(2-3-5) Residual Monomer

From the viewpoint of safety, the water-absorbing agent in accordance with the present invention contains residual monomers in an amount of preferably 500 ppm or less, more preferably 400 ppm or less, even more preferably 300 ppm or less. A lower limit is not particularly limited but is preferably 0 ppm, and more preferably approximately 10 ppm.

Controlling the amount of residual monomers to fall within the above ranges makes it possible to obtain a water-absorbing agent which causes less irritation to, for example, skin of a human body.

(2-3-6) Saline Flow Conductivity (SFC)

The particulate water-absorbing agent of the present invention has a saline flow conductivity (SFC) of preferably less than 70 ($\times 10^{-7} \cdot cm^3 \cdot s \cdot g^{-1}$), more preferably less than 60 ($\times 10^{-7} \cdot cm^3 \cdot s \cdot g^{-1}$), even more preferably less than 50 ($\times 10^{-7} \cdot cm^3 \cdot s \cdot g^{-1}$), particularly preferably less than 40 ($\times 10^{-7} \cdot cm^3 \cdot s \cdot g^{-1}$).

(2-3-7) Moisture Absorption Blocking Ratio (B.R.)

A specific method of measuring (evaluating) a moisture absorption blocking ratio (B.R.) will be described later, but the moisture absorption blocking ratio (B.R.) of the particulate water-absorbing agent of the present invention is preferably 0 weight % to 50 weight %, more preferably 0 weight % to 40 weight %, even more preferably 0 weight % to 30 weight %, and most preferably 0 weight % to 10 weight %. If the moisture absorption blocking ratio (B.R.) is more than 50 weight %, then the particulate water absorbing agent is difficult to handle in humid conditions. This may pose a problem that, during production of a thin absorbent body for hygienic material, for example, the particulate water-absorbing agent aggregates in a transport pipe in a production plant and therefore the transport pipe clogs and/or the particulate water-absorbing agent cannot be uniformly mixed with hydrophilic fibers.

(2-3-8) Gel-Grinding Energy (GGE)

The upper limit value of the gel grinding energy (GGE) for gel-crushing of a hydrogel in the present invention is preferably 60 [J/g] or less, more preferably 50 [J/g] or less, even more preferably 40 [J/g] or less, and the lower limit value of the gel-grinding energy (GGE) is preferably 15 [J/g] or more, more preferably 17 [J/g] or more, even more preferably 20 [J/g] or more, still even more preferably 23 [J/g] or more, most preferably 25 [J/g] or more. For example, in the present invention, the gel-grinding energy (GGE) for gel-crushing of a hydrogel is 18 [J/g] to 60 J/g, preferably 20 [J/g] to 50 [J/g], even more preferably 25 [J/g] to 40 [J/g]. By controlling the GGE within the above range, it is possible to perform gel-crushing while applying adequate shearing and compressive forces to the hydrogel. It is noted that the gel-grinding energy (GGE) includes the energy that the gel-crusher consumes in the idle state.

The gel grinding energy for gel-crushing may be alternatively specified by the gel grinding energy (2) (GGE(2) also referred to as "net gel grinding energy"), which excludes the energy that the gel-crusher consumes in the idle state. Specifically, in the present invention, the upper limit of the gel grinding energy (2) (GGE (2)) for gel-crushing of the hydrogel is preferably 40 [J/g] or less, more preferably 38 [J/g] or less, even more preferably 35 [J/g] or less, and the lower limit of the gel grinding energy (2) (GGE (2)) is preferably 9 [J/g] or more, more preferably 12 [J/g] or more, even more preferably 15 [J/g] or more. For example, in the present invention, the gel grinding energy (2) (GGE (2)) for gel-crushing of the hydrogel is 9 [J/g] to 40 [J/kg], preferably 12 J/g to 38 [J/g], more preferably 15 J/g to 35 [J/g]. By controlling the GGE (2) within the above range, it is possible to perform gel-crushing while applying adequate shearing and compressive forces to the hydrogel.

(2-3-9) Shape of Particulate Water-Absorbing Agent

Figure 2:
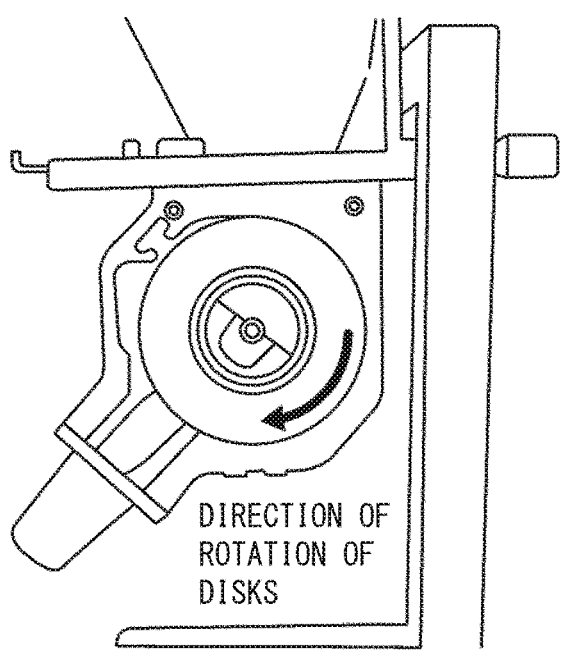
FIG. 2 is a side view of the feeder of FIG. 1. The arrow indicates the direction of rotation of one or more drive disks in a housing of the feeder.

In general, examples of the shape of a water-absorbing agent include: spherical and/or ellipsoidal primary particles and sausage-shaped primary particles which are obtained by reversed phase suspension polymerization disclosed in FIGS. 1 and 2 of U.S. Pat. No. 5,244,735; granulated versions of spherical and/or ellipsoidal primary particles, such as particles agglomerated together, e.g., agglomerated beads as disclosed in FIG. 1 on page 75 of NON WOVENS WORLD October-November 2000 (published by Marketing Technology Service, Inc.); and non-uniformly pulverized shape derived from crushing a hydrogel polymer obtained via polymerization of an aqueous monomer solution, such as crystals disclosed in FIGS. 2, 3, and 4 of U.S. Pat. No. 5,981,070 and FIG. 1 on page 75 of the foregoing NON WOVENS WORLD October-November 2000, and granulated versions thereof.

A particulate water-absorbing agent in accordance with the present invention is in the form other than the form of spherical primary particles, and is preferably also in the form other than the form of oval spherical (ellipsoidal) primary particles, more preferably in the form of particles having a non-uniformly pulverized shape derived from granulating spherical particles or ellipsoidal particles. Alternatively, the particulate water-absorbing agent is more preferably in the form of particles having a non-uniformly pulverized shape derived from crushing a hydrogel polymer obtained via polymerization of an aqueous monomer solution or in the form of a granulated version thereof. The particulate water-absorbing agent is particularly preferably in the form of particles having a non-uniformly pulverized shape or in the form of a granulated version thereof.

Spherical primary particles and/or ellipsoidal primary particles are not preferred because, when an absorbent article or the like is produced, a particulate water-absorbing agent cannot be well mixed with a fiber material such as pulp and easily falls off an absorbent body which is a mixture of the particulate water-absorbing agent and the fiber material. As such, when a water-absorbing agent in the form of spherical primary particles and/or ellipsoidal primary particles is used, the water-absorbing agent cannot be uniformly distributed within the absorbent body easily.

(2-3-10) Powder Properties of Particulate Water-Absorbing Agent

A particulate water-absorbing agent in accordance with the present invention is poor in adhesion, has a small coefficient of internal friction or a small angle of internal friction and thus has a small angle of repose, and therefore is in a powder from that shows excellent flowability not only in a moistened state and gel state but also in a dry state in which the moisture content is 0 mass % to 20 mass %, even in which the moisture content is 0 mass % to 10 mass %. The coefficient of internal friction and the angle of internal friction can be found by a shear test on particle layers. The shear test on powder can be carried out with use of an apparatus such as a shear-box apparatus, a ring-shear apparatus, or a parallel-plate apparatus, examples of which include a Jenike Shear Cell.

It is generally known that spherical primary particles and/or ellipsoidal primary particles obtained by a reversed phase suspension polymerization have high flowability. On the other hand, even in cases of particles having "non-uniform" shape (i.e., particles having a shape that is not spherical primary particles and that is not oval spherical primary particles) (e.g., particles having non-uniformly pulverized shape produced by an aqueous solution polymerization or particles obtained by, after a reversed phase suspension polymerization, granulating such spherical primary particles and/or ellipsoidal primary particles), the powder flowability of such particles is such that, due to their non-uniform shape, the coefficient of internal friction is high and flowability is very low.

Therefore, the above water-absorbing agent composed of particles having a high coefficient of internal friction incurs increases in transport resistance during air flow conveyance, transport resistance during conveyance using a paddle-type conveyor, and transport resistance during conveyance using a screw-type conveyor. That is, according to conventional techniques, when handling particles having a "non-uniform" shape (i.e., shape other than spherical primary particles and other than oval spherical primary particles), a production apparatus and a conveyor are clogged with such a water-absorbing agent, thus causing excessive load and resulting in frequent halts of these apparatuses.

Furthermore, conventionally, addition of an inorganic substance to a water-absorbing agent is generally carried out in order to ensure flowability in a moistened environment. A water-absorbing agent having such an inorganic substance added thereto is poor in flowability in a dry state, particularly in a dry state in which the moisture content is 0 mass % to 20 mass %. This results in increases in frequency of clogging of the production apparatus and conveyor with the water-absorbing agent and frequency of halts of such apparatuses due to excessive load.

However, a particulate water-absorbing agent in accordance with the present invention, which contains the foregoing water-absorbing resin and polyvalent metal salt of an organic acid, shows very high flowability as powder (hereinafter "powder flowability") in a tightly packed state, even when the particulate water-absorbing agent has a shape other than the shape of spherical primary particles and other than the shape of oval spherical primary particles.

Furthermore, the organic acid polyvalent metal salt contained in the particulate water-absorbing agent obtained in the present invention has a high melting point, and therefore, as described earlier, the particulate water-absorbing agent can be heated and kept hot. Even when heated and kept hot, the particulate water-absorbing agent can achieve substantially the same level of powder flowability as at room temperature.

As such, the particulate water-absorbing agent in accordance with the present invention has improved flowability both in a moistened state and in a powdery state, and also achieves very high flowability. The particulate water-absorbing agent in accordance with the present invention also shows high powder flowability when in its dry state, and therefore makes it possible to alleviate mechanical damage and thereby prevent or reduce reductions in absorption capacity under load and moisture absorption flowability which would result from mechanical damage.

As such, the particulate water-absorbing agent in accordance with the present invention has high powder flowability as described above. Therefore, use of the particulate water-absorbing agent is effective in simplification of a hopper, a powder storage tank, and the like for use in a process for producing an absorbent body or the like.

[2-4] Applications of Particulate Water-Absorbing Agent

Applications of the particulate water-absorbing agent of the present invention are not particularly limited. However, the particulate water-absorbing agent is preferably used in, for example, an absorbent body of sanitary materials which are absorbent articles such as disposable diapers, sanitary napkins, and incontinence pads. In particular, the water-absorbing agent of the present invention can be used for an absorbent body in high-concentration disposable diapers (i.e., disposable diapers each of which contains a large amount of the water-absorbing agent), which have heretofore had problems such as odor, caused by a raw material, and coloring. Further, in a case where the water-absorbing agent of the present invention is used as an upper layer part of the absorbent body, a significant effect can be expected.

An absorbent article in accordance with the present invention is an absorbent article which includes: an absorbent body which includes a water-absorbing agent and which is obtained by optionally shaping hydrophilic fibers into a sheet form; a liquid-permeable front sheet; and a liquid-impermeable back sheet. The absorbent body, if the hydrophilic fibers are not used, is formed by fixing a water-absorbing agent to paper and/or nonwoven fabric. The absorbent article in accordance with the present invention, in particular, a disposable diaper for babies, a disposable diaper for adults, or a sanitary napkin, can be produced by, for example: preparing an absorbent body (absorbent core) by blending a fiber base material and a water-absorbing agent in accordance with the present invention and/or sandwiching a water-absorbing agent in accordance with the present invention by fiber base materials; sandwiching the absorbent core by a liquid-permeable material (front sheet) and a liquid-impermeable material (back sheet); and, as necessary, providing an elastic member, diffusion layer, adhesive tape, and/or the like.

The amount of the water-absorbing agent contained in the absorbent body of the absorbent article (such an amount is referred to as "core concentration") is preferably 10 mass % or more, more preferably 20 mass % or more, particularly preferably 30 mass % or more, particularly preferably 70 mass % or more. The absorbent body is preferably pressed and shaped to a density of 0.06 g/cc or more and 0.50 g/cc or less and a basis weight of 0.01 $g/cm^2$ or more and 0.20 $g/cm^2$ or less. Examples of the fiber base material that can be used include hydrophilic fibers such as wood-ground pulp, cotton linter, crosslinked cellulose fibers, rayon, cotton, wool, acetate, and vinylon. Those obtained by air-laying these fibers are preferred.

Alternatively, as the absorbent body, it is possible to use an absorbent material such as a pulp fiber, in addition to the particulate water-absorbing agent. In such a case, the amount (core concentration) of the particulate water-absorbing agent contained in the absorbent body is preferably 30 weight % to 100 weight %, more preferably 40 weight % to 100 weight %, still more preferably 50 weight % to 100 weight %, further still more preferably 60 weight % to 100 weight %, particularly preferably 70 weight % to 100 weight %, and most preferably 75 weight % to 95 weight %.

In a case where the core concentration falls within the above range and the absorbent body is used as an upper layer part of an absorbent article, the absorbent article can maintain cleanness, i.e., a state of being white. Further, in such a case, the absorbent article is excellent in diffusion property with respect to a body fluid or the like such as urine or blood, and therefore improvement in absorption amount can be expected based on efficient liquid distribution.

Furthermore, a particulate water-absorbing agent in accordance with the present invention can be used in various fields including, but not limited to, sheets for pets and waterproofing materials.

[1-5] Overview of Feeder

A feeder for use in the present invention is a feeder which is a volumetric or weight feeding apparatus for solid materials, and includes one or more drive disks therein. The one or more drive disks enable efficient feeding or efficient conveyance of solid materials. Examples of such a feeder include positive displacement pumps. A more preferred example is a feeder using a bulk solid pump (Bulk Solids Pump™, BSP) manufactured by Coperion K-tron. The feeder used in the present invention may be referred to as, for example, "bulk materials pump feeder".

A positive displacement pump is of a type that pushes a fluid from the sucking side to the discharge side utilizing a displacement of the volume of an enclosed space between a casing and a movable portion that is in contact with the inside of the casing. A pump of this type is capable of easily obtaining very high pressure. Furthermore, the amount of discharge therefrom is substantially proportional to the number of rotations, and changes only to a very small extent in response to changes in load.

The positive displacement pump, in general, means a conveyor apparatus for liquids; however, a bulk solid pump is one in which its system is adapted also for solids (see Coperion K-tron's webpage: https://www.coperion.com/en/products-services/process-equipment/feeders/bulk-solids-pump-feeders-bsp/ (visited on Apr. 3, 2017)). Therefore, a BSP is classified as a positive displacement pump. Note that the term "bulk solids" is a general term that refers to solid material in bulk, bulk solid, solid in bulk, or the like. The "Bulk Solids Pump™" is the name of a product manufactured by Coperion K-tron, which is a Coperion K-tron's original conveyor apparatus for solids with flowability. Note, however, that, although the BSP is a product name, it is generally known as the name of a conveyor apparatus for solids (see Handbook of Filters (page-281, 3-9 Feeding)). Also note that information such as the principle of material supply is available on Coperion K-tron's webpage (https://www.coperion.com/en/products-services/process-equipment/feeders/bulk-solids-pump-feeders-bsp/ (visited on Apr. 3, 2017)) and apte Inc.'s webpage (http://apte.jp/product/ktron/bsp.html (visited on Apr. 3, 2017)).

The feeder used in the present invention is more preferably a loss-in quantitative feeder (loss-in weight feeder) (also called "loss-in-weight type feeder"). As used herein, the term "loss-in" refers to a system in which: a feeder (supplying apparatus) integrally configured with a stock tank, in its entirety, is placed on a metering device; flow rate is detected from a loss in weight per unit time; and feed rate (discharge amount) is automatically controlled so that the detected flow rate matches a set value. Note that it is also preferable that, in the feeder used in the present invention, the bulk solid pump is included in such a loss-in system.

According to an aspect of the present invention, a feeder used in the present invention includes its housing and a drive rotor, configured such that the housing has an inlet, an outlet, and an inner wall that extends from the inlet to the outlet, the drive rotor has
  (a) a hub rotatable about a rotation axis and
  (b) a plurality of drive disks having a periphery and extending from the hub toward the inner wall of the housing, and the inner wall of the housing, the drive disks, and the hub define a materials transfer duct through which material is transferred from the inlet of the housing to the outlet of the housing.

According to another aspect of the present invention, the drive rotor further includes:

(c) means disposed on the periphery of the drive disks for sealing the area between the periphery of the drive disks and the inner wall of the housing.

In an embodiment, the drive disks are configured such that the distance between the circumferential edges of the drive disks and the inner wall of the housing increases from the inlet of the housing to the outlet of the housing in the direction of rotation of the drive rotor.

In an embodiment, the sealing means includes a low-friction brush seal, and the brush seal is made of pipe cleaner. The low-friction brush seal is important to avoid an extra load on a drive motor. Furthermore, the addition of the brush seal does not introduce tolerance issues into the design of the feeder.

In an embodiment, the sealing means (brush seal) is attached to the drive disks using an adhesive. The sealing means (brush seal) is attached to the periphery of the drive disks in a manner as shown in, for example, the topmost one of the disks in FIG. 3 (hatched portion).

Figure 3:
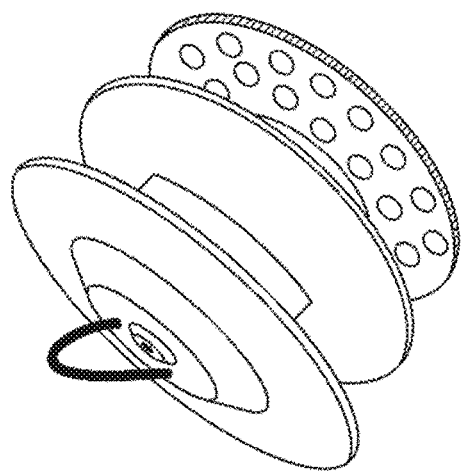
FIG. 3 is a perspective view of an example of a set of a plurality of drive disks included in the feeder of FIG. 1.

In an embodiment, the drive disks have a channel formed in their periphery, and the sealing means (brush seal) is disposed in the channel. In another embodiment, the drive disks have textured interior faces. As illustrated in FIG. 3, the interior faces of the drive disks can have other features that give such face texture. The textural features such as dimples (represented by a plurality of ovals in the topmost disk in FIG. 3) increase the friction between the drive disks and the material handled by the feeder. Such friction facilitates movement of the material through the materials transfer duct. Because optimal performance of the materials transfer duct depends on a consistent, linear relationship between the material conveying speed and the speed of the feeder, slippage should be avoided. Some friction between the drive disks and the material handled by the feeder avoids slippage and helps to assure a linear speed of materials delivery.

According to another aspect of the present invention, the feeder further includes a materials scraper which
  (a) is mounted in the housing,
  (b) extends into the drive rotor between the drive disks, and
  (c) has a flexible tip preventing material handled by the feeder from either flowing backward to a discharge point proximate the outlet of the housing or jamming between the drive disks and the materials scraper.

Certain materials that are transferred through the feeder will cling, under certain conditions, to the drive rotor, and such clinging material may not be discharged through the outlet. The materials scraper scrapes clinging material from the drive rotor and, generally, this material falls back and is discharged successfully through the outlet. The function of the materials scraper is to scrape materials handled by the feeder from the drive disks and the hub as the materials exit the feeder. For many materials, such scraping is unnecessary. The materials scraper is especially adapted for those applications which require no or only a minimal amount of scraping.

In an embodiment, the housing further has a recess in the inner wall downstream from the outlet of the housing and upstream from the inlet of the housing relative to the direction of rotation of the drive motor, and the materials scraper is mounted in the recess.

In an embodiment, the materials scraper also has a number of scraping tips. In another embodiment, the materials scraper also has a continuous scraping surface.

In an embodiment, the hub has a textured surface. In another embodiment, the drive disks have textured interior faces.

According to a further aspect of the present invention, the feeder further includes (c) a brush seal disposed on the periphery of the drive disks for sealing the area between the periphery of the drive disks and the inner wall of the housing and for preventing materials handled by the feeder from wedging between the periphery of the drive disks and the inner wall of the housing.

According to still a further aspect of the present invention, the feeder further includes (c) a brush seal disposed on the periphery of the drive disks for sealing the area between the periphery of the drive disks and the inner wall of the housing and for preventing materials handled by the feeder from wedging between the periphery of the drive disks and the inner wall of the housing, the brush seal inducing no friction between the drive disks and the inner wall of the housing.

According to still a further aspect of the present invention, the feeder further includes a materials scraper for scraping materials from the drive disks, the materials scraper
(a) being mounted in the housing and
(b) extending into the drive rotor between the drive disks.

In an embodiment, the materials scraper has a flexible tip preventing material handled by the feeder from either flowing backward from the outlet of the housing or jamming between the drive disks and the materials scraper, the flexible tip projecting from the materials scraper to the drive disks.

In an embodiment, the hub has a surface that induces friction between the hub and materials.

In an embodiment, the drive disks have interior faces that induce friction between the drive disks and materials.

In an embodiment, the flexible tip is conductive.

In an embodiment, the inner wall is spiral shaped, defined by the equation "R=θ×a" (where R is the radius, θ is the polar angle, and a is the rate of radial increase).

In an embodiment, the materials scraper further has a scraping surface proximate the hub, and the distance between the scraping surface and the hub increases in the direction of rotation of the drive rotor.

In an embodiment, the brush seal is a member to prevent or reduce the possibility of materials from entering the region between the periphery of the drive disks and the inner wall of the housing.

In an embodiment, the brush seal is in contact with the inner wall between the inlet and the outlet of the materials transfer duct.

In an embodiment, at least one of the plurality of drive disks has a molded elastic portion. In another embodiment, the drive rotor further includes at least one drive disk that includes no elastic portions.

In an embodiment, at least one of the plurality of drive disks has a different structure from that of another one of the drive disks. For example, as illustrated in FIG. 3, at least one of the drive disks has, in the circumferential edge thereof, a brush seal and/or dimple, but another one of the drive disks does not have any brush seal or dimple.

In an embodiment, two of the plurality of drive disks are outer drive disks having a first structure, and at least one additional drive disk is an inner drive disk having a second structure different from the first structure.

The following three structural features of the feeder reduce the tendency of material to jam between the drive rotor and the housing or other stationary parts mounted to the housing. First, the distance between the circumferential edges of the drive disks and the inner wall of the housing increases from the inlet to the outlet in the direction of rotation of the drive rotor. Second, a low-friction brush seal disposed on the periphery of the drive disks seals the area between the periphery of the drive disks and the inner wall. Finally, a materials scraper having a flexible tip is mounted in the housing and extends into the drive rotor between the drive disks. The inner wall of the housing, the drive disks, and the hub define a materials transfer duct through which material is transferred from the inlet of the housing to the outlet of the housing. The three features of the feeder can be independently incorporated in the feeder in accordance with the present invention. Alternatively, any two or all three of the features can be combined into a single feeder. At least for certain application, such combination may be expected to achieve a synergistic effect.

In the feeder used in the present invention, the drive rotor is rotated by a motor coupled to the drive rotor by a suitable mechanism. As the drive rotor is rotated, the drive disks cause material, introduced into the feeder through the inlet of the housing, to be transferred to the outlet of the housing where the material is discharged from the feeder.

The distance between the circumferential edges of the drive disks and the inner wall of the housing increases from the inlet of the housing to the outlet of the housing in the direction of rotation of the drive rotor, which is clockwise as indicated by the arrow in FIG. 2. The drive disks and the inner wall of the housing can be shaped in different ways to provide a desired spacing between the two components. As illustrated in FIG. 3, the drive disks are circular and extend away from the hub perpendicular to the rotation axis of the hub, and the inner wall of the housing is spiral shaped. The spiral-shaped inner wall of the housing can be defined by the Archimedes spiral equation:

$$R=\theta \times a,$$

where "R" is the radius, "θ" is the polar angle, and "a" is the rate of radial increase given in some unit of measure per angular unit, such as mm/degree. Material transferred through the feeder does not wedge because of the increasing distance between the circumferential edges of the drive disks and the inner wall of the housing.

Figure 4:
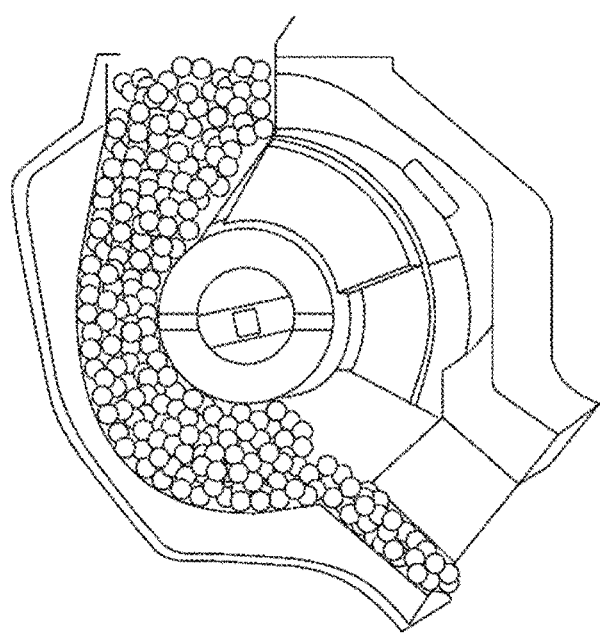
FIG. 4 is a cross-sectional view of the feeder of FIG. 1, for illustrating the principle of material supply.

The principle of material supply of the feeder used in the present invention is as follows. As illustrated in FIG. 4, particles of material, introduced through the inlet at the upper portion, gather and are thereby, due to the friction of the material, brought into "lock-up" condition. The material is conveyed through the materials transfer duct to the outlet as the disks rotate, the "lock-up" condition is cleared, and the material is discharged through the outlet. The material may be discharged through the outlet after the "lock-up" state of the particles of the material is cleared or concurrently with the clearing of the "lock-up" condition of the particles of the material.

[2-6] Description of Preferred Embodiments

Preferred embodiments of the present invention will be described below. It is to be understood that the embodiments described below are provided for better understanding of the present invention, and the scope of the present invention should not be limited to the descriptions below. It is therefore clear that a person skilled in the art can make modifications as appropriate within the scope of the present invention in view of the descriptions in the present specification. It is also to be understood that each of the below embodiments of the present invention can be used individually or in combination with another/other embodiment(s).

(2-6-1) Method of Continuously Feeding Particulate Water-Absorbing Agent

According to an aspect, the present invention provides a method of continuously feeding, with use of a feeder, a water-absorbing agent containing a water-absorbing resin (SAP) as a main component, the feeder including a housing and a drive rotor,
the housing having an inlet, an outlet, and an inner wall that extends from the inlet to the outlet,
the drive rotor having
(a) a hub rotatable about a rotation axis and
(b) a plurality of drive disks having a periphery and extending from the hub toward the inner wall of the housing, the inner wall of the housing, the plurality of drive disks, and the hub defining a materials transfer duct through which material is transferred from the inlet of the housing to the outlet of the housing, the water-absorbing agent satisfying K-index≥70, the K-index being defined by the following equation:

$$K\text{-index}=100-(-438+3.6\times\text{angle of repose}+3.5\times\text{angle of difference}+7.9\times\text{compressibility rate}+290\times\text{bulk density (EDANA method)}).$$

According to another aspect, the present invention provides a method of continuously feeding, with use of a feeder, a water-absorbing agent containing a water-absorbing resin (SAP) as a main component, the feeder including a housing and a drive rotor, the housing having an inlet, an outlet, and an inner wall that extends from the inlet to the outlet, the drive rotor having (a) a hub rotatable about a rotation axis and (b) a plurality of drive disks having a periphery and extending from the hub toward the inner wall of the housing, the inner wall of the housing, the plurality of drive disks, and the hub defining a materials transfer duct through which material is transferred from the inlet of the housing to the outlet of the housing, the water-absorbing agent satisfying K-index≥70, the K-index being defined by the following equation:

$$K\text{-index}=100-(-438+3.6\times\text{angle of repose}+3.5\times\text{angle of difference}+7.9\times\text{compressibility rate}+290\times\text{bulk density (EDANA method)}),$$ and the water-absorbing agent satisfying at least one of the following (i) and (ii):

(i) the water-absorbing agent has a bulk density falling within the range of from 0.5 to 0.9, has a compressibility rate of 5 to 20, and has an angle of repose of 25° to 45° and/or an angle of difference of 2° to 20°;

(ii) the water-absorbing agent contains a polyvalent metal salt of an organic acid or contains a multicomponent metal compound, the polyvalent metal salt containing seven or more carbon atoms, the multicomponent metal compound having a hydrotalcite structure and containing divalent and trivalent metal cations and a hydroxyl group.

According to still a further aspect, the present invention provides a method of continuously feeding, with use of a feeder, a water-absorbing agent containing a water-absorbing resin (SAP) as a main component, the method being arranged such that particles of the water-absorbing agent, introduced through an inlet of the feeder, gather and are thereby, due to a friction of the water-absorbing agent, brought into a "lock-up" condition, the water-absorbing agent is conveyed through a materials transfer duct to an outlet as disks rotate, the "lock-up" condition is cleared, and the water-absorbing agent is discharged through the outlet, the water-absorbing agent satisfying K-index≥70, the K-index being defined by the following equation:

$$K\text{-index}=100-(-438+3.6\times\text{angle of repose}+3.5\times\text{angle of difference}+7.9\times\text{compressibility rate}+290\times\text{bulk density (EDANA method)}).$$

According to still a further aspect, the present invention provides a method of continuously feeding, with use of a feeder, a water-absorbing agent containing a water-absorbing resin (SAP) as a main component, the method being arranged such that particles of the water-absorbing agent, introduced through an inlet of the feeder, gather and are thereby, due to a friction of the water-absorbing agent, brought into a "lock-up" condition, the water-absorbing agent is conveyed through a materials transfer duct to an outlet as disks rotate, the "lock-up" condition is cleared, and the water-absorbing agent is discharged through the outlet, the water-absorbing agent satisfying K-index≥70, the K-index being defined by the following equation:

$$K\text{-index}=100-(-438+3.6\times\text{angle of repose}+3.5\times\text{angle of difference}+7.9\times\text{compressibility rate}+290\times\text{bulk density (EDANA method)}),$$ and the water-absorbing agent satisfying at least one of the following (i) and (ii):

(i) the water-absorbing agent has a bulk density falling within the range of from 0.5 to 0.9, has a compressibility rate of 5 to 20, and has an angle of repose of 25° to 45° and/or an angle of difference of 2° to 20°;

(ii) the water-absorbing agent contains a polyvalent metal salt of an organic acid or contains a multicomponent metal compound, the polyvalent metal salt containing seven or more carbon atoms, the multicomponent metal compound having a hydrotalcite structure and containing divalent and trivalent metal cations and a hydroxyl group.

Figure 9:
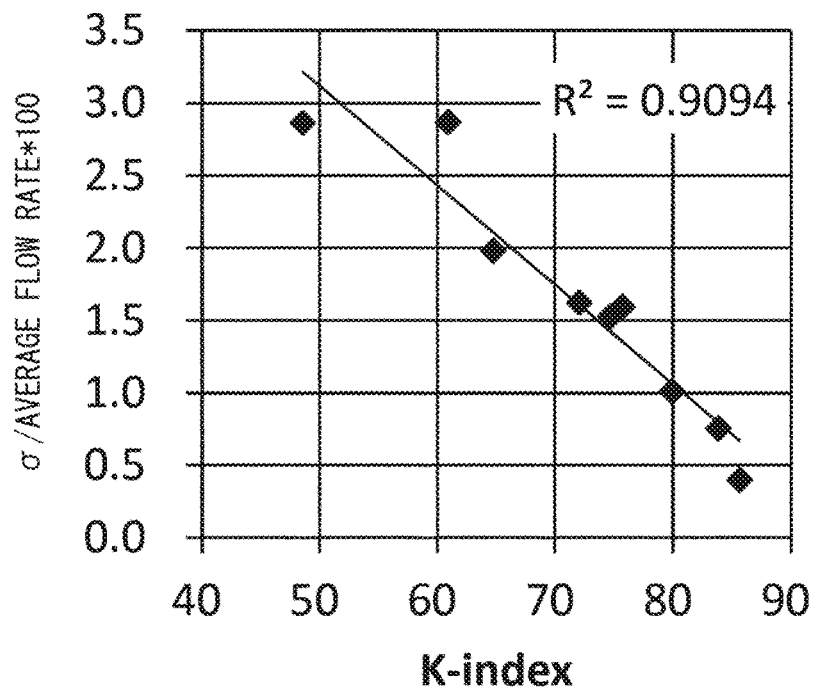
FIG. 9 is a chart showing "(σ/average flow rate)×100" plotted against K-index, with regard to water-absorbing agents of the present invention and comparative water-absorbing agents.

In an embodiment of the present invention, the K-index of the water-absorbing agent is preferably K-index≥70, more preferably K-index≥75 or K-index≥80. In a case where K-index≥70, the value of "(σ/average flow rate)×100" is low and is 2.0 or less, as shown in FIG. 9. That is, when K-index≥70, the value of "σ", which is the standard deviation of the rate (feed rate) at which the water-absorbing agent is fed from the feeder, is small. Without wishing to be bound by any theory, cases where K-index are preferred because there is a tendency that fluctuation of the amount of the water-absorbing agent fed from the feeder per unit time is small and a bulk material can be supplied more stably. Cases where K-index≥75 or K-index≥80 are more preferred, because the tendency of stable supply becomes more noticeable. The upper limit of the K-index is, for example, 150, preferably 120, more preferably 110, particularly preferably 100, most preferably 95.

Note, here, that the parameters of the water-absorbing agent, employed when calculating the K-index, may be any values obtained by a measurement method known in this field or may be values represented or available from some other information source. Alternatively, a water-absorbing agent whose measured or calculated parameters are presented by a supplier may be purchased and used as appropriate. For example, with regard to the bulk density (EDANA method), a water-absorbing agent whose bulk density (EDANA method) is presented by a SAP manufacturer may be purchased and used as appropriate.

In another embodiment of the present invention, the method further includes a step of, based on the above K-index, selecting, as the water-absorbing agent for use in the feeder, a water-absorbing agent satisfying K-index≥70. In a further embodiment of the present invention, the method further includes a step of, based on the above K-index, selecting, from a plurality of water-absorbing agents, a water-absorbing agent that is for use in the feeder and that causes no or little fluctuation of feed amount per unit time. Without wishing to be bound by any theory, this is because, by selecting a water-absorbing agent satisfying the condition K-index≥70 before feeding a water-absorbing agent, it is possible to successfully feed, with use of the feeder, the water-absorbing agent at a stable feed rate.

The "fluctuation" of the feed amount per unit time (i.e., feed rate), with regard to the water-absorbing agent, is defined by the value of "(σ/average flow rate)×100" (unit: %). As used herein, the value "σ" (unit: g/min) indicates the standard deviation of the feed rate. Specifically, the value σ can be obtained according to a method (A) of continuous feeding using a bulk solid pump (BSP) discussed later in the <Measurement method> section. A smaller value of "(σ/average flow rate)×100" means a smaller fluctuation. The value of "(σ/average flow rate)×100" is preferably 1.95 or less, 1.90 or less, 1.80 or less, 1.70 or less, 1.60 or less, 1.50 or less, 1.40 or less, 1.30 or less, 1.20 or less, 1.10 or less, 1.00 or less, 0.90 or less, more preferably 0.80 or less.

According to still a further aspect, the present invention provides a method of continuously feeding, with use of a feeder, a water-absorbing agent containing a water-absorbing resin (SAP) as a main component, the feeder including a housing and a drive rotor, the housing having an inlet, an outlet, and an inner wall that extends from the inlet to the outlet, the drive rotor having (a) a hub rotatable about a rotation axis and (b) a plurality of drive disks having a periphery and extending from the hub toward the inner wall of the housing, the inner wall of the housing, the plurality of drive disks, and the hub defining a materials transfer duct through which material is transferred from the inlet of the housing to the outlet of the housing, the water-absorbing agent satisfying "probe insertion work PIW≤30000 gf×mm", the probe insertion work PIW being a work done when an insertion member is inserted to a predetermined depth in the water-absorbing agent.

According to still a further aspect, the present invention provides a method of continuously feeding, with use of a feeder, a water-absorbing agent containing a water-absorbing resin (SAP) as a main component, the feeder including a housing and a drive rotor, the housing having an inlet, an outlet, and an inner wall that extends from the inlet to the outlet, the drive rotor having (a) a hub rotatable about a rotation axis and (b) a plurality of drive disks having a periphery and extending from the hub toward the inner wall of the housing, the inner wall of the housing, the plurality of drive disks, and the hub defining a materials transfer duct through which material is transferred from the inlet of the housing to the outlet of the housing, the water-absorbing agent satisfying "probe insertion work PIW≤30000 gf×mm", the probe insertion work PIW being a work done by an insertion member inserted to a predetermined depth in the water-absorbing agent, the water-absorbing agent satisfying at least one of the following (i) and (ii):

(i) the water-absorbing agent has a bulk density falling within the range of from 0.5 to 0.9, has a compressibility rate of 5 to 20, and has an angle of repose of 25° to 45° and/or an angle of difference of 2° to 20°;

(ii) the water-absorbing agent contains a polyvalent metal salt of an organic acid or contains a multicomponent metal compound, the polyvalent metal salt containing seven or more carbon atoms, the multicomponent metal compound having a hydrotalcite structure and containing divalent and trivalent metal cations and a hydroxyl group.

According to still a further aspect, the present invention provides a method of continuously feeding, with use of a feeder, a water-absorbing agent containing a water-absorbing resin (SAP) as a main component, the method being arranged such that particles of the water-absorbing agent, introduced through an inlet of the feeder, gather and are thereby, due to a friction of the water-absorbing agent, brought into a "lock-up" condition, the water-absorbing agent is conveyed through a materials transfer duct to an outlet as disks rotate, the "lock-up" condition is cleared, and the water-absorbing agent is discharged through the outlet, the water-absorbing agent satisfying "probe insertion work PIW≤30000 gf×mm", the probe insertion work PIW being a work done by an insertion member inserted to a predetermined depth in the water-absorbing agent.

According to still a further aspect, the present invention provides a method of continuously feeding, with use of a feeder, a water-absorbing agent containing a water-absorbing resin (SAP) as a main component, the method being arranged such that particles of the water-absorbing agent, introduced through an inlet of the feeder, gather and are thereby, due to a friction of the water-absorbing agent, brought into a "lock-up" condition, the water-absorbing agent is conveyed through a materials transfer duct to an outlet as disks rotate, the "lock-up" condition is cleared, and the water-absorbing agent is discharged through the outlet, the water-absorbing agent satisfying "probe insertion work PIW≤30000 gf×mm", the probe insertion work PIW being a work done by an insertion member inserted to a predetermined depth in the water-absorbing agent.

the water-absorbing agent satisfying at least one of the following (i) and (ii):

(i) the water-absorbing agent has a bulk density falling within the range of from 0.5 to 0.9, has a compressibility rate of 5 to 20, and has an angle of repose of 25° to 45° and/or an angle of difference of 2° to 20°;

(ii) the water-absorbing agent contains a polyvalent metal salt of an organic acid or contains a multicomponent metal compound, the polyvalent metal salt containing seven or more carbon atoms, the multicomponent metal compound having a hydrotalcite structure and containing divalent and trivalent metal cations and a hydroxyl group.

In an embodiment of the present invention, the method further includes a step of, based on the above PIW, selecting, as the water-absorbing agent for use in the feeder, a water-absorbing agent satisfying PIW≤30000 gf×mm. In a further embodiment of the present invention, the method further includes a step of, based on the above PIW, selecting, from a plurality of water-absorbing agents, a water-absorbing agent that is for use in the feeder and that causes no or little fluctuation of feed amount per unit time. Without wishing to be bound by any theory, this is because, by selecting a water-absorbing agent satisfying PIW≤30000 gf×mm before feeding a water-absorbing agent, it is possible to successfully feed, with use of the feeder, the water-absorbing agent at a stable feed rate.

In a preferred embodiment of the present invention, use of the probe insertion work PIW as an additional indicator in addition to the K-index makes it possible to achieve accurate feeding of the water-absorbing agent with a stable feed rate. It is preferable here that the water-absorbing agent satisfies K-index≥70 and probe insertion work PIW≤30000 gf×mm.

In an embodiment of the present invention, it is preferable that the feeder used is the feeder discussed in the foregoing "[5] Overview of feeder" section. Without wishing to be bound by any theory, when the feeder for use in the present invention is used to convey a water-absorbing agent having a specific performance, the feed rate is stable (fluctuation of amount of flow per unit time is small), and therefore the water-absorbing agent can be fed stably; this is preferred. The fluctuation of feed amount per unit time (i.e., feed rate) is defined by "($\sigma$/average flow rate)×100" where $\sigma$ represents the standard deviation of the feed rate. The value of "($\sigma$/average flow rate)×100" is 1.95 or less.

In an embodiment of the present invention, it is preferable that the water-absorbing agent is fed and conveyed at a temperature equal to or below the glass-transition temperature (Tg) of the water-absorbing agent, for the following reason: it is known that a water-absorbing agent is elastomeric (in the form of a gel) at temperatures equal to and above Tg, and, at temperatures equal to and above Tg, the water-absorbing agent is difficult to feed or convey; and therefore the water-absorbing agent needs to be fed or conveyed at a temperature and a moisture content controlled such that the temperature of the water-absorbing agent is equal to or below Tg. The Tg of the water-absorbing agent is related to temperature and moisture content. The temperature is preferably within the range of from, for example, 0° C. to 80° C., 5° C. to 70° C., or 10° C. to 60° C., more preferably, for example, room temperature (20° C. to 25° C.), most preferably, for example, 23.5° C. The moisture content is preferably within the range of from, for example, 0.5 weight % to 15 weight % or 1 weight % to 10 weight %.

In an embodiment of the present invention, the polyvalent metal salt of an organic acid, containing seven or more carbon atoms, is selected from the group consisting of calcium laurate, magnesium laurate, zinc laurate, aluminum laurate, calcium myristate, magnesium myristate, aluminum myristate, zinc myristate, calcium palmitate, magnesium palmitate, aluminum palmitate, zinc palmitate, calcium stearate, magnesium stearate, zinc stearate, and aluminum stearate. The polyvalent metal salt is preferably selected from calcium stearate, magnesium stearate, zinc stearate, and aluminum stearate, more preferably is zinc stearate. In a preferred embodiment, the polyvalent metal salt of an organic acid, containing seven or more carbon atoms, is contained in an amount of 0.001 mass % or more and less than 10 mass %, preferably 0.01 mass % or more and less than 5 mass %, even more preferably 0.05 mass % or more and less than 2 mass %, particularly preferably 0.1 mass % or more and less than 1 mass %, relative to the water-absorbing resin.

In a particulate water-absorbing agent in accordance with the present invention, the organic acid of the "polyvalent metal salt of an organic acid" is preferably a fatty acid. In the water-absorbing agent in accordance with the present invention, a polyvalent metal of the "polyvalent metal salt of an organic acid" is preferably an alkaline earth metal and/or a divalent or more transition metal. In the particulate water-absorbing agent in accordance with the present invention, it is preferable that the polyvalent metal salt of an organic acid has a melting point of 40° C. to 250° C. and has a solubility, in 1 L of deionized water 1 L at 25° C., of 0 g/L or more and 5 g/L or less. It is also preferable that the polyvalent metal salt of an organic acid in the particulate water-absorbing agent in accordance with the present invention adheres to the surface of the water-absorbing resin.

In another embodiment, the multicomponent metal compound, having a hydrotalcite structure and containing divalent and trivalent metal cations and a hydroxyl group, is selected from the group consisting of $Mg_6Al_2(OH)_{16}CO_3 \cdot 4H_2O$ and $Mg_4Al_2(OH)_{12}CO_3 \cdot 3H_2O$. Specific examples include DHT-4H and DHT-6 manufactured by Kyowa Chemical Industry Co., Ltd., and STABIACE HT-1-NC and STABIACE HT-P manufactured by SAKAI CHEMICAL INDUSTRY CO., LTD. In a preferred embodiment, the amount of the multicomponent metal compound added is preferably 0.01 mass % to 5 mass %, more preferably 0.01 mass % to 4.5 mass %, even more preferably 0.1 mass % to 4.5 mass %, even more preferably 0.1 mass % to 4 mass %, particularly preferably 0.15 mass % to 3.5 mass %, relative to the water-absorbing resin powder. When the amount of the multicomponent metal compound added is less than 0.01 mass %, it may be impossible to achieve a sufficient dust reduction effect. Even if the multicomponent metal compound is added in an amount more than 5 mass %, the obtained dust reduction effect is not worth the amount added. As such, the amount of the multicomponent metal compound contained in the final absorbing agent in accordance with the present invention is defined as described above; however, because the amount of the multicomponent metal compound added is small relative to the water-absorbing agent, the amount of the multicomponent metal compound contained in the absorbing agent is also substantially 0.01 mass % to 5 mass %.

(2-6-2) Method for Producing Absorbent Article with Use of Water-Absorbing Agent, Method of Preparing "Feed"

According to an aspect, the present invention provides a method for producing an absorbent article with use of a water-absorbing agent containing a water-absorbing resin (SAP) as a main component, the method including:

a step of continuously feeding the water-absorbing agent with use of a feeder; and a step of producing an absorbent article with use of the water-absorbing agent thus fed, the feeder including a housing and a drive rotor and being a bulk materials pump feeder in which the housing has an inlet, an outlet, and an inner wall that extends from the inlet to the outlet, the drive rotor has
 (a) a hub rotatable about a rotation axis and
 (b) a plurality of drive disks having a periphery and extending from the hub toward the inner wall of the housing, and the inner wall of the housing, the plurality of drive disks, and the hub define a materials transfer duct through which material is transferred from the inlet of the housing to the outlet of the housing, the water-absorbing agent satisfying K-index≥70, the K-index being defined by the following equation:

$$K\text{-index}=100-(-438+3.6\times\text{angle of repose}+3.5\times\text{angle of difference}+7.9\times\text{compressibility rate}+290\times\text{bulk density (EDANA method)}).$$

According to another aspect, the present invention provides a method for producing an absorbent article with use of a water-absorbing agent containing a water-absorbing resin (SAP) as a main component, the method including:

a step of continuously feeding the water-absorbing agent with use of a feeder; and a step of producing an absorbent article with use of the water-absorbing agent thus fed, the feeder including a housing and a drive rotor and being a feeder in which the housing has an inlet, an outlet, and an inner wall that extends from the inlet to the outlet, the drive rotor has
 (a) a hub rotatable about a rotation axis and
 (b) a plurality of drive disks having a periphery and extending from the hub toward the inner wall of the housing, and the inner wall of the housing, the plurality of drive disks, and the hub define a materials transfer duct through which material is transferred from the inlet of the housing to the outlet of the housing, the water-absorbing agent satisfying "probe insertion work PIW≤30000 gf×mm", the probe insertion work PIW being a work done by an insertion member inserted to a predetermined depth in the water-absorbing agent.

According to a further aspect, the present invention provides a method for producing an absorbent article with use of a water-absorbing agent containing a water-absorbing resin (SAP) as a main component, the method including:

a step of continuously feeding the water-absorbing agent with use of a feeder; and a step of producing an absorbent article with use of the water-absorbing agent thus fed, the feeder being arranged such that particles of the water-absorbing agent, introduced through an inlet of the feeder, gather and are thereby, due to a friction of the water-absorbing agent, brought into a "lock-up" condition, the water-absorbing agent is conveyed through a materials transfer duct to an outlet as disks rotate, the "lock-up" condition is cleared, and the water-absorbing agent is discharged through the outlet, the water-absorbing agent satisfying K-index≥70, the K-index being defined by the following equation:

$$K\text{-index}=100-(-438+3.6\times\text{angle of repose}+3.5\times\text{angle of difference}+7.9\times\text{compressibility rate}+290\times\text{bulk density (EDANA method)}).$$

According to still a further aspect, the present invention provides a method for producing an absorbent article with use of a water-absorbing agent containing a water-absorbing resin (SAP) as a main component, the method including:

a step of continuously feeding the water-absorbing agent with use of a feeder; and a step of producing an absorbent article with use of the water-absorbing agent thus fed, the feeder being arranged such that particles of the water-absorbing agent, introduced through an inlet of the feeder, gather and are thereby, due to a friction of the water-absorbing agent, brought into a "lock-up" condition, the water-absorbing agent is conveyed through a materials transfer duct to an outlet as disks rotate, the "lock-up" condition is cleared, and the water-absorbing agent is discharged through the outlet, the water-absorbing agent satisfying "probe insertion work PIW≤30000 gf×mm", the probe insertion work PIW being a work done by an insertion member inserted to a predetermined depth in the water-absorbing agent.

In a preferred embodiment of the present invention, use of the probe insertion work PIW as an additional indicator in addition to the K-index makes it possible to achieve accurate feeding of the water-absorbing agent with a stable feed rate. It is preferable here that the water-absorbing agent satisfies K-index≥70 and probe insertion work PIW≤30000 gf×mm.

According to still a further aspect, the present invention provides a method of preparing, in a feeder, a certain amount of a "feed" of a water-absorbing agent containing a water-absorbing resin (SAP) as a main component such that the feed rate of the "feed" falls within a certain deviation range, the method including a step of continuously feeding the water-absorbing agent with use of the feeder by any of the methods described in the foregoing "(2-6-1) Method of continuously feeding particulate water-absorbing agent" section.

(2-6-3) Preferred Method for Producing Particulate Water-Absorbing Agent

According to an aspect, the present invention includes the following features (1) and (2).

(1) The average of dimensions of gels is 3000 μm or more, 5000 μm or more, 10 mm or more, 30 mm or more, 10 cm or more, 50 cm or more, 100 cm or more.

(2) Gel CRC is 33.0 g/g or more, 34.0 g/g or more, 35.0 g/g or more, 36.0/g or more, 37.0 g/g or more, 38.0 g/g or more, 39.0 g/g or more, 40.0 g/g or more. The upper limit of the gel CRC is 45.0 g/g.

In a case where a gel has the above features (1) and (2), the present invention further has the following features (3) and (4).

(3) Gel-grinding energy (GGE) is 20 [J/g] to 60 [J/g], preferably 24 [J/g] to 55 [J/g], more preferably 28 [J/g] to 50 [J/g].

(4) Gel-grinding energy (2) (GGE(2)) is 9 [J/g] to 40 [J/g], preferably 12 [J/g] to 38 [J/g], more preferably 15 [J/g] to 35 [J/g].

An aspect of the present invention provides a method for producing a particulate water-absorbing agent including carrying out gel-crushing by applying an energy to the gel, the energy satisfying at least one of the above features (3) and (4).

Note here that the foregoing "dimension" of a gel refers to the distance between two points most spaced apart from each other on a surface of the gel (so-called long diameter).

Conventional methods for producing a particulate water-absorbing agent do not involve crushing a high-CRC gel (having a gel CRC of 33 g/g or more) with use of a high gel-grinding energy (GGE of 18 [J/g] or more). In the present invention, a hydrogel after polymerization is subjected to crushing (gel-crushing) with use of a gel-grinding energy higher than that used in the conventional methods, so that the shapes of the particles of a particulate water-absorbing agent is controlled physically rather than chemically. This enables an increase in water absorption speed. This makes it possible to produce a particulate water-absorbing agent which achieves both a high fluid retention capacity and a high water absorption speed and further achieves a reduction in re-wet as compared with a conventional particulate water-absorbing agent.

According to conventional methods for producing a water-absorbing agent, control of particle shape and particle size distribution by gel-crushing with a high gel-grinding energy was difficult at a gel CRC of 33 or more. (This is because the gel has a decreased crosslinking density and softens at a gel CRC of 33 or more.) Through diligent study, however, the inventors of the present invention discovered that increasing the moisture content of the gel (reducing the solid content) so as to further lower the strength of the gel allows the particle shape and the particle size distribution to be controlled easily by gel-crushing, even in a case where the gel has a high CRC (a gel CRC of 33 or more).

In a preferred embodiment, (5) moisture content is 50 weight % or more, 51 weight % or more, 52 weight % or more, 53 weight % or more, 55 weight % or more, 60 weight % or more, 70 weight % or more, 90 weight % or less.

A preferred embodiment is characterized in that (a) the gel-crushing is performed until a gel obtained has a particle diameter of 360 μm to 1500 μm, (b) the gel having a weight of 10 kg/m$^2$ to 50 kg/m$^2$ per unit area of band drying is dried for 10 hours to 60 hours at a drying temperature of 150° C. to 200° C. and an air velocity of hot air of 0.8 m/s to 2.5 m/s, preferably 0.003 m/s to 0.1 m/s, even more preferably 0.005 m/s to 0.06 m/s in a vertical direction (an up-and-down direction), and (c) the gel thus dried is subjected to a surface treatment. This allows producing a particulate water-absorbing agent which has characteristics such as (1) being less prone to undergo gel blocking (formation of an aggregate of particles of a particulate water-absorbing agent) even when the particulate water-absorbing agent absorbs liquid, (2) having an increased elastic modulus of swollen gel and an enhanced water absorbing power under load, and (3) having a good resistance to moisture absorption blocking.

According to a preferred embodiment, the method for producing a particulate water-absorbing agent includes a step of adding a chelating agent in an amount of 0.001 parts by weight to 0.2 parts by weight, preferably 0.003 parts by weight to 0.1 parts by weight, more preferably 0.005 parts by weight to 0.06 parts by weight, relative to 100 parts by weight of the particulate water-absorbing agent or the water-absorbing resin. Addition of the chelating agent to the particulate water-absorbing agent enables an improvement in urine resistance of the particulate water-absorbing agent.

According to a preferred embodiment, the chelating agent is selected from the group consisting of iminodiacetic acid, hydroxyethyl iminodiacetic acid, nitrilotriacetic acid, nitrilotri propionic acid, ethylenediaminetetraacetic acid, hydroxy ethylenediamine triacetic acid, hexamethylenediamine tetraacetic acid, diethylenetriamine pentaacetic acid (DTPA), triethylenetetramine hexaacetic acid, trans-1,2-diaminocyclohexane tetraacetic acid, bis(2-hydroxyethyl)glycine, diaminopropanol tetraacetic acid, ethylenediamine-2-propionic acid, glycol ether diaminetetraacetic acid, bis(2-hydroxybenzyl)ethylenediamine diacetic acid, 3-hydroxy-2,2-iminodisuccinic acid, iminodisuccinic acid, methylglycine diacetic acid, ethylenediamine-N,N'-di(methylene phosphinic acid), ethylenediaminetetra(methylene phosphinic acid), nitriloacetic acid-di(methylene phosphinic acid), nitrilodiacetic acid-(methylene phosphinic acid), nitriloacetic acid-β-proprionic acid-methylene phosphonate, nitrilotris(methylene phosphonate), cyclohexanediaminetetra(methylene phosphonate), ethylenediamine-N,N'-diacetic acid-N,N'-di(methylene phosphonate), ethylenediamine-N,N'-di(methylene phosphonate), polymethylenediaminetetra (methylene phosphonate), diethylenetriaminepenta(methylene phosphonate), and 1-hydroxyethylidenediphosphonic acid. Adding any of the chelating agents above to a particulate water-absorbing agent allows for an improvement in urine resistance of the particulate water-absorbing agent.

According to a preferred embodiment, the production method further includes a step of adding a moisture absorption flowability improving agent in an amount of 0.01 parts by weight to 1.0 part by weight, preferably 0.02 parts by weight to 0.7 parts by weight, and even more preferably 0.03 parts by weight to 0.5 parts by weight, relative to 100 parts by weight of the particulate water-absorbing agent or the water-absorbing resin. In a case where the conditions above are satisfied, the moisture absorption flowability of the particulate water-absorbing agent is improved. This makes it possible to decrease the adhesion of the particulate water-absorbing agent to equipment when an absorbent body is produced with use of the particulate water-absorbing agent and a fiber base material.

According to a preferred embodiment, the moisture absorption flowability improving agent is selected from the group consisting of silicon dioxide, hydrotalcite, phosphates, and aluminum salts. Adding the moisture absorption flowability improving agent improves the moisture absorption flowability of the particulate water-absorbing agent. This makes it possible to decrease the adhesion of the particulate water-absorbing agent to equipment when an absorbent body is produced with use of the particulate water-absorbing agent and a fiber base material.

(2-6-4) Correlation Equation for K-Index

In the present invention, parameters calculated based on measurement carried out on a water-absorbing agent, and equivalent parameters thereof, were studied closely. As a result, it was found that the following equation is most appropriate:

$$K\text{-index}=100-(-438+3.6\times\text{angle of repose}+3.5\times\text{angle of difference}+7.9\times\text{compressibility rate}+290\times\text{bulk density (EDANA method)}),$$

and therefore the equation was employed.

The above "equivalent parameters" refer to parameters that can be derived from the foregoing parameters or refer to parameters indicating substantially the same properties as those indicated by the foregoing parameters although the names of the parameters are different (for example, the parameter "bulk density" can be used substantially synonymously with "bulk density" and "apparent specific gravity"). Errors that are derived when such equivalent parameters are used are tolerated. Alternatively, a water-absorbing agent intrinsically having the properties indicated by these parameters may be purchased and used as appropriate. Alternatively, a water-absorbing agent, whose parameters are measured or calculated and are presented by a supplier may be purchased and used as appropriate. For example, a water-absorbing agent, whose bulk density (EDANA method) is presented by a SAP manufacturer, may be purchased and used as appropriate. As such, in an embodiment of the present invention, the scope of the correlation equation (K-index) includes variations in which the equivalent parameters of a water-absorbing agent containing a water-absorbing resin as a main component are used. Specifically, the scope of the correlation equation (K-index) includes variations which are different from the correlation equation (K-index) in that one or more of the four parameters (selected from the group consisting of bulk density, compressibility rate, angle of repose, and angle of difference), which are used in the correlation equation (K-index), of a water-absorbing agent containing a water-absorbing resin as a main component is/are replaced by an equivalent parameter(s).

In another embodiment of the present invention, the scope of the correlation equation (K-index) includes variations in which one or more but not all of the parameters of a water-absorbing agent containing a water-absorbing resin (SAP) as a main component is/are used. Specifically, the scope of the correlation equation (K-index) includes variations in which at least one, at least two, or at least three of the four parameters (selected from the group consisting of bulk density, compressibility rate, angle of repose, and angle of difference), which are used in the correlation equation (K-index), of a water-absorbing agent containing a water-absorbing resin (SAP) as a main component is/are used. The scope of the correlation equation (K-index) also includes variations in which one or more of these parameter(s) is/are replaced by an equivalent parameter(s).

In a preferred embodiment, preferred ranges (upper limits and lower limits) of the parameters in the correlation equation (K-index) are as below. It should be understood that every combination of an upper limit and a lower limit of each of the parameters, and any value between the upper limit and the lower limit (the upper limit and the lower limit inclusive), are encompassed in the scope of the present invention.

Bulk density (EDANA method): Examples of preferred lower limit include 0.5 g/mL, 0.53 g/mL, 0.55 g/mL, and 0.57 g/mL, and examples of preferred upper limit include 0.9 g/mL, 0.85 g/mL, 0.82 g/mL, and 0.80 g/mL.

Compressibility rate: Examples of preferred lower limit include 5%, 7%, 9%, and 10%, and examples of preferred upper limit include 20%, 18%, 16%, and 14%.

Angle of repose: Examples of preferred lower limit include 25°, 27°, 29°, and 30°, and examples of preferred upper limit include 45°, 43°, 41°, and 40°.

Angle of difference: Examples of preferred lower limit include 2°, 5°, 6°, and 8°, and examples of preferred upper limit include 20°, 18°, 16°, and 15°.

Figure 10:
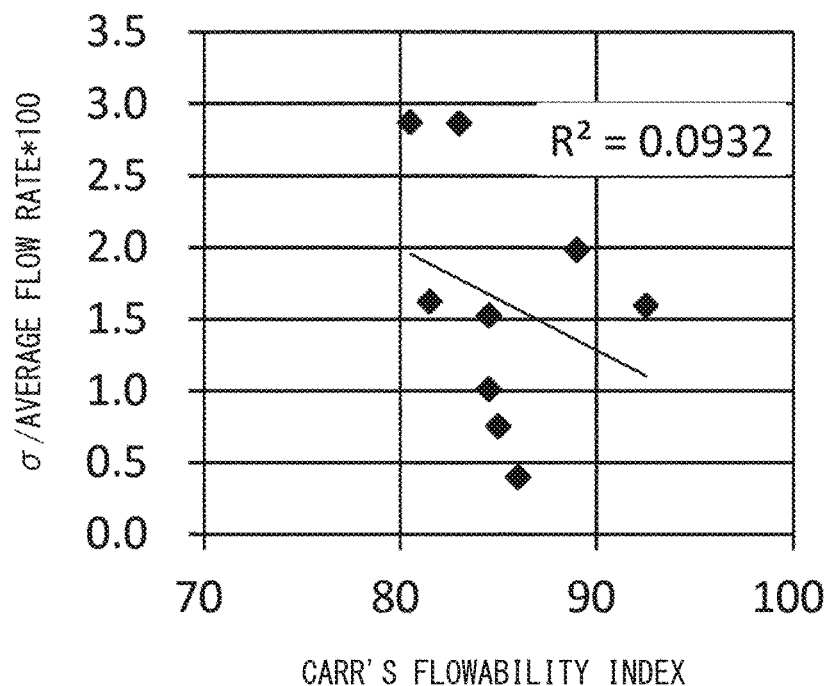
FIG. 10 is a chart showing "(σ/average flow rate)×100" plotted against Carr's flowability index, with regard to the water-absorbing agents of the present invention and the comparative water-absorbing agents.
Figure 12:
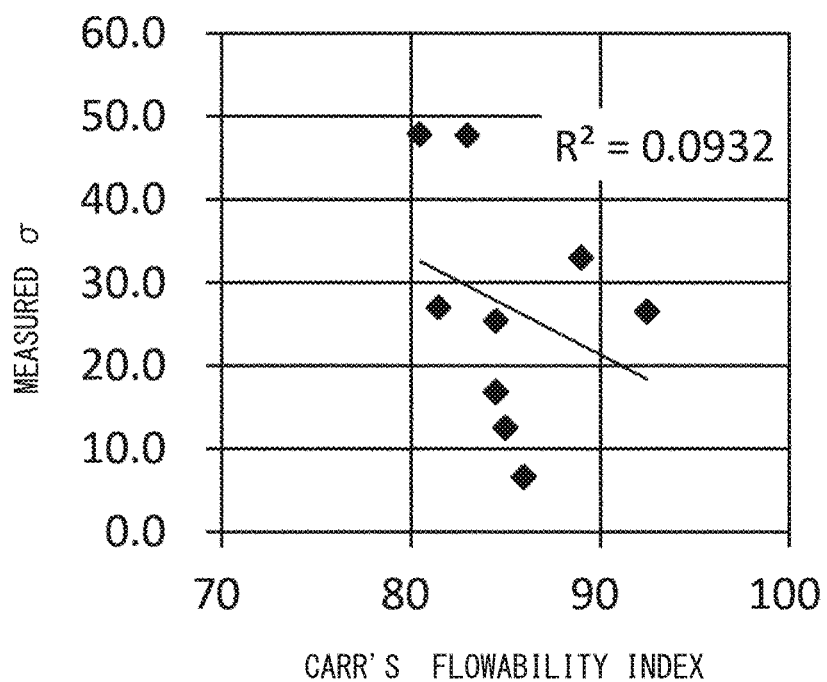
FIG. 12 is a chart showing the value σ plotted against Carr's flowability index, with regard to the water-absorbing agents of the present invention and the comparative water-absorbing agents.

Note that the Carr's flowability index can be calculated using parameters of a water-absorbing agent. However, with regard to the water-absorbing agent in accordance with the present invention, there appeared no correlation between the value σ and the Carr's flowability index, and the Carr's flowability index was found to be inappropriate as an indicator in the present invention (see FIGS. 10 and 12, both of which show no correlation between the value σ and the Carr's flowability index). It was found that, with use of the correlation equation (K-index) of the present invention, a value that has a higher correlation with the value σ than the Carr's flowability index does can be derived and the σ value can be estimated.

Furthermore, in a preferred embodiment of the present invention, probe insertion work PIW described in the following section (2-6-5) can be used as an additional indicator in addition to the correlation equation (K-index). Specifically, in the present invention, a water-absorbing agent containing a water-absorbing resin (SAP) as a main component and satisfying K-index≥70 and/or probe insertion work PIW≤30000 gf×mm is preferred, and a water-absorbing agent containing a water-absorbing resin (SAP) as a main component and satisfying K-index≥70 and PIW≤30000 gf×mm is particularly preferred.

(2-6-5) Probe Insertion Work (PIW)

The probe insertion work (PIW) (measured by probe insertion test) of a water-absorbing agent containing a water-absorbing resin (SAP) as a main component, for use in the present invention, is measured in accordance with the following "(c) Probe insertion test" in the <Measurement method> section. A lower PIW (when a probe is inserted by 20 mm) indicates a lower coefficient of internal friction and lower frictional force of the water-absorbing agent as powder, and thus indicates higher lubrication of the particulate water-absorbing agent.

Figure 11:
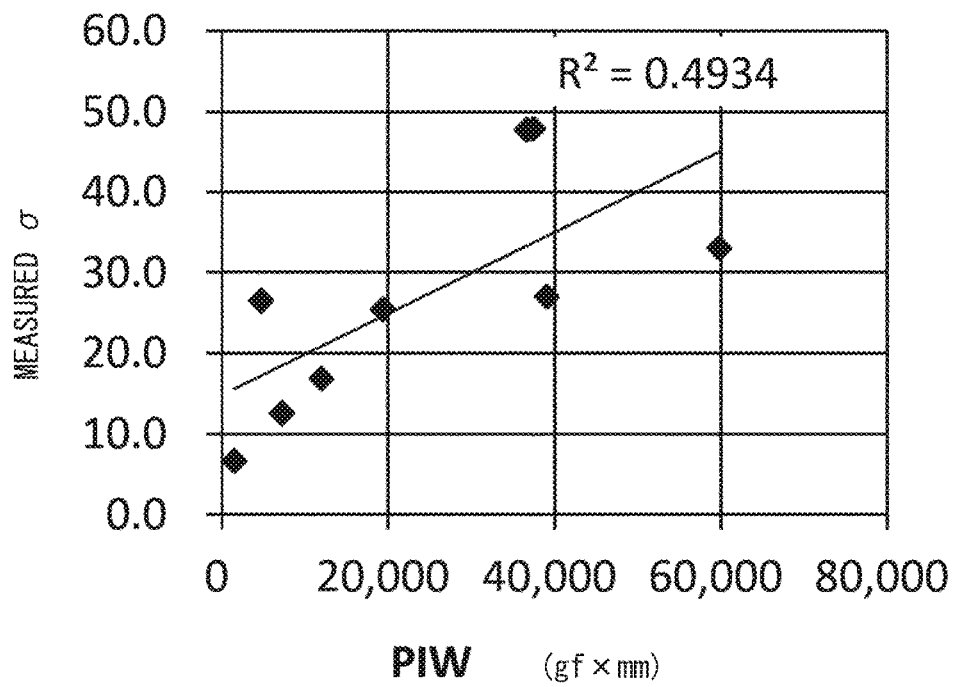
FIG. 11 is a chart showing the value σ plotted against probe insertion work (PIW), with regard to the water-absorbing agents of the present invention and the comparative water-absorbing agents.

The PIW and the standard deviation (σ) of the feed rate, when plotted, are correlated as shown in FIG. 11. The correlation is obtained especially in a case where PIW≤30000 gf×mm. In a case where PIW≤30000 gf×mm, the value σ is low and is 30.0 or less, as shown in FIG. 11. That is, in cases where PIW≤30000 gf×mm, the value of "σ", which is the standard deviation of the rate (feed rate) at which the water-absorbing agent is fed from the feeder, is small. Without wishing to be bound by any theory, cases where PIW≤30000 gf×mm are preferred because there is a tendency that fluctuation of the amount of the water-absorbing agent fed from the feeder per unit time is small and a bulk material can be supplied more stably. Cases where PIW≤20000 gf×mm are more preferred, because the tendency of stable supply becomes more noticeable.

In a preferred embodiment, preferred ranges (upper limits and lower limits) of the measured PIW are as follows.

Probe insertion work (PIW): Examples of preferred lower limit include 100 gf×mm, 1000 gf×mm, 4000 gf×mm, and examples of preferred upper limit include 30000 gf×mm, 20000 gf×mm, 15000 gf×mm, 13000 gf×mm, 10000 gf×mm, 8000 gf×mm.

Reference Literatures cited in the present specification, such as scientific literatures, patents, and patent applications, are incorporated herein by reference in their entirety to the same extent as if fully set forth herein at length.

In the descriptions provided so far, the present invention has been discussed based on preferred embodiments for easy understanding. The following description will discuss the present invention based on Examples. Note, however, that the descriptions provided so far and the following Examples are provided only for illustrative purposes, and are not intended to limit the present invention. Therefore, the scope of the present invention is limited neither by Embodiments nor by Examples specifically described in the present specification, and is limited only by Claims.

The present invention also provides the following items.

[1] A water-absorbing agent containing a water-absorbing resin as a main component, the water-absorbing agent satisfying the following (a) and (b):

(a) K-index is 70 or more; and (b) Moisture absorption blocking ratio, after 30 minutes of standing at a temperature of 25° C. and a relative humidity of 80% RH, is 70 weight % or less, the K-index being defined by the following equation:

$$K\text{-index}=100-(-438+3.6\times\text{angle of repose}+3.5\times\text{angle of difference}+7.9\times\text{compressibility rate}+290\times\text{bulk density (EDANA method)}).$$

[2] The water-absorbing agent according to [1], in which the moisture absorption blocking ratio is 40 weight % or less.

[3] The water-absorbing agent according to [1] or [2], in which the moisture absorption blocking ratio is 30 weight % or less.

[4] The water-absorbing agent according to any of [1] to [3], in which a powder flowability of the water-absorbing agent is 10.0 g/s or more.

[5] The water-absorbing agent according to any of [1] to [4], in which a powder flowability of the water-absorbing agent is 11.0 g/s or more.

[6] The water-absorbing agent according to any of [1] to [5], in which a surface tension of the water-absorbing agent is 65 mN/m or more.

[7] The water-absorbing agent according to any of [1] to [6], in which diffusing absorbency, which is measured 10 minutes after a start of absorption of 0.9 weight % aqueous sodium chloride solution by the water-absorbing agent under a load of 1.96 kPa, is 15 g/g or more.

[8] The water-absorbing agent according to any of [1] to [7], in which a probe insertion work of the water-absorbing agent is 30000 gf×mm or less.

[9] The water-absorbing agent according to any of [1] to [8], in which a moisture content of the water-absorbing agent is 10 weight % or less.

[10] The water-absorbing agent according to any of [1] to [9], further containing a polyvalent metal salt.

[11] The water-absorbing agent according to any of [1] to [10], further containing a surfactant.

[12] The water-absorbing agent according to any of [1] to [11], further containing a hydrophilic polymer compound.

[13] The water-absorbing agent according to any of [1] to [12], in which the water-absorbing agent is in the form of particles having a non-uniformly pulverized shape.

[14] An absorbent article containing a water-absorbing agent recited in any of [1] to [13].

[15] A method of continuously feeding, with use of a feeder, a water-absorbing agent containing a water-absorbing resin (SAP) as a main component, the feeder including a housing and a drive rotor, the housing having an inlet, an outlet, and an inner wall that extends from the inlet to the outlet, the drive rotor having (a) a hub rotatable about a rotation axis and (b) a plurality of drive disks having a periphery and extending from the hub toward the inner wall of the housing, the inner wall of the housing, the plurality of drive disks, and the hub defining a materials transfer duct through which material is transferred from the inlet of the housing to the outlet of the housing, the water-absorbing agent satisfying K-index≥70, the K-index being defined by the following equation:

$$K\text{-index}=100-(-438+3.6\times\text{angle of repose}+3.5\times\text{angle of difference}+7.9\times\text{compressibility rate}+290\times\text{bulk density (EDANA method)}).$$

[16] The method according to [15], in which the water-absorbing agent satisfies K-index 75.

[17] The method according to [15] or [16], in which the water-absorbing agent satisfies K-index≥80.

[18] The method according to any of [15] to [17], further including a step of, based on the K-index, selecting, as the water-absorbing agent for use in the feeder, a water-absorbing agent satisfying K-index≥70.

[19] The method according to any of [15] to [18], further including a step of, based on the K-index, selecting, from a plurality of water-absorbing agents, the water-absorbing agent that is for use in the feeder and that causes no or little fluctuation of feed amount per unit time.

[20] A method for producing an absorbent article with use of a water-absorbing agent containing a water-absorbing resin (SAP) as a main component, the method including: a step of continuously feeding the water-absorbing agent with use of the feeder by a method recited in any of [15] to [19]; and a step of producing an absorbent article with use of the water-absorbing agent thus fed.

[21] A method for producing an absorbent article with use of a water-absorbing agent containing a water-absorbing resin (SAP) as a main component, the method including: a step of continuously feeding the water-absorbing agent with use of a feeder; and a step of producing an absorbent article with use of the water-absorbing agent thus fed, the feeder including a housing and a drive rotor and being a feeder in which the housing has an inlet, an outlet, and an inner wall that extends from the inlet to the outlet, the drive rotor has (a) a hub rotatable about a rotation axis and (b) a plurality of drive disks having a periphery and extending from the hub toward the inner wall of the housing, and the inner wall of the housing, the plurality of drive disks, and the hub define a materials transfer duct through which material is transferred from the inlet of the housing to the outlet of the housing, the water-absorbing agent satisfying K-index≥70, the K-index being defined by the following equation:

$$K\text{-index}=100-(-438+3.6\times\text{angle of repose}+3.5\times\text{angle of difference}+7.9\times\text{compressibility rate}+290\times\text{bulk density (EDANA method)}).$$

[22] The method according to [21], in which the water-absorbing agent satisfies K-index≥75.

[23] The method according to [21] or [22], in which the water-absorbing agent satisfies K-index≥80.

[24] A method of preparing, in a feeder, a certain amount of a "feed" of a water-absorbing agent containing a water-absorbing resin (SAP) as a main component such that the feed rate of the "feed" falls within a certain deviation range, the method including a step of continuously feeding the water-absorbing agent with use of the feeder by a method recited in any of [15] to [23].

[25] A method of continuously feeding, with use of a feeder, a water-absorbing agent containing a water-absorbing resin (SAP) as a main component, the feeder including a housing and a drive rotor and being a feeder in which the housing has an inlet, an outlet, and an inner wall that extends from the inlet to the outlet, the drive rotor has (a) a hub rotatable about a rotation axis and (b) a plurality of drive disks having a periphery and extending from the hub toward the inner wall of the housing, and the inner wall of the housing, the plurality of drive disks, and the hub define a materials transfer duct through which material is transferred from the inlet of the housing to the outlet of the housing, the water-absorbing agent satisfying K-index≥70, the K-index being defined by the following equation:

$$K\text{-index}=100-(-438+3.6\times\text{angle of repose}+3.5\times\text{angle of difference}+7.9\times\text{compressibility rate}+290\times\text{bulk density (EDANA method)}),\text{ and}$$

the water-absorbing agent satisfying at least one of the following (i) and (ii): (i) the water-absorbing agent has a bulk density falling within the range of from 0.5 to 0.9, has a compressibility rate of 5 to 20, and has an angle of repose of 25° to 45° and/or an angle of difference of 2° to 20°; (ii) the water-absorbing agent contains a polyvalent metal salt of an organic acid or contains a multicomponent metal compound, the polyvalent metal salt containing seven or more carbon atoms, the multicomponent metal compound having a hydrotalcite structure and containing divalent and trivalent metal cations and a hydroxyl group.

[26] The method according to [25], in which the polyvalent metal salt of an organic acid, containing seven or more carbon atoms, is selected from the group consisting of calcium laurate, magnesium laurate, zinc laurate, aluminum laurate, calcium myristate, magnesium myristate, aluminum myristate, zinc myristate, calcium palmitate, magnesium palmitate, aluminum palmitate, zinc palmitate, calcium stearate, magnesium stearate, zinc stearate, and aluminum stearate.

[27] The method according to [25] or [26], in which the multicomponent metal compound is selected from the group consisting of $Mg_6Al_2(OH)_{16}CO_3 \cdot 4H_2O$ and $Mg_4Al_2(OH)_{12}CO_3 \cdot 3H_2O$.

[28] A method of continuously feeding, with use of a feeder, a water-absorbing agent containing a water-absorbing resin (SAP) as a main component, the method being arranged such that particles of the water-absorbing agent, introduced through an inlet of the feeder, gather and are thereby, due to a friction of the water-absorbing agent, brought into a "lock-up" condition, the water-absorbing agent is conveyed through a materials transfer duct to an outlet as disks rotate, the "lock-up" condition is cleared, and the water-absorbing agent is discharged through the outlet, the water-absorbing agent satisfying K-index≥70, the K-index being defined by the following equation:

$$K\text{-index}=100-(-438+3.6\times\text{angle of repose}+3.5\times\text{angle of difference}+7.9\times\text{compressibility rate}+290\times\text{bulk density (EDANA method)}).$$

[29] The method according to [28], in which the water-absorbing agent satisfies K-index≥75.

[30] The method according to [28] or [29], in which the water-absorbing agent satisfies K-index≥80.

[31] The method according to any of [28] to [30], further including a step of, based on the K-index, selecting, as the water-absorbing agent for use in the feeder, a water-absorbing agent satisfying K-index≥70.

[32] The method according to any of [28] to [31], further including a step of, based on the K-index, selecting, from a plurality of water-absorbing agents, the water-absorbing agent that is for use in the feeder and that causes no or little fluctuation of feed amount per unit time.

[33] A method of producing an absorbent article with use of a water-absorbing agent containing a water-absorbing resin (SAP) as a main component, the method including: a step of continuously feeding the water-absorbing agent with use of the feeder by a method recited in any of [28] to [32]; and a step of producing an absorbent article with use of the water-absorbing agent thus fed.

[34] A method of producing an absorbent article with use of a water-absorbing agent containing a water-absorbing resin (SAP) as a main component, the method including: a step of continuously feeding the water-absorbing agent with use of a feeder; and a step of producing an absorbent article with use of the water-absorbing agent thus fed, the feeder being arranged such that particles of the water-absorbing agent, introduced through an inlet of the feeder, gather and are thereby, due to a friction of the water-absorbing agent, brought into a "lock-up" condition, the water-absorbing agent is conveyed through a materials transfer duct to an outlet as disks rotate, the "lock-up" condition is cleared, and the water-absorbing agent is discharged through the outlet, the water-absorbing agent satisfying K-index≥70, the K-index being defined by the following equation:

K-index=100−(−438+3.6×angle of repose+3.5×angle of difference+7.9×compressibility rate+290× bulk density (EDANA method)).

[35] The method according to [34], in which the water-absorbing agent satisfies K-index 75.

[36] The method according to [34] or [35], in which the water-absorbing agent satisfies K-index≥80.

[37] A method of preparing, in a feeder, a certain amount of a "feed" of a water-absorbing agent containing a water-absorbing resin (SAP) as a main component such that the feed rate of the "feed" falls within a certain deviation range, the method including a step of continuously feeding the water-absorbing agent with use of the feeder by a method recited in any of [28] to [36].

[38] A method of continuously feeding, with use of a feeder, a water-absorbing agent containing a water-absorbing resin (SAP) as a main component, the method being arranged such that particles of the water-absorbing agent, introduced through an inlet of the feeder, gather and are thereby, due to a friction of the water-absorbing agent, brought into a "lock-up" condition, the water-absorbing agent is conveyed through a materials transfer duct to an outlet as disks rotate, the "lock-up" condition is cleared, and the water-absorbing agent is discharged through the outlet, the water-absorbing agent satisfying K-index≥70, the K-index being defined by the following equation:
K-index=100−(−438+3.6×angle of repose+3.5×angle of difference+7.9×compressibility rate+290×bulk density (EDANA method)), and the water-absorbing agent satisfying at least one of the following (i) and (ii): (i) the water-absorbing agent has a bulk density falling within the range of from 0.5 to 0.9, has a compressibility rate of 5 to 20, and has an angle of repose of 25° to 45° and/or an angle of difference of 2° to 20°; (ii) the water-absorbing agent contains a polyvalent metal salt of an organic acid or contains a multicomponent metal compound, the polyvalent metal salt containing seven or more carbon atoms, the multicomponent metal compound having a hydrotalcite structure and containing divalent and trivalent metal cations and a hydroxyl group.

[39] The method according to [38], in which the polyvalent metal salt of an organic acid, containing seven or more carbon atoms, is selected from the group consisting of calcium laurate, magnesium laurate, zinc laurate, aluminum laurate, calcium myristate, magnesium myristate, aluminum myristate, zinc myristate, calcium palmitate, magnesium palmitate, aluminum palmitate, zinc palmitate, calcium stearate, magnesium stearate, zinc stearate, and aluminum stearate.

[40] The method according to [38] or [39], in which the multicomponent metal compound is selected from the group consisting of $Mg_6Al_2(OH)_{16}CO_3 \cdot 4H_2O$ and $Mg_4Al_2(OH)_{12}CO_3 \cdot 3H_2O$.

[41] The method according to any of [15] to [40], in which: a fluctuation of the amount of the water-absorbing agent fed per unit time is defined by "(σ/average flow rate)×100" where σ represents the standard deviation of the amount of the water-absorbing agent fed per unit time; and a value of "(σ/average flow rate)×100" is 1.95 or less.

[42] The method according to any of [15] to [41], in which the feeder is a loss-in quantitative feeder.

[43] The method according to any of [15] to [42], in which the feeder includes a bulk solid pump (BSP: Bulk Solids Pump™).

[44] The method according to any of [15] to [43], in which the water-absorbing agent is fed at a temperature equal to or below a glass-transition temperature (Tg) of the water-absorbing agent.

[45] The method according to any of [15] to [44], in which the water-absorbing agent is fed at a temperature of 0° C. to 80° C.

[46] The method according to any of [15] to [45], in which the water-absorbing agent has a moisture content of 0.5 weight % to 15 weight %.

[47] The method according to any of [15] to [46], in which the water-absorbing agent satisfies "probe insertion work PIW≤30000 gf×mm", the probe insertion work PIW being a work done when an insertion member is inserted to a predetermined depth in the water-absorbing agent.

In the present invention, it is intended that one or more of the characteristics above can be provided not only in combination disclosed clearly above but also in further combinations. Further embodiments and advantages of the present invention will be recognized by a person skilled in the art through, as necessary, reading and understanding the detailed description below.

EXAMPLES

Examples Relating to Water-Absorbing Agent of Embodiment 1

The following shows Examples relating to a water-absorbing agent of the foregoing <Embodiment 1>.

The following description will discuss the present invention in greater detail on the basis of Examples and Comparative Examples below. Note, however, that the present invention is not limited to the description thereof and that the present invention also encompasses in its scope any Example derived from a combination of technical means disclosed in different Examples.

Electric devices/apparatuses (including devices/apparatuses used to measure physical properties of a water-absorbing agent) in Examples and Comparative Examples each used a 200-V or 100-V electric power supply, unless otherwise specified. Further, physical properties of a water-absorbing agent of the present invention were measured at room temperature (20° C. to 25° C.) and at a relative humidity of 50% RH, unless otherwise specified.

[1. Measurement of Physical Properties of Water-Absorbing Agent or Water-Absorbing Resin]

(a) Centrifuge Retention Capacity (CRC)

In the present specification, "centrifuge retention capacity (CRC) of a water-absorbing agent or water-absorbing resin in accordance with the present invention was measured in conformity with an EDANA method (ERT 441.2-02).

(b) Fluid Retention Capacity Under Pressure 0.3 Psi (AAP0.3/Absorbency Against Pressure 0.3)

In the present specification, "fluid retention capacity under pressure 0.3 psi (AAP0.3)" of a water-absorbing agent or water-absorbing resin in accordance with the present invention was measured in conformity with an EDANA method (ERT 442.2-02). Note that measurement was carried out under a load of 2.03 kPa (0.3 psi).

(c) Fluid Retention Capacity Under Pressure 0.7 Psi (AAP0.7/Absorbency Against Pressure 0.7)

In the present specification, "fluid retention capacity under pressure 0.7 psi (AAP0.7)" of a water-absorbing agent or water-absorbing resin in accordance with the present invention was measured in the same manner as described in the above section "(b) Fluid retention capacity under pressure 0.3 psi (AAP0.3/Absorbency Against Pressure 0.3)", except that a load applied to a water-absorbing agent or a water-absorbing resin composition was changed to 4.83 kPa (0.7 psi).

(d) Moisture Absorption Blocking Ratio (B.R./Blocking Ratio)

2 g of a water-absorbing agent or a water-absorbing resin was dispersed uniformly in an aluminum cup having a diameter of 52 mm. The aluminum cup was then allowed to stand for 30 minutes in a thermo-hygrostat (ESPEC CORP.; MODEL: SH-641) set to a temperature of 25° C. and a relative humidity of 80±5% RH. Thereafter, the water-absorbing agent or the water-absorbing resin in the aluminum cup was gently transferred onto a JIS standard sieve (The IIDA TESTING SIEVE/inner diameter: 80 mm) having a mesh size of 2000 µm (JIS 8.6 mesh). A low-tap type sieve shaker (product name:"ES-65 sieve shaker", manufactured by Sieve Factory Iida Co., Ltd., rotation speed: 230 rpm, number of impacts: 130 rpm) was used to carry out classification for 5 seconds at room temperature (20° C. to 25° C.) and a relative humidity of 50% RH. A weight (W1 [g]) of the water-absorbing agent or water-absorbing resin remaining on the JIS standard sieve, and a weight (W2 [g]) of the water-absorbing agent or water-absorbing resin which had passed through the JIS standard sieve were measured, and moisture absorption blocking ratio was calculated using the equation below.

Moisture absorption blocking ratio (B.R.) [weight %]=$\{W1/(W1+W2)\} \times 100$ Note that a lower value of the moisture absorption blocking ratio means better moisture absorption flowability.

(e) Powder Flowability (F.R./Flow-Rate)

In the present specification, "powder flowability (F.R.)" of a water-absorbing agent or a water-absorbing resin in accordance with the present invention was measured in conformity with an EDANA method (ERT450.2-02).

(f) Surface Tension

Into a 100 ml beaker which had been sufficiently washed, 50 ml of physiological saline, which had been adjusted to 20° C., was put. First, the surface tension of the physiological saline was measured with use of a surface tension meter (manufactured by KRUSS, K11 automatic surface tension meter). In this measurement, the surface tension was within the range of 71 [mN/m] to 75 [mN/m]. Next, a fluorine resin rotor, which had been sufficiently washed and had a length of 25 mm, and 0.5 g of a water-absorbing agent were put in the beaker containing the physiological saline whose temperature had been adjusted to 20° C. and whose surface tension had been measured, and stirred at 500 rpm for 3 minutes. Then, the stirring was stopped and, after sedimentation of the water-absorbing agent which had absorbed water, the surface tension of a supernatant liquid was measured in the same manner as described above. Note that, in the present invention, a plate method using a platinum plate was employed, and the plate was sufficiently washed with deionized water and also cleaned with heat by the use of a gas burner before being used in each of the above measurements.

(g) Diffusing Absorbency (DAP/Diffusing Absorbency Under Pressure)

In accordance with a process described in and with use of a measurement apparatus disclosed in Japanese Patent Application Publication, Tokuhaihei, No. 8-57311, a weight W3 (g) of physiological saline (0.9 weight % aqueous sodium chloride solution) absorbed by a water-absorbing agent under a pressure of 1.96 kPa during a period of 10 minutes was measured. Then, diffusing absorbency (g/g) after 10 minutes from the start of the absorption was calculated from the weight W3, using the following equation:

Diffusing absorbency (g/g)=weight W3 (g)/weight (g) of water-absorbing agent.

(h) Moisture Content

In the present specification, "moisture content" of a water-absorbing agent or water-absorbing resin in accordance with the present invention means the proportion of a component, which volatilizes at 180° C., to the amount of powder of the water-absorbing agent or water-absorbing resin.

1.00 g of a water-absorbing agent or water-absorbing resin was spread uniformly in an aluminum cup (height: 2 cm, diameter of bottom surface: 4 cm) on the bottom surface thereof, and a combined weight W4 (g) of the aluminum cup and the water-absorbing agent or water-absorbing resin therein was measured. The aluminum cup containing the water-absorbing agent or water-absorbing resin therein was allowed to stand for 3 hours in a dryer (EYELA, manufactured by Tokyo Rikakikai Co., Ltd., fixed temperature incubator/dryer (natural oven) NDO-450) which had been set to 180° C. The aluminum cup containing the water-absorbing resin was removed from the hot air dryer, and the combined weight W5 (g) of the aluminum cup and the water-absorbing resin therein was measured immediately after removal (at least within 1 minute of removal). The values of W4 and W5 were used in the following equation to calculate moisture content (weight %).

Moisture content(weight %)=$[(W4(g)-W5(g))/$ (weight (g) of water-absorbing agent or water-absorbing resin)]$\times 100$ The relationship between the moisture content and solid content is as follows: {solid content=100−moisture content}.

Production Example 1-1

The following aqueous monomer solution was prepared: an aqueous monomer solution containing 300 parts by weight of acrylic acid, 100 parts by weight of a 48 weight % aqueous sodium hydroxide solution, 0.766 parts by weight of polyethylene glycol diacrylate (average n number: 9), 18.6 parts by weight of a 0.1 weight % aqueous trisodium diethylenetriamine pentaacetate solution, and 295 parts by weight of deionized water.

Next, the aqueous monomer solution whose temperature had been adjusted to 38° C. was continuously supplied by a metering pump, and then 157.4 parts by weight of a 48 weight % aqueous sodium hydroxide solution was further continuously line-mixed with the aqueous monomer solution. At this stage, the temperature of the aqueous monomer solution rose to 80° C. due to heat of neutralization.

Further, 14.8 parts by weight of a 4 weight % aqueous sodium persulfate solution was continuously line-mixed with the aqueous monomer solution, and then the resultant mixture was continuously supplied into a continuous polymerization device, having a planar polymerization belt with dams at both sides, so that the supplied mixture had a thickness of 10 mm. Thereafter, polymerization (polymerization time: 3 minutes) was continuously carried out, so that a belt-shaped hydrogel polymer was obtained. The belt-shaped hydrogel polymer obtained was continuously cut at regular intervals in the width direction relative to the traveling direction of the polymerization belt so that the cut length was 300 mm. Thus, a hydrogel polymer was obtained. The obtained hydrogel polymer was supplied to a screw extruder and subjected to gel-crushing, and thereby a hydrogel polymer in the form of particles was obtained.

Next, within one minute of the end of the gel-crushing, the hydrogel polymer in the form of particles was placed on a through-flow belt (the hydrogel polymer in the form of particles has a temperature of 80° C. at this stage). Then, the hydrogel polymer in the form of particles was dried by causing hot air having 185° C. to flow therethrough for 30 minutes, so that a dried polymer was obtained. The hot air had an average air velocity of 1.0 m/s in the direction perpendicular to the traveling direction of the through-flow belt. The air velocity of the hot air was measured with use of a constant temperature thermal anemometer (Anemomaster 6162 manufactured by Kanomax Japan Inc.).

Next, the dried polymer obtained through the above drying step, in its entirety, was supplied to a three-stage roll mill and pulverized (subjected to a pulverizing step). Thereafter, the dried polymer thus pulverized was further classified with use of JIS standard sieves having respective mesh sizes of 710 μm and 175 μm. Thus, water-absorbing resin powder (1-a) (which is a water-absorbing resin having a solid content of 93 weight %) was obtained. The water-absorbing resin powder (1-a) had a CRC of 45.4 g/g.

Production Example 1-2

421.3 g of acrylic acid, 1.040 g (0.034 mol % relative to carboxyl-group-containing unsaturated monomers) of polyethylene glycol diacrylate (molecular weight: 523) as an internal crosslinking agent, 2.58 g of a 1.0 weight % aqueous trisodium diethylenetriamine pentaacetate (DTPA•3Na) solution, 173.57 g of a 48.5 weight % aqueous sodium hydroxide solution, and 396.31 g of deionized water (ion-exchange water) were introduced into a 2-liter polypropylene container, and were mixed with one another to prepare an aqueous monomer solution.

Next, the aqueous monomer solution was cooled while being stirred. At a time point at which the liquid temperature reached 39.8° C., 181.77 g of a 48.5 weight % aqueous sodium hydroxide solution having a temperature adjusted to 40° C. was added to the aqueous monomer solution, and was mixed therewith. At this time, the temperature of the aqueous monomer solution rose to 80.1° C. due to heat of neutralization at a second stage.

Next, 16.89 g of a 4.5 weight % aqueous sodium persulfate solution was added to the aqueous monomer solution while stirring was carried out. Immediately after that, the resulting solution was poured in an atmospheric air open system into a stainless steel vat-type vessel (with a bottom surface of 340 mm×340 mm and a height of 25 mm; inner surface: Teflon (registered trademark) coating). Pouring of the aqueous monomer solution into the vat-type vessel commenced 55 seconds after the start of the second-stage neutralization. The vat-type vessel was heated with use of a hot plate (NEO HOTPLATE HI-1000; Iuchi Seiei Do Ltd.) until surface temperature reached 40° C.

56 seconds after the aqueous monomer solution was poured into the vat-type vessel, a polymerization reaction started. In this polymerization reaction, a polymer that was generated gave off water vapor and swelled and foamed in various directions. The polymer then shrunk to a size slightly larger than the size of the vat-type vessel. 3 minutes after the start of the polymerization reaction, a hydrogel polymer was taken out. Note that this series of operations was carried out in an atmospheric air open system.

The hydrogel polymer obtained through the above polymerization reaction was subjected to gel-crushing with use of a meat chopper (HL-3225N; plate pore diameter: 10.0 mm; Remacom Co., Ltd.), so as to obtain a hydrogel polymer in the form of particles.

The hydrogel polymer was introduced into the meat chopper at a rate of 230 g/min. The gel-crushing was carried out while deionized water having a temperature adjusted to 90° C. was being added at a rate of 50 g/min simultaneously with the introduction of the hydrogel polymer.

The hydrogel polymer in the form of particles obtained through the above operation was spread on a stainless-steel metal gauze having a mesh size of 850 μm, and was dried by letting through 180° C. hot air for 30 minutes. In this way, a dried polymer was obtained.

The dried polymer was pulverized with use of a roll mill (WML-type roll pulverizer; Inoguchi Giken Ltd.), and was then classified with use of JIS standard sieves having respective mesh sizes of 710 μm and 90 μm. This produced water-absorbing resin powder (1-b) (which is a water-absorbing resin having a solid content of 95 weight %) having a non-uniformly pulverized shape. The water-absorbing resin powder (1-b) had a CRC of 44.3 g/g.

Production Example 1-3

431.2 g of acrylic acid, 1.158 g (0.034 mol % relative to carboxyl-group-containing unsaturated monomers) of polyethylene glycol diacrylate (molecular weight: 523) as an internal crosslinking agent, 2.64 g of a 1.0 weight % aqueous trisodium diethylenetriamine pentaacetate (DTPA•3Na) solution, 177.65 g of a 48.5 weight % aqueous sodium hydroxide solution, and 384.56 g of deionized water (ion-exchange water) were introduced into a 2-liter polypropylene container, and were mixed with one another to prepare an aqueous monomer solution.

Next, the aqueous monomer solution was cooled while being stirred. At a time point at which the liquid temperature reached 39.5° C., 185.55 g of a 48.5 weight % aqueous sodium hydroxide solution having a temperature adjusted to 40° C. was added to the aqueous monomer solution, and was mixed therewith. At this time, the temperature of the aqueous monomer solution rose to 79.8° C. due to heat of neutralization at a second stage.

Next, 17.29 g of a 4.5 weight % aqueous sodium persulfate solution was added to the aqueous monomer solution while stirring was carried out. Immediately after that, the resulting solution was poured in an atmospheric air open system into a stainless steel vat-type vessel (with a bottom surface of 340 mm×340 mm and a height of 25 mm; inner surface: Teflon (registered trademark) coating). Pouring of the aqueous monomer solution into the vat-type vessel commenced 55 seconds after the start of the second-stage neutralization. The vat-type vessel was heated with use of a hot plate (NEO HOTPLATE HI-1000; Iuchi Seiei Do Ltd.) until surface temperature reached 40° C.

58 seconds after the aqueous monomer solution was poured into the vat-type vessel, a polymerization reaction started. In this polymerization reaction, a polymer that was generated gave off water vapor and swelled and foamed in various directions. The polymer then shrunk to a size slightly larger than the size of the vat-type vessel. 3 minutes after the start of the polymerization reaction, a hydrogel polymer was taken out. Note that this series of operations was carried out in an atmospheric air open system.

The hydrogel polymer obtained through the above polymerization reaction was subjected to gel-crushing with use of a meat chopper (HL-3225N; plate pore diameter: 10.0 mm; Remacom Co., Ltd.) to obtain a hydrogel polymer in the form of particles.

The hydrogel polymer was introduced into the meat chopper at a rate of 230 g/min. The gel-crushing was carried out while deionized water having a temperature adjusted to 90° C. was being added at a rate of 50 g/min simultaneously with the introduction of the hydrogel polymer.

The hydrogel polymer in the form of particles obtained through the above operation was spread on a stainless-steel metal gauze having a mesh size of 850 μm, and was dried by letting through 180° C. hot air for 30 minutes. In this way, a dried polymer was obtained.

The dried polymer was pulverized with use of a roll mill (WML-type roll pulverizer; Inoguchi Giken Ltd.), and was then classified with use of JIS standard sieves having respective mesh sizes of 850 μm and 90 μm. This produced water-absorbing resin powder (1-c) (which is a water-absorbing resin having a solid content of 96 weight %) having a non-uniformly pulverized shape. The water-absorbing resin powder (1-c) had a CRC of 42.1 g/g.

Production Example 1-4

Into a reactor formed by attaching a lid to a stainless steel twin-arm kneader (capacity: 10 L) having two sigma-type blades and a jacket, 374.3 g of acrylic acid, 3961.3 g of a 37 weight % aqueous sodium hydroxide solution, 637.3 g of deionized water, and 4.25 g of polyethylene glycol diacrylate (molecular weight: 523) (0.042 mol % relative to carboxyl-group-containing unsaturated monomers) were dissolved to obtain an aqueous monomer solution.

Next, the aqueous monomer solution was degassed in a nitrogen atmosphere for 20 minutes. Next, while the aqueous monomer solution was stirred, 12.47 g of a 10 weight % aqueous sodium persulfate solution and 10.39 g of a 0.1 weight % aqueous L-ascorbic acid solution were added thereto. Polymerization commenced approximately 1 minute thereafter.

Polymerization was carried out at 20° C. to 95° C. while crushing a gel that was generated. 30 minutes after polymerization started, a hydrogel polymer was taken out. The hydrogel polymer obtained thusly had been grain refined such that its particles were not more than approximately 5 mm in size.

The grain-refined hydrogel polymer in the form of particles was spread out on a metal gauze (50 mesh) and dried with hot air at 180° C. for 50 minutes to obtain a dried polymer. The obtained dried polymer was pulverized with use of a roll mill and further classified with use of a JIS standard sieve having a mesh size of 710 μm and a JIS standard sieve having a mesh size of 150 μm. This produced water-absorbing resin powder (1-d) (which is a water-absorbing resin having a solid content of 95 weight %) having a non-uniformly pulverized shape. The water-absorbing resin powder (1-d) had a CRC of 40.5 g/g.

Example 1-1

The water-absorbing resin powder (1-a) obtained in Production Example 1-1 was transferred to a rotary mixer manufactured by Gebrueder Loedige Maschinenbau Gmbh, and an aqueous surface-crosslinking agent solution containing 0.27 parts by weight of ethylene carbonate, 0.45 parts by weight of propylene glycol, 1.8 parts by weight of deionized water, and 0.02 parts by weight of 10 weight % aqueous polyoxyethylene (20) sorbitan monostearate solution (product name: RHEODOL (registered trademark) TW-S120V; manufactured by Kao Corporation) was mixed with 100 parts by weight of the water-absorbing resin powder (1-a) uniformly. Then, the resultant mixture was subjected to a heating treatment in a paddle mixer preheated to 200° C. An average time (retention time) that the mixture was retained in the paddle mixer was approximately 40 minutes. The heated material was cooled and subjected to classification with use of JIS standard sieves having respective mesh sizes of 850 μm and 150 μm, so that surface-crosslinked water-absorbing resin particles were obtained.

Next, the following mixed solution was prepared: a mixed solution (i) which contains 0.38 parts by weight of 27 weight % aqueous aluminum sulfate solution (8 weight % based on aluminum oxide) as a polyvalent metal cation, 0.11 parts by weight of 60 weight % aqueous sodium lactate solution, and 0.01 parts by weight of propylene glycol. 100 parts by weight of the surface-crosslinked water-absorbing resin particles were preheated to 60° C. and, to these surface-crosslinked water-absorbing resin particles, 0.02 parts by weight of 10 weight % aqueous polyoxyethylene (20) sorbitan monostearate solution (product name: RHEODOL (registered trademark) TW-S120V; manufactured by Kao Corporation), 0.03 parts by weight of polyethylene glycol (average molecular weight: 400) and 1.0 part by weight of deionized water were mixed uniformly. Then, to the resultant mixture, 0.5 parts by weight of the mixed solution (i) and 0.022 parts by weight of trisodium diethylenetriamine pentaacetate (called "DTPA•3Na" for short, CHELEST PC-45, manufactured by CHELEST CORPORATION) were added and mixed uniformly. After that, the resultant mixture was subjected to a heating treatment under a windless condition at 60° C. for 40 minutes, and then passed through a JIS standard sieve having a mesh size of 850 μm to obtain a water-absorbing agent (1-1).

The water-absorbing agent (1-1) had a surface tension of 69.3 mN/m, a diffusing absorbency (DAP 10 min) of 21.0 g/g, and a moisture content of 3.0 weight %.

Example 1-2

The same operations as described in Example 1-1 were carried out, except that the amount of polyethylene glycol added after the heating treatment was changed to 0.01 parts by weight and that the amount of the mixed solution (i) added was changed to 0.1 parts by weight. In this way, a water-absorbing agent (1-2) was obtained.

The water-absorbing agent (1-2) had a surface tension of 68.2 mN/m, a diffusing absorbency (DAP 10 min) of 22.3 g/g, and a moisture content of 3.4 weight %.

Example 1-3

The same operations as described in Example 1-1 were carried out, except that the amount of polyethylene glycol added after the heating treatment was changed to 0.01 parts by weight and that the amount of the mixed solution (i) added was changed to 0.3 parts by weight. In this way, a water-absorbing agent (1-3) was obtained.

Example 1-4

The water-absorbing resin powder (1-a) obtained in Production Example 1-1 was transferred to a rotary mixer manufactured by Gebrueder Loedige Maschinenbau Gmbh, and an aqueous surface-crosslinking agent solution containing 0.27 parts by weight of ethylene carbonate, 0.45 parts by weight of propylene glycol, and 1.8 parts by weight of deionized water was mixed with 100 parts by weight of the water-absorbing resin powder (1-a) uniformly. Then, the resultant mixture was subjected to a heating treatment in a paddle mixer preheated to 200° C. An average time (retention time) that the mixture was retained in the paddle mixer was approximately 40 minutes. The heated material was cooled and subjected to classification with use of JIS standard sieves having respective mesh sizes of 850 μm and 150 μm, so that surface-crosslinked water-absorbing resin particles were obtained.

Next, 100 parts by weight of the surface-crosslinked water-absorbing resin particles were preheated to 60° C. and, to these surface-crosslinked water-absorbing resin particles, 0.02 parts by weight of 10 weight % aqueous polyoxyethylene (20) sorbitan monostearate solution (product name: RHEODOL (registered trademark) TW-S 120V; manufactured by Kao Corporation), 0.03 parts by weight of polyethylene glycol (average molecular weight: 400) and 1.0 part by weight of deionized water were mixed uniformly. Then, to the resultant mixture, 0.5 parts by weight of the mixed solution (i) described in Example 1-1 and 0.022 parts by weight of trisodium diethylenetriamine pentaacetate (called "DTPA•3Na" for short, CHELEST PC-45, manufactured by CHELEST CORPORATION) were added and mixed uniformly. After that, the resultant mixture was subjected to a heating treatment under a windless condition at 60° C. for 40 minutes, and then passed through a JIS standard sieve having a mesh size of 850 μm to obtain a water-absorbing agent (1-4).

Example 1-5

The same operations as described in Example 1-4 were carried out, except that the amount of polyethylene glycol added after the heating treatment was changed to 0.04 parts by weight and that the amount of the mixed solution (i) added was changed to 0.7 parts by weight. In this way, a water-absorbing agent (1-5) was obtained.

The water-absorbing agent (1-5) had a surface tension of 70.5 mN/m, a diffusing absorbency (DAP 10 min) of 19.9 g/g, and a moisture content of 2.9 weight %.

Example 1-6

The same operations as described in Example 1-4 were carried out, except that the amount of polyethylene glycol added after the heating treatment was changed to 0.02 parts by weight and that the amount of the mixed solution (i) added was changed to 0.2 parts by weight. In this way, a water-absorbing agent (1-6) was obtained.

The water-absorbing agent (1-6) had a surface tension of 71.0 mN/m, a diffusing absorbency (DAP 10 min) of 19.1 g/g, and a moisture content of 3.4 weight %.

Example 1-7

The same operations as described in Example 1-4 were carried out, except that the amount of polyethylene glycol added after the heating treatment was changed to 0.02 parts by weight and that the amount of the mixed solution (i) added was changed to 0.4 parts by weight. In this way, a water-absorbing agent (1-7) was obtained.

Example 1-8

The same operations as described in Example 1-4 were carried out, except that the amount of polyethylene glycol added after the heating treatment was changed to 0.03 parts by weight and that the amount of the mixed solution (i) added was changed to 0.4 parts by weight. In this way, a water-absorbing agent (1-8) was obtained.

Example 1-9

To 100 parts by weight of the water-absorbing resin powder (1-b) obtained in Production Example 1-2, a surface-crosslinking agent solution containing 0.022 parts by weight of ethylene glycol diglycidyl ether, 0.31 parts by weight of ethylene carbonate, 0.52 parts by weight of propylene glycol, and 2.1 parts by weight of deionized water was mixed uniformly. Then, the resultant mixture was subjected to a heating treatment in a paddle mixer preheated to 200° C. An average time (retention time) that the mixture was retained in the paddle mixer was approximately 30 minutes. The heated material was cooled and subjected to classification with use of JIS standard sieves having respective mesh sizes of 850 μm and 150 μm, so that surface-crosslinked water-absorbing resin particles were obtained.

Next, 100 parts by weight of the surface-crosslinked water-absorbing resin particles were preheated to 60° C. and, to these surface-crosslinked water-absorbing resin particles, 0.02 parts by weight of 10 weight % aqueous polyoxyethylene (20) sorbitan monostearate solution (product name: RHEODOL (registered trademark) TW-S 120V; manufactured by Kao Corporation), 0.03 parts by weight of polyethylene glycol (average molecular weight: 400), and 1.0 part by weight of deionized water were mixed uniformly. To the resultant mixture, the mixed solution (i) described in Example 1-1 and 0.022 parts by weight of trisodium diethylenetriamine pentaacetate (called "DTPA•3Na" for short, CHELEST PC-45, manufactured by CHELEST CORPO- RATION) were added and mixed uniformly. After that, the resultant mixture was subjected to a heating treatment under a windless condition at 60° C. for 40 minutes, and then passed through a JIS standard sieve having a mesh size of 850 μm to obtain a water-absorbing agent (1-9).

The water-absorbing agent (1-9) had a surface tension of 69.9 mN/m, a diffusing absorbency (DAP 10 min) of 19.2 g/g, and a moisture content of 3.8 weight %.

Example 1-10

The same operations as described in Example 1-9 were carried out, except that, after the heating treatment, 0.02 parts by weight of 10 weight % aqueous polyoxyethylene (20) sorbitan monostearate solution (product name: RHEODOL (registered trademark) TW-S 120V; manufactured by Kao Corporation) and 1.0 part by weight of deionized water were added and then the mixed solution (i) described in Example 1-1 and 0.022 parts by weight of trisodium diethylenetriamine pentaacetate (called "DTPA·3Na" for short, CHELEST PC-45, manufactured by CHELEST CORPORATION) were added. In this way, a water-absorbing agent (1-10) was obtained.

The water-absorbing agent (1-10) had a surface tension of 70.5 mN/m, a diffusing absorbency (DAP 10 min) of 19.5 g/g, and a moisture content of 2.8 weight %.

Example 1-11

The same operations as described in Example 1-1 were carried out, except that the water-absorbing resin powder (1-c) obtained in Production Example 1-3 was used instead of the water-absorbing resin powder (1-a). In this way, a water-absorbing agent (1-11) was obtained.

Example 1-12

The same operations as described in Example 1-5 were carried out, except that the water-absorbing resin powder (1-c) obtained in Production Example 1-3 was used instead of the water-absorbing resin powder (1-a). In this way, a water-absorbing agent (1-12) was obtained.

Example 1-13

The following mixed solution was prepared: a mixed solution (ii) which contains 3.0 parts by weight of a 5 weight % aqueous potassium alum solution (prepared by dissolving potassium alum dodecahydrate in deionized water), 0.11 parts by weight of a 60 weight % aqueous sodium lactate solution, and 0.01 parts by weight of propylene glycol. The same operations as described in Example 1-1 were carried out, except that 3.1 parts by weight of the mixed solution (ii) was added instead of 0.5 parts by weight of the mixed solution (i). In this way, a water-absorbing agent (1-13) was obtained.

Example 1-14

The following mixed solution was prepared: a mixed solution (iii) which contains 0.38 parts by weight of a 20 weight % aqueous aluminum chloride solution (prepared by dissolving aluminum chloride hexahydrate in deionized water), 0.11 parts by weight of a 60 weight % aqueous sodium lactate solution, and 0.01 parts by weight of propylene glycol. The same operations as described in Example 1-4 were carried out, except that 0.5 parts by weight of the mixed solution (iii) was added instead of the mixed solution (i). In this way, a water-absorbing agent (1-14) was obtained.

Example 1-15

The same operations as described in Example 1-1 were carried out, except that 0.045 parts by weight of polyethylene glycol (average molecular weight: 600) was added instead of 0.03 parts by weight of polyethylene glycol (average molecular weight: 400). In this way, a water-absorbing agent (1-15) was obtained.

Example 1-16

The same operations as described in Example 1-12 were carried out, except that 0.1 parts by weight of polypropylene glycol (average molecular weight: 1000) was added instead of 0.04 parts by weight of polyethylene glycol (average molecular weight: 400). In this way, a water-absorbing agent (1-16) was obtained.

Example 1-17

The same operations as described in Example 1-9 were carried out, except that 0.03 parts by weight of methoxy polyethylene glycol (average molecular weight: 400) was added instead of 0.03 parts by weight of polyethylene glycol (average molecular weight: 400). In this way, a water-absorbing agent (1-17) was obtained.

Example 1-18

The same operations as described in Example 1-3 were carried out, except that 0.008 parts by weight of sodium polyoxyethylene lauryl ether sulfate (product name: EMAL (registered trademark) 20C manufactured by Kao Corporation, solid content: 25 weight %) was added instead of 0.02 parts by weight of 10 weight % aqueous polyoxyethylene (20) sorbitan monostearate solution (product name: RHEODOL (registered trademark) TW-S120V; manufactured by Kao Corporation). In this way, a water-absorbing agent (1-18) was obtained.

Example 1-19

The same operations as described in Example 1-4 were carried out, except that 0.02 parts by weight of a 10 weight % aqueous solution of sorbitan monostearate (SPAN (registered trademark) 60) was added instead of 0.02 parts by weight of 10 weight % aqueous polyoxyethylene (20) sorbitan monostearate solution (product name: RHEODOL (registered trademark) TW-5120V; manufactured by Kao Corporation). In this way, a water-absorbing agent (1-19) was obtained.

Example 1-20

The water-absorbing resin powder (1-a) obtained in Production Example 1-1 was transferred to a rotary mixer manufactured by Gebrueder Loedige Maschinenbau Gmbh, and 0.28 parts by weight of 1,4-butanediol, 0.47 parts by weight of propylene glycol, and 2.5 parts by weight of deionized water were added to 100 parts by weight of the water-absorbing resin powder (1-a) and mixed uniformly. The obtained mixture was subjected to a heating treatment in a paddle mixer preheated to 200° C. Except the above procedure, the same operations as described in Example 1-1 were carried out. In this way, a water-absorbing agent (1-20) was obtained.

Example 1-21

The water-absorbing resin powder (1-c) obtained in Production Example 1-3 was transferred to a rotary mixer manufactured by Gebrueder Loedige Maschinenbau Gmbh, and 0.28 parts by weight of 1,4-butanediol, 0.47 parts by weight of propylene glycol, and 2.5 parts by weight of deionized water were added to 100 parts by weight of the water-absorbing resin powder (1-c) and mixed uniformly. The obtained mixture was subjected to a heating treatment in a paddle mixer preheated to 200° C. Except the above procedure, the same operations as described in Example 1-11 were carried out. In this way, a water-absorbing agent (1-21) was obtained.

Comparative Example 1-1

To 100 parts by weight of the water-absorbing resin particles surface-treated in Example 1-4, 0.7 parts by weight of the mixed solution (i) described in Example 1-1 and 0.022 parts by weight of trisodium diethylenetriamine pentaacetate (called "DTPA•3Na" for short, CHELEST PC-45, manufactured by CHELEST CORPORATION) were added and mixed uniformly. After that, the resultant mixture was subjected to a heating treatment under a windless condition at 60° C. for 40 minutes, and then passed through a JIS standard sieve having a mesh size of 850 μm to obtain a comparative water-absorbing agent (1-1).

The comparative water-absorbing agent (1-1) had a surface tension of 73.3 mN/m and a diffusing absorbency (DAP 10 min) of 9.7 g/g. Note that the moisture content of the comparative water-absorbing agent (1-1) was 3.1 weight %.

Comparative Example 1-2

The same operations as described in Comparative Example 1-1 were carried out, except that 0.04 parts by weight of polyethylene glycol as an additive and 1.0 part by weight of deionized water were mixed uniformly and then 0.7 parts by weight of the mixed solution (i) described in Example 1-1 and 0.022 parts by weight of trisodium diethylenetriamine pentaacetate (called "DTPA•3Na" for short, CHELEST PC-45, manufactured by CHELEST CORPORATION) were added and mixed uniformly. In this way, a comparative water-absorbing agent (1-2) was obtained.

The comparative water-absorbing agent (1-2) had a surface tension of 73.4 mN/m and a diffusing absorbency (DAP 10 min) of 3.6 g/g.

Comparative Example 1-3

The same operations as described in Example 1-4 were carried out, except that the water-absorbing resin powder (1-d) were used instead of the water-absorbing resin powder (1-a) and that the additives added after the surface-crosslinking step were changed to 0.02 parts by weight of 10 weight % aqueous polyoxyethylene (20) sorbitan monostearate solution (product name: RHEODOL (registered trademark) TW-S120V; manufactured by Kao Corporation) and 1.0 part by weight of deionized water. In this way, a comparative water-absorbing agent (1-3) was obtained.

The comparative water-absorbing agent (1-3) had a surface tension of 70.2 mN/m.

Comparative Example 1-4

The same operations as described in Comparative Example 1-3 were carried out, except that the amount of the weight % aqueous polyoxyethylene (20) sorbitan monostearate solution (product name: RHEODOL (registered trademark) TW-S120V; manufactured by Kao Corporation) added was changed to 0.06 parts by weight. In this way, a comparative water-absorbing agent (1-4) was obtained.

The comparative water-absorbing agent (1-4) had a surface tension of 59.6 mN/m and a diffusing absorbency (DAP 10 min) of 5.2 g/g.

Comparative Example 1-5

The same operations as described in Comparative Example 1-1 were carried out, except that 1.0 part by weight of a 27 weight % aqueous aluminum sulfate solution as an additive was mixed uniformly and then 0.02 parts by weight of a 10 weight % aqueous polyoxyethylene (20) sorbitan monostearate solution (product name: RHEODOL (registered trademark) TW-S120V; manufactured by Kao Corporation) and 1.0 part by weight of deionized water were added uniformly. In this way, a comparative water-absorbing agent (1-5) was obtained.

Comparative Example 1-6

To the surface-crosslinked water-absorbing resin particles obtained in Example 1-9, 0.30 parts by weight of hydrophilic silicon dioxide (product name: Aerosil 200 (manufactured by Nippon Aerosil Co., Ltd.) was mixed. The mixing was carried out in the following manner: 30 g of the water-absorbing resin was put in a 225-milliliter mayonnaise bottle together with the hydrophilic silicon dioxide and then mixed by shaking (at room temperature for 1 minute) with use of a paint shaker (manufactured by Toyo Seiki Seisaku-sho, Ltd.). In this way, a comparative water-absorbing agent (1-6) was obtained.

Comparative Example 1-7

3090.26 g of deionized water was placed in a thermally-insulated flat-bottom reaction vessel, 800 g of acrylic acid was added to the deionized water to obtain a first aqueous monomer solution, and the first aqueous monomer solution was cooled to 25° C. Next, a second aqueous monomer solution containing 1600 g of acrylic acid, 4.8 g of triallylamine, 120.53 g of 50 weight % methoxy polyethylene glycol (750) monomethacrylate, and 3.6 g of 9 mol ethoxylated trimethylolpropane triacrylate was added to the first aqueous monomer solution, cooled to 15° C., 24.0 g of 10 mol ethoxylated acrylic acid allyl ether was added, and further cooled to 5° C. while the whole mixture was stirred. In this way, a monomer solution was obtained.

Under a thermally insulated condition, the monomer solution was polymerized with a mixture of 150 ppm of hydrogen peroxide, 200 ppm of azobis-(2-amidinopropene) dihydrochloride, 350 ppm of sodium persulfate, and 100 ppm of sodium erythorbate, and maintained at or near a peak temperature (Tmax) for 25 minutes. The obtained hydrogel polymer was cut, shaped by extruding with use of an extruder, and then dried in a dryer at 175° C. until a final moisture content of less than 5 weight % was reached. The obtained dried polymer was pulverized roughly with use of a pulverizer, then further pulverized with a three-stage roll mill, and then, further, particles larger than 850 μm and particles smaller than 150 μm were removed. In this way, comparative water-absorbing resin powder was obtained.

To 400 g of the comparative water-absorbing resin powder, 0.5 weight % of Aerosil 200 fumed silica and 0.2 weight % of aluminum sulfate were added and mixed uniformly. To the obtained mixture, a solution containing 4 g of water, 0.1 weight % of disodium cocoamphopropionate, 0.5 weight % of tetraethylene glycol dimethyl ether, and 1.0 weight % of ethylene carbonate was sprayed, and coated the mixture uniformly. All the values in weight % used here are values relative to the weight of the dried comparative water-absorbing resin powder. The coated comparative water-absorbing resin powder was heated in a forced-air circulation dryer at 180° C. for 20 minutes. In this way, a comparative water-absorbing agent (1-7) was obtained.

Comparative Example 1-8

To 5500 g of an aqueous solution of sodium acrylate having a neutralization rate of 75 mol % (the solution has a monomer concentration of 38 weight %), 4.9 g of polyethylene glycol diacrylate (average addition mole number of ethylene oxide is 9) was dissolved to obtain a reaction liquid. Next, the reaction liquid was supplied to a 10-liter reactor, and the system was subjected to nitrogen gas replacement while the reaction liquid was maintained at 30° C. Next, while the reaction liquid was stirred, 28.3 g of a 10 weight % aqueous solution of sodium persulfate and 1.5 g of a 1 weight % aqueous solution of L-ascorbic acid were added. After about 1 minute, polymerization started. After minutes from the start of the polymerization, a polymerization peak temperature, 86° C., was reached. After minutes from the start of the polymerization, the hydrogel polymer was removed from the reaction liquid after the polymerization. The obtained hydrogel polymer had been grain-refined to particles of approximately 1 mm to 4 mm. The thus-grain-refined hydrogel polymer in the form of particles was spread on a metal gauze having a mesh size of 300 μm, and was dried with hot air at 170° C. for 65 minutes. Next, the obtained dried polymer was pulverized with use of a roll mill, and further subjected to classification using a metal gauze having a mesh size of 850 μm and to blending. In this way, a comparative water-absorbing resin powder having a non-uniformly pulverized shape was obtained.

To 100 parts by weight of the obtained comparative water-absorbing resin powder, 3.93 parts by weight of a surface-crosslinking agent containing 0.55 parts by weight of propylene glycol, 0.03 parts by weight of ethylene glycol diglycidyl ether, 0.35 parts by weight of 1,4-butanediol, and 3 parts by weight of deionized water was added. The mixture was subjected to a heating treatment at 210° C. for 45 minutes to thereby obtain comparative water-absorbing resin particles. To 100 parts by weight of the comparative water-absorbing resin particles, 4 parts by weight of water was further spray-mixed, and the obtained mixture was cured at 60° C. for 1 hour. In this way, a comparative water-absorbing agent (1-8) was obtained.

Comparative Example 1-9

To 5500 g of an aqueous solution of sodium acrylate having a neutralization rate of 75 mol % (the solution has a monomer concentration of 38 weight %), 5.9 g of polyethylene glycol diacrylate (average addition mole number of ethylene oxide is 8) was dissolved to obtain a reaction liquid. Next, the reaction liquid was degassed in a nitrogen gas atmosphere for 30 minutes. Next, the reaction liquid was supplied to a 10-liter reactor, and the system was subjected to nitrogen gas replacement while the reaction liquid was maintained at 30° C. Next, while the reaction liquid was stirred, 2.46 g of sodium persulfate and 0.10 g of L-ascorbic acid were added. After about 1 minute, polymerization started. The polymerization was carried out at 30° C. to 90° C. and, after 60 minutes from the start of the polymerization, the hydrogel polymer was removed from the reaction liquid after the polymerization. The obtained hydrogel polymer had been grain-refined to approximately 5 mm in diameter. The thus-grain-refined hydrogel polymer in the form of particles was spread on a metal gauze having a mesh size of 300 μm, and was dried with hot air at 150° C. for 90 minutes. Next, the obtained dried polymer was pulverized with use of a vibrating mill, and further subjected to classification using a metal gauze having a mesh size of 850 μm and to blending. In this way, a comparative water-absorbing resin having a non-uniformly pulverized shape was obtained.

To 100 parts by weight of the obtained comparative water-absorbing resin, 3.83 parts by weight of a surface-crosslinking agent containing 0.03 parts by weight of ethylene glycol glycidyl ether, 0.5 parts by weight of propylene glycol, 0.3 parts by weight of 1,4-butanediol, and parts by weight of deionized water was mixed. The mixture was subjected to a heating treatment at 200° C. for 45 minutes to thereby obtain comparative water-absorbing resin particles.

On the other hand, to a 500-milliliter separable flask equipped with a condenser, a stirrer blade and a motor, 10 g of acrylic acid, 10 g of lauryl acrylate, 0.1 g of 2,2'-azobis isobutyronitrile (AIBN) as an initiator, and 80 g of ethyl alcohol as a solvent were placed and dissolved completely to obtain a reaction liquid. Next, the reaction liquid was degassed in a nitrogen gas atmosphere for 15 minutes. Next, the separable flask containing the reaction liquid was immersed in a hot-water bath having temperature of 65° C. under a nitrogen stream, and a polymerization reaction was carried out for 2 hours with stirring. The temperature was raised to 75° C. after 2 hours, and the reaction was continued for another 1 hour. After that, the reaction liquid was cooled. In this way, a polymeric-additive-containing solution containing 20 weight % of an acrylic acid-lauryl acrylate copolymer (which is a polymeric additive) was obtained.

To 100 parts by weight of the comparative water-absorbing resin, 5 parts by weight (1 part by weight of polymeric additive) of the polymeric-additive-containing solution (20 weight % ethanol solution) was added and mixed, and then dried in a vacuum at 60° C. for 3 hours. In this way, a comparative water-absorbing agent (1-9) was obtained.

The comparative water-absorbing agent (1-9) had a surface tension of 64.0 mN/m.

[2. Evaluation]

The water-absorbing agents obtained in Examples and Comparative Example were measured for the foregoing physical properties. Furthermore, in accordance with the following methods, powder property parameters were measured, a feed property evaluation test was carried out, standard deviation (σ) of feed rate was measured, a probe insertion test was carried out, absorbent body performance test was carried out, and a feed test in a high-humidity environment was carried out.

[1. Measurement of Powder Property Parameters]

With use of a powder tester (model: PT-X) manufactured by HOSOKAWA MICRON CORPORATION, four parameters (angle of repose, angle of difference, bulk density, and compressibility rate) of powder properties of each water-absorbing agent were measured. Note that the temperature in an environment in which the measurements were carried out was 23.5° C., and the relative humidity in the environment was 38% RH.

(1-1. Angle of Repose)

90 g of a well-mixed water-absorbing agent was weighed out in a 250-milliliter polypropylene container. A vat-fixing unit, a vat, a table-type angle-of-repose-measuring apparatus (product number: XS-24), and a funnel for measuring angle of repose 5 mm in diameter (product number: XS-26), which are included with the powder tester, were attached to the body of the powder tester, and the sample was poured into the tester from the top of the funnel. The sample was allowed to fall while the funnel was shaken with an amplitude of 1.5 mm to form an angle of repose. After all the sample had fallen, the shaking was stopped, and the angle of repose was measured.

(1-2. Angle of Difference)

After the angle of repose was measured as above, a shock was applied once to the table with use of an automatic shocker, and thereby an angle of fall was formed and measured. Next, the angle of difference was calculated in accordance with the following equation.

$$\text{Angle of difference (degree)} = \text{Angle of repose} - \text{Angle of fall}$$

(1-3. Bulk Density (Loose Bulk Density))

A vat, a tapping lift bar, a stationary chute, a chute bracket, a chute for 25 cc, and a 25 cc bulk density measuring cup whose weight had been accurately measured to 0.01 g, which are included with the powder tester, were attached to the body of the powder tester. 50 g of a well-mixed water-absorbing agent was weighed out in a 250-milliliter polypropylene container, the tapping lift bar was raised, and then the sample was poured from the top of the chute until the sample overflowed from the measuring cup so that the sample would completely fill the measuring cup. The water-absorbing agent on the top of the measuring cup was leveled off with a metal blade that is included with the powder tester, the weight of the measuring cup containing the water-absorbing agent therein was accurately measured to 0.01 g, and bulk density (loose bulk density) was calculated. The bulk density (loose bulk density) is calculated using the following equation.

$$\text{Loose bulk density (g/ml)} = (\text{Weight of cup containing water-absorbing agent therein} - \text{Weight of empty cup})/25$$

(1-4. Compressibility Rate)

After the measurement of the loose bulk density, a cap which is included with the powder tester and which has the same inner diameter as the cup was attached to the cup, and the cup was attached to the powder tester. 50 g of a well-mixed water-absorbing agent was weighed out in a 250-milliliter polypropylene container, and the sample was poured from the top of the chute until the sample overflowed from the measuring cup so that the sample would completely fill the measuring cup. The number of taps was set to 180, and tapping was started. The length of stroke of each tap was fixed at 18 mm. After finishing tapping, the cap was removed, the water-absorbing agent on the top of the measuring cup was leveled off with the metal blade coming with the powder tester, the weight of the measuring cup containing the water-absorbing agent therein was measured accurately to 0.01 g, and tight bulk density was calculated. The tight bulk density is calculated using the following equation.

$$\text{Tight bulk density (g/ml)} = (\text{Weight of cup containing water-absorbing agent therein after tapping} - \text{Weight of empty cup})/25$$

Next, the compressibility rate was calculated using the following equation.

$$\text{Compressibility rate (\%)} = (\text{Tight bulk density} - \text{Loose bulk density})/\text{Tight bulk density} \times 100$$

[2. Feed Property Evaluation Test]

With regard to the water-absorbing agents obtained in Examples and Comparative Examples, their K-indices were calculated from the measured parameters of the foregoing powder properties. Based on the value of the K-index, each of the water-absorbing agents was evaluated on the following five-point scale (K-index ranking).

K-Index Ranking
A: 90 or more
B: 80 or more and less than 90
C: 70 or more and less than 80
D: 50 or more and less than 70
E: Less than 50

Similarly, with regard to each of the water-absorbing agents obtained in Examples and Comparative Examples, the foregoing value of the moisture absorption blocking ratio (B.R.) of the water-absorbing agent was evaluated on the following five-point scale (B.R. ranking).

B.R. Ranking
A: 20% or less
B: More than 20% and 40% or less
C: More than 40% and 70% or less
D: More than 70% and 80% or less
E: More than 80%

In the K-index ranking and B.R. ranking, the rank "A" is best, and a water-absorbing agent whose K-index is ranked as "A" and whose B.R. is ranked as "A" shows an excellent physical property. The rank "E" is worst. The ranks A, B, and C are good, whereas the ranks D and E may cause some problem in feed property.

With regard to each of the water-absorbing agents, a lower one of its ranks in the K-index and B.R. rankings was used as the overall rank of that water-absorbing agent. If each of the ranks in the K-index and B.R. rankings is A, B or C, such a water-absorbing agent is excellent in feed property, and can be stably and accurately supplied at a desired feed rate. However, if at least one of the ranks in the K-index and B.R. rankings is D or E, such a water-absorbing agent is poor in feed property, and this may make it difficult to ensure a stable feed rate.

[3. Measurement of Standard Deviation ($\sigma$) of Feed Rate]

The standard deviation ($\sigma$) of feed rate was measured with use of a bulk solid pump (model: K-ML-BSP-125) manufactured by Coperion K-tron. The weight of fed powder for use in calculation of feed rate was measured with use of a balance scale which is disposed below an outlet of the feeder and which is capable of measurement with an accuracy of 0.1 g (e.g., model GP-30K manufactured by A&D Company, Limited). Note that the temperature of an environment in which the feeding was carried out was 23.5° C. and the relative humidity of the environment was 38% RH.

20.0 kg of a water-absorbing agent was introduced into a hopper at the upper portion of the feeder, the mode of the feeder was set to gravimetric mode and the flow rate was set to 100 kg/hr. (=1667 g/min.), and the feeder was operated for 10 minutes. The gravimetric mode is such that the feed rate during operation is automatically measured by a scale that is included with the feeder, the measured feed rate is fed back to the feeder, the rotation speed of disks is automatically adjusted, and thereby a deviation from the set feed rate is automatically corrected. From the start of the operation of the feeder to the end of the operation of the feeder, the weight indicated by the balance scale (total weight (g) of discharged powder) was read and recorded every 10 seconds.

Among the total weights (g) of discharged powder recorded every 10 seconds, those obtained within a period from 1 minute after the start of the operation to 9 minutes after the start of the operation were used in calculation. First, based on the difference between two adjacent ones of the total weights (g) of discharged powder recorded every 10 seconds, the amount of increase in weight per 10 seconds (i.e., weight increment) (g/10 sec.) of the powder was calculated. Next, each weight increment (g/10 sec.) of the powder obtained through the above calculation was multiplied by 6 to obtain a feed amount per unit time (i.e., feed rate) (g/min.) Furthermore, the standard deviation ($\sigma$) of the feed amount per unit time (g/min.) was calculated.

[4. Probe Insertion Test]

{Measurement of Probe Insertion Work (PIW) and Probe Insertion Distance (PID)}

(4-1. Sample for Measurement (Measurement Sample))

27 g to 30 g of a water-absorbing agent was placed in a cylinder-type sample tube made of glass (outer diameter: 35 mm, inner diameter: 33 mm, height: 78 mm, e.g., Screw Vial No. 7 manufactured by Maruemu corporation), and shaken well. Then, the sample tube was tapped vertically (three times/second, amplitude: 10 mm) for 1 minute on an iron sheet, and thereby the water-absorbing agent was brought into a condition in which the water-absorbing agent is closely packed within the sample tube. Next, the amount of the water-absorbing agent was adjusted by increasing or decreasing the amount as needed so that the water-absorbing agent filled and closely packed in the sample tube (this water-absorbing agent is hereinafter referred to as "particle bed") would have a height of 45±1.5 mm. In a case where the amount of the water-absorbing agent was adjusted as described above, the sample tube was well shaken again and then, on the iron sheet, tapped vertically (three times/second, amplitude: 10 mm) for 1 minute and thereby the water-absorbing agent was brought into a condition in which it is closely filled. Note that the tapping was carried out so that the top surface of the particle bed after the tapping would be flat and horizontal.

In measurement of the PIW and PID, the average of three measured values is employed. Therefore, every time a measurement was completed, the sample tube having the particle bed formed therein was capped and shaken well, tapped vertically for 1 minute on the iron plate again in the foregoing manner, and thereby a sample for measurement in a state in which the top surface of the particle bed is flat and horizontal was obtained.

(4-2. Measurement Apparatus)

Figure 5:
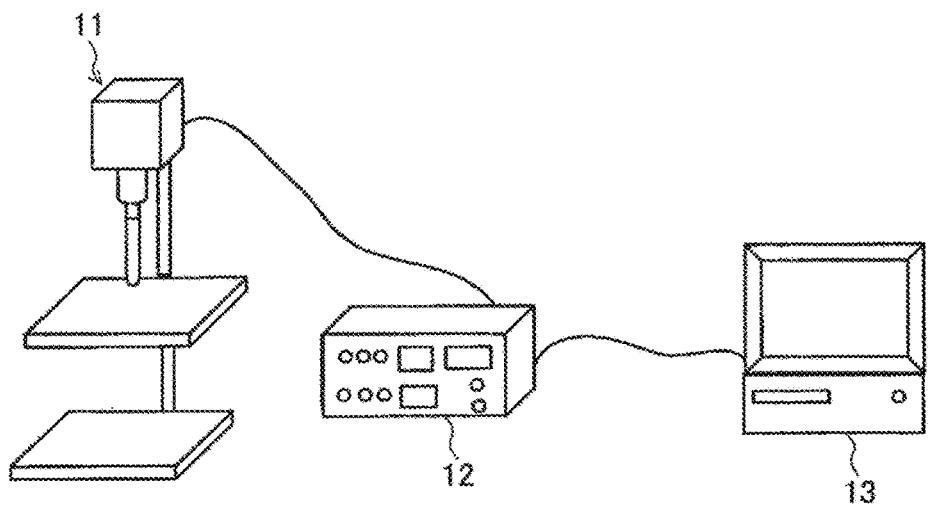
FIG. 5 is a perspective view schematically illustrating a configuration of a measurement apparatus for measuring probe insertion work and probe insertion distance with regard to a water-absorbing agent in accordance with the present invention.

The PIW and PID were measured with use of a measurement apparatus illustrated in FIG. 5. The measurement apparatus (KES-G5 Handy Compression Tester, manufactured by KATO TECH CO., LTD.) includes: a compression device 11; a control device 12 that controls the compression device 11; and a computer 13 that loads data obtained from the control device 12. The compression device 11, the control device 12, and the computer 13 are connected together by cables.

Figure 6:
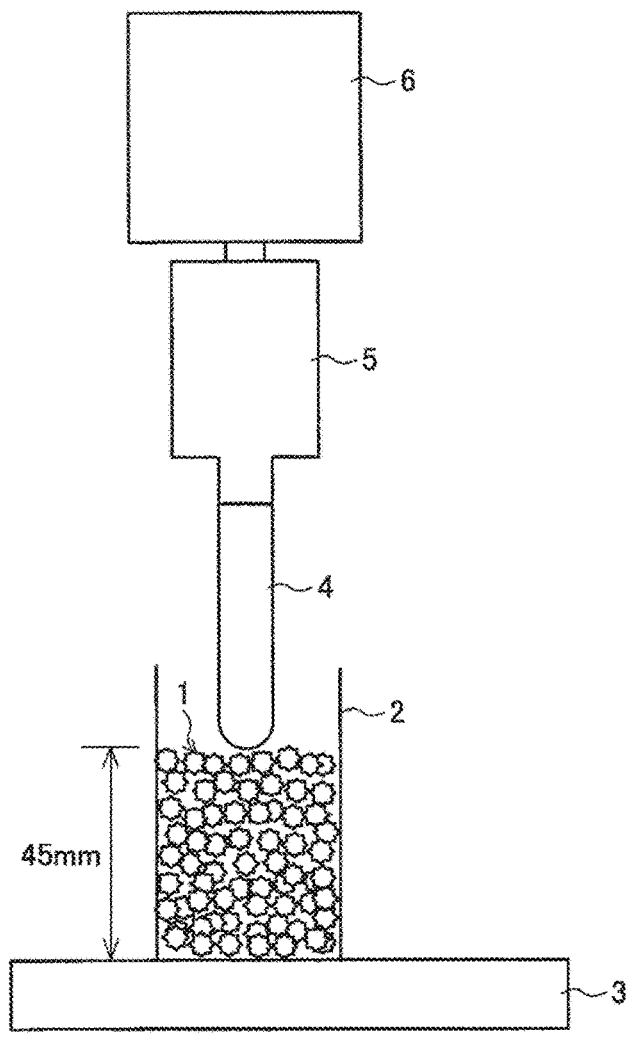
FIG. 6 is an elevation view illustrating main parts of a compression device included in the measurement apparatus.

The compression device 11 includes, as illustrated in FIG. 6, a movable stage 3, an insertion probe (insertion member) 4, a movable load cell (force gage) 5, and a displaced distance detector 6.

Figure 7:
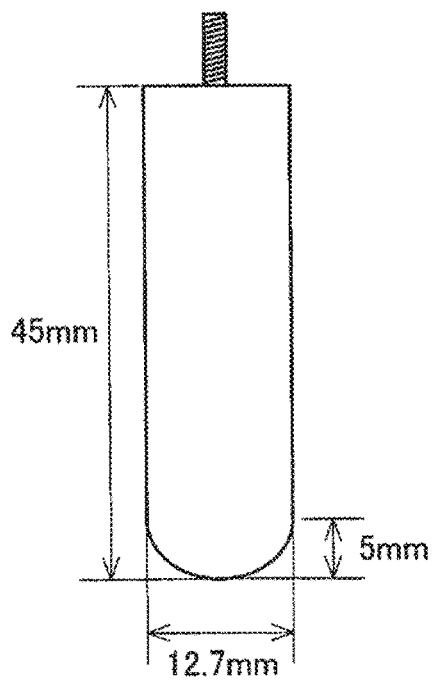
FIG. 7 is an elevation view illustrating an insertion probe included in the compression device.

The stage 3 is a stage on which a measurement sample 2 filled with a water-absorbing agent (hereinafter "particle bed") 1 is to be placed, and is moveable relative to the insertion probe 4. The insertion probe 4 is a metal rod inserted into a particle bed 1 composed of a water-absorbing agent or a water-absorbing resin of the measurement sample 2. In the present example, the insertion probe 4 is a positive electrode made of aluminum oxide having a diameter of 12.7 mm and a length of 40 mm with a spherically made end (round end) having a radius of 5 mm (see FIG. 7). Note that, with regard to a surface roughness of the insertion probe 4 standardized in accordance with JIS B0601-1994, usually, the maximum height is 0 μm to 10 μm, preferably 0 μm to 1 μm, ten-point average roughness is 0 μm to 10 μm, preferably 0 μm to 1 μm, and center line average roughness is 0 μm to 5 μm, preferably 0 μm to 1 μm. The insertion probe 4 is attached to (screwed to) the load cell 5 (FIG. 6) as is apparent from FIG. 7, and is movable together with the load cell 5.

The load cell 5 applies, to the particle bed 1 of the measurement sample 2 via the insertion probe 4, a load that varies in magnitude with an upper limit of 10 kg. The load cell 5 is joined to the displaced distance detector 6 as illustrated in FIG. 6, and is movable relative to the measurement sample 2. The displaced distance detector 6 detects the distance traveled by the load cell 5, i.e., displaced distance.

The control device 12 illustrated in FIG. 5 includes: an insertion speed regulator that regulates the speed of insertion of the insertion probe 4; a load regulator that regulates a load applied from the insertion probe 4 to the particle bed of the measurement sample 2; a displaced distance regulator that regulates the displaced distance of the load cell 5; a displaced distance indicator that indicates the displaced distance of the load cell 5; a load indicator that indicates a load applied to the particle bed of the measurement sample 2; and an integrator.

The computer 13 illustrated in FIG. 5 loads data obtained from the compression device 11 and the control device 12 as digital data. The computer 13 has recorded therein the displaced distance of the insertion probe 4 (i.e., load cell 5) that makes contact with the top surface of the particle bed 1 of the measurement sample 2, the load applied to the particle bed 1, and the like.

(4-3. Conditions Under which Measurement is Carried Out, and Measurement Method)

The measurement apparatus was placed on a horizontal, vibration-free testing bench, and the measurement of PIW and PID was carried out in the following manner in an environment in which the temperature and relative humidity had been adjusted to 25±1° C. and relative humidity 50±5%, respectively.

Specifically, the measurement sample 2 was prepared in the foregoing manner, and was placed on the stage 3 of the compression device 11 (FIG. 5) of the measurement apparatus while avoiding vibrations as much as possible. Next, the stage 3 was raised to a position at which the tip of the insertion probe 4 illustrated in FIG. 6 touches the top surface of the particle bed 1 of the measurement sample 2, and fixed. This position was used as a starting point (0 mm).

Then, the tip of the insertion probe 4 was allowed to enter the particle bed 1 at an insertion speed of 1 mm/second. Concurrently with the start of the entry of the insertion probe 4, a measurement was started at a data load interval of 0.1 seconds, and the distance the insertion probe 4 was inserted and the load required for the insertion probe 4 to insert were measured. Note that the distance the insertion probe 4 was inserted was within the range of from the starting point (0 mm) to 20 mm (error of the distance was within ±3%).

Figure 8:
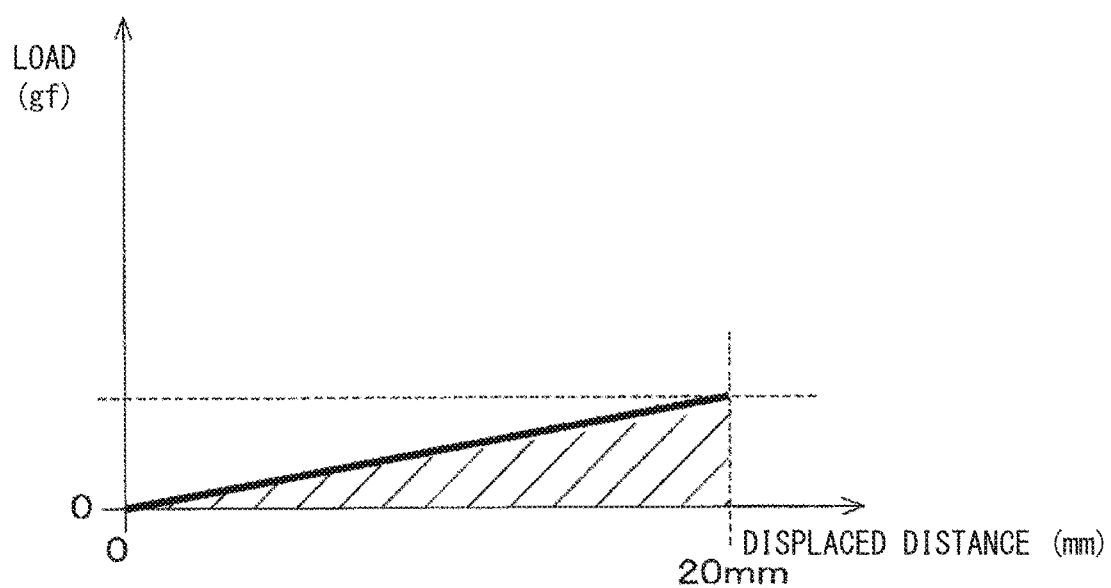
FIG. 8 is a chart showing an example of loads required for the insertion probe to insert into a particle bed, at respective probe insertion distances.

As shown in FIG. 8, a chart was created with the above-measured distance inserted (mm) on the horizontal axis and the measured load (gram force, or gf) on the vertical axis. The area between a curve connecting the obtained loads and the horizontal axis (this area is hatched in FIG. 8) was integrated within the range of from the distance 0 mm to 20 mm to obtain a probe insertion work (PIW), which is a work done when the insertion probe 4 is inserted by a distance of 0 mm to 20 mm.

The above measurement operation was carried out three times, and the average of the obtained three values was used as a measured value. A water-absorbing agent of the particle bed 1, having a smaller PIW (determined in the above manner), can be considered more slidable as particles and better in handleability.

Note that the upper limit of the load was 10 kgf. In a case where the load reached 10 kgf before the distance the insertion probe 4 was inserted reached 20 mm, the PIW (gf×mm) and PID (mm) up to that point in time were calculated.

[5. Absorbent Body Performance Test]

Absorbent articles were produced from the water-absorbing agents obtained in Examples and Comparative Examples, and evaluated for hand feeling (how it feels when touched).

(5-1. Production of Absorbent Article)

50 parts by weight of a water-absorbing agent and 50 parts by weight of wood-ground pulp were dry-mixed with use of a mixer. On a 400-mesh wire screen (mesh size of 38 μm), the resulting mixture was formed into a web measuring 120 mm×400 mm, via air-laid paper making carried out with use of a batch-type air-laid paper making device. Next, the web was pressed for 5 seconds at a pressure of 196.14 kPa to obtain an absorbent body in which the basis weight of the water-absorbing agent was approximately 0.047 g/cm$_2$.

Next, a liquid impermeable back sheet (liquid impermeable sheet) made of polypropylene and having a so-called leg gather, the absorbent body, and a liquid permeable top sheet (liquid permeable sheet) made of polypropylene were bonded to each other in this order with use of double-sided tape. Thereafter, a so-called tape fastener was fixed to these members bonded to each other, and thus an absorbent article (i.e., a disposable diaper) was produced. The absorbent article had a weight of 46 g.

(5-2. Method of Evaluating Hand Feeling)

The absorbent article produced was spread out flat so that the liquid permeable top sheet faced upward. A resin cylinder (inner diameter: 70 mm, inner volume: 346 cm$^3$) was placed in a center part of the absorbent article. Thereafter, 300 mL of a degradation test liquid (an aqueous solution obtained by mixing L-ascorbic acid into a 0.90 weight % aqueous sodium chloride solution) was poured into the cylinder in a manner so as not to overflow. After all of the degradation test liquid was absorbed by the absorbent article, the absorbent article having the liquid absorbed therein was placed into a polypropylene bag (re-sealable plastic bag with zipper, Uni-Pack 1-4, manufactured by SEISANNIPPONSHA Ltd.), and the bag was sealed with the zipper after air in the bag was removed as much as possible.

Thereafter, the bag sealed thusly was allowed to stand for 2 hours in an incubator set to 60±2° C. After 2 hours of standing, the absorbent article was removed from the bag, the top sheet (into which the degradation test liquid had been poured) was touched, and the degree of stickiness was evaluated based on the following five-point scale. Evaluation was carried out by at least five evaluators, and the average value was used as the evaluation score.

Degree of Stickiness

1: Not sticky

2: Almost not sticky

3: Slightly sticky

4: Sticky

5: Very sticky

[6. Feed Test in High-Humidity Environment]

A feed test in a high-humidity environment was carried out with use of a DRY MATERIAL FEEDER (product name: ACCURATE 300, manufactured by KUMA engineering Co., LTD.). A screw used was a spring-type screw such that: total length of the screw part is 30 cm, screw pitch is 2 cm, screw shape is 4 mm (horizontal dimension)×4.5 mm (dimension along rotation axis), outer diameter is 2.6 cm, and the material for screw is SUS304. A pipe used is made of SUS304, the inner diameter of the pipe is 2.9 cm, and the length of the pipe was adjusted to the extent that the pipe can store the screw before use. The feeder was equipped with a hopper that is capable of containing the whole amount of a water-absorbing agent (described later). The temperature of an environment (i.e., high-humidity environment) in which the feed test was carried out had been adjusted to 25° C. and the relative humidity of this environment had been adjusted to 80% RH.

50 kg of a water-absorbing agent was introduced into the hopper of the feeder. The feeder was set such that the feed rate would be 50 kg/hr, and continuous operation (about 1 hour) was carried out until the water-absorbing agent was entirely discharged. Note that the relationship between the set feed rate and the actual feed rate varies from one feeder to another. Therefore, before carrying out the feed test, a calibration curve between the actual feed rate of the water-absorbing agent and the set feed rate was created with regard to the feeder actually used, and a set feed rate corresponding to the desired feed rate was selected based on the calibration curve.

After the water-absorbing agent had been entirely discharged from the feeder, the inside of the feeder and the inside of the hopper were checked for adhesion of the water-absorbing agent to the inner wall of the feeder and the surface of the screw. The degree of adhesion of each water-absorbing agent was evaluated based on the following five-point scale (adhesion evaluation index).

Adhesion Evaluation Index

1: There is no or little adhesion of water-absorbing agent

2: There is slight adhesion of water-absorbing agent

3: There is adhesion of water-absorbing agent

4: There is much adhesion of water-absorbing agent

5: Adhesion of water-absorbing agent is too much and therefore water-absorbing agent cannot be stably fed during continuous operation (due to, for example, clogging of screw part, bridging in hopper)

The results of measurement are shown in Tables 1 to 6 below.

TABLE 1

Results of measurement of physical properties

| Examples | CRC [g/g] | AAPO. 3 [g/g] | AAPO. 7 [g/g] | B. R. [%] | F. R. [g/s] |
|---|---|---|---|---|---|
| Ex. 1-1 | 32.2 | 32.5 | 25.5 | 3 | 12.6 |
| Ex. 1-2 | 32.6 | 32.1 | 26.0 | 62 | 12.6 |
| Ex. 1-3 | 31.9 | 32.4 | 25.5 | 35 | 12.0 |
| Ex. 1-4 | 32.0 | 31.2 | 24.8 | 30 | 12.2 |
| Ex. 1-5 | 31.7 | 30.7 | 24.9 | 6 | 11.4 |
| Ex. 1-6 | 32.2 | 31.4 | 24.5 | 61 | 13.3 |
| Ex. 1-7 | 32.5 | 31.7 | 25.0 | 30 | 12.5 |
| Ex. 1-8 | 32.5 | 30.9 | 24.8 | 50 | 12.8 |
| Ex. 1-9 | 35.1 | 30.5 | 21.1 | 0 | 13.2 |
| Ex. 1-10 | 34.8 | 31.0 | 21.7 | 0 | 13.0 |
| Ex. 1-11 | 37.8 | 32.1 | 20.8 | 2 | 12.4 |
| Ex. 1-12 | 38.3 | 31.9 | 20.1 | 9 | 11.5 |
| Ex. 1-13 | 31.8 | 32.0 | 25.1 | 19 | 12.4 |
| Ex. 1-14 | 32.0 | 31.8 | 25.3 | 20 | 11.9 |
| Ex. 1-15 | 32.4 | 32.0 | 25.3 | 3 | 12.7 |
| Ex. 1-16 | 38.0 | 31.3 | 19.9 | 15 | 11.7 |
| Ex. 1-17 | 35.3 | 31.0 | 20.8 | 0 | 12.8 |
| Ex. 1-18 | 32.1 | 32.5 | 25.5 | 25 | 12.7 |
| Ex. 1-19 | 32.0 | 31.0 | 25.3 | 34 | 11.8 |
| Ex. 1-20 | 32.4 | 31.6 | 25.0 | 10 | 12.3 |
| Ex. 1-21 | 38.4 | 31.1 | 20.0 | 41 | 12.5 |
| Com. Ex. 1-1 | 32.6 | 31.5 | 24.2 | 40 | 10.3 |
| Com. Ex. 1-2 | 33.4 | 31.2 | 24.5 | 5 | 9.7 |
| Com. Ex. 1-3 | 34.9 | 30.5 | 24.4 | 99 | 12.3 |
| Com. Ex. 1-4 | 34.6 | 31.1 | 24.8 | 96 | 13.3 |
| Com. Ex. 1-5 | 32.1 | 32.1 | 25.0 | 89 | 12.0 |
| Com. Ex. 1-6 | 35.2 | 29.7 | 18.6 | 0 | 9.4 |
| Com. Ex. 1-7 | 29.4 | 28.4 | 19.0 | 0 | 9.3 |
| Com. Ex. 1-8 | 31.5 | 30.8 | 21.2 | 78 | 11.7 |
| Com. Ex. 1-9 | 34.2 | 30.5 | 21.2 | 0 | 10.7 |

Note:
"Ex." stands for "Example", "Com. Ex." stands for "Comparative Example"

TABLE 2

Results of measurement of powder property parameters

| Examples | Angle of repose [°] | Angle of Difference [°] | Compressibility rate [%] | Bulk density [g/mL] | K-Index |
|---|---|---|---|---|---|
| Ex. 1-1 | 36.9 | 6.6 | 12.0 | 0.68 | 90.1 |
| Ex. 1-2 | 33.4 | 8.4 | 8.9 | 0.72 | 109.3 |
| Ex. 1-3 | 35.1 | 9.1 | 10.1 | 0.70 | 97.0 |
| Ex. 1-4 | 37.2 | 8.8 | 11.0 | 0.73 | 74.7 |
| Ex. 1-5 | 37.8 | 8.5 | 10.6 | 0.72 | 79.6 |
| Ex. 1-6 | 32.2 | 9.6 | 9.5 | 0.76 | 93.0 |
| Ex. 1-7 | 34.1 | 10.1 | 10.2 | 0.73 | 87.6 |
| Ex. 1-8 | 37.0 | 8.0 | 10.2 | 0.77 | 72.9 |
| Ex. 1-9 | 34.6 | 9.7 | 8.6 | 0.75 | 94.1 |
| Ex. 1-10 | 35.4 | 11.3 | 9.7 | 0.76 | 74.0 |
| Ex. 1-11 | 37.1 | 6.8 | 12.3 | 0.69 | 83.4 |
| Ex. 1-12 | 37.4 | 8.7 | 10.5 | 0.72 | 81.2 |
| Ex. 1-13 | 36.2 | 6.4 | 11.8 | 0.68 | 94.9 |
| Ex. 1-14 | 36.9 | 8.8 | 11.3 | 0.70 | 76.3 |
| Ex. 1-15 | 38.2 | 7.6 | 12.1 | 0.68 | 81.1 |
| Ex. 1-16 | 37.0 | 8.4 | 10.3 | 0.71 | 88.1 |
| Ex. 1-17 | 34.5 | 9.6 | 8.8 | 0.73 | 99.0 |
| Ex. 1-18 | 33.5 | 10.2 | 9.7 | 0.71 | 99.2 |
| Ex. 1-19 | 36.5 | 9.0 | 10.9 | 0.71 | 83.1 |
| Ex. 1-20 | 36.2 | 7.1 | 11.5 | 0.69 | 91.9 |
| Ex. 1-21 | 38.0 | 8.1 | 10.6 | 0.72 | 80.3 |
| Com. Ex. 1-1 | 34.2 | 11.4 | 13.9 | 0.69 | 65.1 |
| Com. Ex. 1-2 | 38.5 | 7.6 | 15.2 | 0.66 | 61.3 |
| Com. Ex. 1-3 | 30.9 | 13.3 | 10.2 | 0.77 | 76.3 |
| Com. Ex. 1-4 | 30.1 | 13.0 | 10.4 | 0.78 | 75.8 |
| Com. Ex. 1-5 | 32.6 | 11.1 | 10.0 | 0.76 | 82.4 |
| Com. Ex. 1-6 | 36.1 | 10.9 | 16.2 | 0.67 | 47.6 |
| Com. Ex. 1-7 | 36.6 | 8.9 | 15.0 | 0.68 | 59.4 |
| Com. Ex. 1-8 | 32.6 | 11.1 | 10.0 | 0.76 | 82.4 |
| Com. Ex. 1-9 | 34.9 | 9.2 | 14.8 | 0.69 | 63.1 |

Note:
"Ex." stands for "Example", "Com. Ex." stands for "Comparative Example"

TABLE 3

Results of feed property evaluation test

| Examples | K-Index | K-Index rank | B. R. [%] | B. R. rank | Overall rank on feed property | Standard deviation (σ) of feed rate |
|---|---|---|---|---|---|---|
| Ex. 1-1 | 90.1 | A | 3 | A | A | 18.9 |
| Ex. 1-2 | 109.3 | A | 62 | C | C | 6.3 |
| Ex. 1-3 | 97.0 | A | 35 | B | B | 20.0 |
| Ex. 1-4 | 74.7 | C | 30 | B | C | 25.5 |
| Ex. 1-5 | 79.6 | C | 6 | A | C | 26.8 |
| Ex. 1-6 | 93.0 | A | 61 | C | C | 15.0 |
| Ex. 1-7 | 87.6 | B | 30 | B | B | 27.9 |
| Ex. 1-8 | 72.9 | C | 50 | C | C | 30.1 |
| Ex. 1-9 | 94.1 | A | 0 | A | A | 10.5 |
| Ex. 1-10 | 74.0 | C | 0 | A | C | 25.0 |
| Ex. 1-11 | 83.4 | B | 2 | A | B | 25.7 |
| Ex. 1-12 | 81.2 | B | 9 | A | B | 23.6 |
| Ex. 1-13 | 94.9 | A | 19 | A | A | 12.9 |
| Ex. 1-14 | 76.3 | C | 20 | A | C | 21.4 |
| Ex. 1-15 | 81.1 | B | 3 | A | B | 25.5 |
| Ex. 1-16 | 88.1 | B | 15 | A | B | 23.8 |
| Ex. 1-17 | 99.0 | A | 0 | A | A | 5.2 |
| Ex. 1-18 | 99.2 | A | 25 | B | B | 17.1 |
| Ex. 1-19 | 83.1 | B | 34 | B | B | 25.1 |
| Ex. 1-20 | 91.9 | A | 10 | A | A | 26.6 |
| Ex. 1-21 | 80.3 | B | 41 | C | C | 23.1 |
| Com. Ex. 1-1 | 65.1 | D | 40 | B | D | 35.3 |
| Com. Ex. 1-2 | 61.3 | D | 5 | A | D | 47.8 |
| Com. Ex. 1-3 | 76.3 | C | 99 | E | E | 26.5 |
| Com. Ex. 1-4 | 75.8 | C | 96 | E | E | 21.2 |
| Com. Ex. 1-5 | 82.4 | B | 89 | E | E | 33.2 |
| Com. Ex. 1-6 | 47.6 | E | 0 | A | E | 50.5 |
| Com. Ex. 1-7 | 59.4 | D | 0 | A | D | 38.0 |

TABLE 3-continued

Results of feed property evaluation test

| Examples | K-Index | K-Index rank | B. R. [%] | B. R. rank | Overall rank on feed property | Standard deviation (σ) of feed rate |
|---|---|---|---|---|---|---|
| Com. Ex. 1-8 | 82.4 | B | 78 | D | D | 7.6 |
| Com. Ex. 1-9 | 63.1 | D | 0 | A | D | 34.5 |

Note:
"Ex." stands for "Example", "Com. Ex." stands for "Comparative Example"

TABLE 4

Results of probe insertion test

| Examples | PIW [gf × mm] | PID [mm] |
|---|---|---|
| Ex. 1-1 | 4688 | 20 |
| Ex. 1-2 | 4210 | 20 |
| Ex. 1-5 | 9225 | 20 |
| Ex. 1-6 | 4599 | 20 |
| Ex. 1-9 | 4487 | 20 |
| Ex. 1-10 | 4386 | 20 |
| Com. Ex. 1-1 | 59855 | 20 |
| Com. Ex. 1-2 | 37665 | 20 |
| Com. Ex. 1-3 | 4717 | 20 |
| Com. Ex. 1-4 | 4421 | 20 |
| Com. Ex. 1-6 | 36686 | 13 |

Note:
"Ex." stands for "Example", "Com. Ex." stands for "Comparative Example"

TABLE 5

Results of absorbent body performance test

| Examples | Degree of stickiness |
|---|---|
| Ex. 1-1 | 1.6 |
| Ex. 1-5 | 2.6 |
| Ex. 1-10 | 2.6 |
| Ex. 1-11 | 1.8 |
| Com. Ex. 1-4 | 5.0 |
| Com. Ex. 1-9 | 4.2 |

Note:
"Ex." stands for "Example", "Com. Ex." stands for "Comparative Example"

TABLE 6

Results of feed test in high-humidity environment

| Examples | K-index rank | B.R. rank | Overall rank on feed property | Adhesion evaluation index |
|---|---|---|---|---|
| Ex. 1-1 | A | A | A | 1 |
| Ex. 1-2 | A | C | C | 3 |
| Ex. 1-7 | B | B | B | 2 |
| Ex. 1-9 | A | A | A | 1 |
| Ex. 1-14 | C | A | C | 1 |
| Ex. 1-21 | B | C | C | 2 |
| Com. Ex. 1-3 | C | E | E | 5 |
| Com. Ex. 1-5 | B | E | E | 4 |
| Com. Ex. 1-8 | B | D | D | 4 |

Note:
"Ex." stands for "Example", "Com. Ex." stands for "Comparative Example"

[7. Results of Evaluation]

The water-absorbing agents of Examples have high K-index and low moisture absorption blocking ratio (B.R.), and therefore do not place significant effects on the degree of feed property that varies depending on the feeding environment. Therefore, both in a dry condition and high-humidity environment, the adhesion of the water-absorbing agent to the inner wall of the apparatus was prevented or reduced, and the water-absorbing agent was supplied at a desired feed rate stably. In contrast, with regard to the water-absorbing agents of Comparative Examples, either or both of the K-index and B.R. ranks was/were D or E; therefore, in a dry condition and/or high-humidity environment, the water-absorbing agents were poor in feed property, and, due to, for example, adhesion of the water-absorbing agents to the inner wall of the apparatus, stable feed rate could not be ensured.

Examples Concerning Water-Absorbing Agent in Accordance with Embodiment 2

The following are Examples concerning a water-absorbing agent in accordance with the foregoing <Embodiment 2>.

The following description will discuss the present invention in greater detail on the basis of Examples and Comparative Examples below. Note, however, that the present invention is not limited to the description thereof and that the present invention also encompasses in its scope any Example derived from a combination of technical means disclosed in different Examples.

Note that with regard to measurements of physical properties which are the same as the measurements of physical properties of a water-absorbing agent or water-absorbing resin specified in Examples concerning a water-absorbing agent of the foregoing <Embodiment 1>, descriptions therefor are omitted here.

(a) Bulk Density (EDANA Method) and Flow Rate

In the present specification, the "bulk density (EDANA method)" and "flow rate" of a particulate water-absorbing agent or water-absorbing resin in accordance with the present invention were measured in conformity with an EDANA method (ERT460.2-02).

(b) Logarithmic Standard Deviation ($\sigma\zeta$) of Particle Size Distribution Water-absorbing resin particles or water-absorbing agent were/was sifted with use of JIS standard sieves having mesh sizes of, for example, 850 μm, 600 μm, 500 μm, 300 μm, 150 μm, and 45 μm, and a residual percentage R for each sieve was plotted on logarithmic probability paper. The logarithmic standard deviation ($\sigma\zeta$) is represented by the following equation, where X1 is the particle diameter when R=84.1% and X2 is the particle diameter when R=15.9%. A smaller value of the logarithmic standard deviation ($\sigma\zeta$) indicates a narrower particle size distribution.

$$\sigma\zeta = 0.5 \times \ln(X2/X1)$$

A method of classification in determining the logarithmic standard deviation ($\sigma\zeta$) of particle size distribution is as follows. 10.0 g of water-absorbing resin particles or water-absorbing agent is/are placed in a JIS standard sieve (THE IIDA TESTING SIEVE, 8 cm in diameter) having a mesh size of 85 μm, 600 μm, 500 μm, 300 μm, 150 μm, or 45 μm, and subjected to classification for 5 minutes with use of a vibration classifier (IIDA SIEVE SHAKER, TYPE: ES-65, SER. No. 0501).

(c) Saline Flow Conductivity (SFC)

The saline flow conductivity (SFC) of a particulate water-absorbing agent or water-absorbing resin in accordance with the present invention was measured in conformity with a measuring method disclosed in U.S. Pat. No. 5,669,894.

(d) Moisture Absorption Blocking Ratio (B.R.; Blocking Ratio)

On an aluminum cup having a diameter of 52 mm, 2 g of a particulate water-absorbing agent or water-absorbing resin was uniformly spread out and then allowed to stand for one hour in a thermo-hygrostat (PLATINOUSLUCIFERPL-2G; manufactured by Tabai Espec Corp.) at a temperature of 25° C. and at a relative humidity of 90±5% RH. Thereafter, the particulate water-absorbing agent or the water-absorbing resin in the aluminum cup was gently transferred onto a JIS standard sieve (The IIDA TESTING SIEVE: 80 mm in inner diameter) having a mesh size of 2000 μm (JIS 8.6 mesh). The particulate water-absorbing agent or the water-absorbing resin was then classified at room temperature (20° C. to 25° C.) and at a relative humidity of 50% RH for 5 seconds, by using a Ro-Tap sieve shaker (ES-65 sieve shaker manufactured by Sieve Factory Iida Co., Ltd.; whose rotation speed was 230 rpm and number of impacts was 130 rpm). A weight (W1 [g]) of the particulate water-absorbing agent or the water-absorbing resin remaining on the JIS standard sieve and a weight (W2 [g]) of the particulate water-absorbing agent or the water-absorbing resin which had passed through the JIS standard sieve were measured. The moisture absorption blocking ratio was calculated using the following equation.

Moisture absorption blocking ratio (*B.R.*) [weight %]=$\{W1/(W1+W2)\} \times 100$ Note that a lower value of the moisture absorption blocking ratio means better moisture absorption flowability.

(e) Re-Wet

There are known several methods for measuring a re-wet. The following measuring method is one example of the measuring methods, and how to measure a re-wet is not limited to such a measuring method.

A pulp sheet measuring 12 cm×38 cm was prepared using 8.5 g of wood-ground pulp. Then, 11.3 g of a particulate water-absorbing agent or water-absorbing resin obtained in Examples concerning water-absorbing agent in accordance with Embodiment 2 was uniformly spread on the pulp sheet, and, on top of the particulate water-absorbing agent or water-absorbing resin, another pulp sheet having the same size and weight as the above pulp sheet was placed, and a pressure of 3.8 kg/cm² was applied for 1 minute to thereby prepare an absorbent sheet measuring 12 cm×38 cm and having a thickness of 5.5 mm. Then, the absorbent sheet was spread out flat, and a resin cylinder (outer diameter: 100 mm, inner diameter: 25 mm, height: 220 mm, weight: 3.6 kg, inner capacity: 108 cm³) was placed in the central portion of the sheet.

First liquid injection was carried out as follows. 100 g of 0.90 weight % aqueous sodium chloride solution was poured into the resin cylinder at 7 ml/s, and the time taken for the article to absorb all the aqueous sodium chloride solution was used as a first liquid absorbing time. The resin cylinder was removed 10 minutes after the addition of the aqueous sodium chloride solution, 10 g (weight W5 (g)) of filter paper (product name: JISP3801, No. 2, thickness: 0.26 mm, retained particle diameter: 5 μm, diameter: 90 mm, manufactured by Advantec Toyo Kaisha, Ltd.) was placed in the central portion, and a cylindrical weight of 2.5 kg (8 cm in diameter) was gently placed on the top surface of the filter paper. After 2 minutes, the cylindrical weight was removed, weight W6 (g) of the filter paper was measured, and a first re-wet was calculated using the following equation.

Re-wet (g)=$W5-W6$

Second liquid injection was carried out in the same manner as the first liquid injection, except that the amount of 0.90 weight % aqueous sodium chloride solution was 50 g and the filter paper used was 20 g. In this way, a second liquid absorbing time and a second re-wet were measured.

(f) Water-Soluble Content (Ext)

The water-soluble content (Ext) of a particulate water-absorbing agent of the present invention was measured in conformity with an EDANA method (ERT470.2-02).

(g) Surface Area

The surface area of a particulate water-absorbing agent of the present invention can be measured by, for example, performing analysis using three-dimensional analysis software (e.g., high-speed three-dimensional analysis software TRI/3D-VOL-FCS64) on a result of measurement with use of a three-dimensional analysis apparatus using x-rays (e.g., Microfocus X-Ray CT System inspeXio SMX-225CT or inspeXio SMX-100CT manufactured by Shimadzu Corporation). When the surface area is measured, the above described internal gas bubble ratio and/or the like can be also measured simultaneously.

<Production Method>

Production Example 1

In a 1-liter polypropylene container having an inner diameter of 80 mm and covered with styrene foam (heat insulating material), the following solution (A) was prepared: a solution composed of a mixture of 291 g of acrylic acid, 0.43 g (0.02 mol % relative to carboxyl-group-containing unsaturated monomers) of polyethylene glycol diacrylate (molecular weight: 523) as an internal crosslinking agent, 1.80 g of 1.0 weight % aqueous trisodium diethylenetriamine pentaacetate, and 3.60 g of 1.0 weight % acrylic acid solution of IRGACURE (registered trademark) 184. A solution (B) composed of a mixture of 247 g of 48.5 weight % aqueous sodium hydroxide solution and 255 g of ion-exchange water having the temperature adjusted to 50° C. was prepared. The solution (A) was stirred with a magnetic stirrer 5 cm in length at 800 rpm and, to this solution (A), the solution (B) was quickly added and mixed to obtain an aqueous monomer solution (C). The temperature of the aqueous monomer solution (C) rose to about 100° C. due to heat of neutralization and heat of dissolution.

Next, 1.8 g of a 3 weight % aqueous sodium persulfate solution was added to the aqueous monomer solution (C), stirred for about 1 second, and then immediately poured in an open system into a stainless steel vat-type vessel whose inner surface had Teflon (registered trademark) attached thereto. While the aqueous monomer solution was being poured into the stainless steel vat-type vessel, an ultraviolet ray was applied to the monomer solution in the vessel.

Soon after the aqueous monomer solution was poured into the vat, polymerization started (temperature at the start of the polymerization was 98° C.), and the polymerization reached a peak temperature within about 1 minute. After 3 minutes, the application of the ultraviolet ray was stopped, and a hydrogel was removed from the vat. Note that this series of operations was carried out in a system open to atmospheric air.

The obtained hydrogel was crushed with use of a meat chopper (manufactured by Iizuka Kogyo Co., Ltd., MEAT-CHOPPER TYPE: 12VR-400KSOX, die pore diameter: 6.4 mm, the number of pores: 38, die thickness: 8 mm) to obtain a hydrogel in the form of particles.

The hydrogel in the form of particles was spread out on a 50-mesh metal gauze (mesh size: 300 µm), dried with hot air at 180° C., and the dried material was pulverized with a roll mill. Furthermore, the resultant material was subjected to classification using JIS standard sieves having a mesh size of 710 µm and a mesh size of 150 µm. In this way, water-absorbing resin powder (a) which is a water-absorbing resin having a non-uniformly pulverized shape (solid content: 96 weight %) was obtained. Note that the water-absorbing resin powder (a) had a centrifuge retention capacity (CRC) of 47.4 g/g.

Production Example 2

431.2 g of acrylic acid, 1.158 g (0.034 mol % relative to carboxyl-group-containing unsaturated monomers) of polyethylene glycol diacrylate (molecular weight: 523) as an internal crosslinking agent, 2.64 g of 1.0 weight % aqueous trisodium diethylenetriamine pentaacetate (DTPA•3Na) solution, 177.65 g of 48.5 weight % aqueous sodium hydroxide solution, and 384.56 g of deionized water (ion-exchange water) were introduced into a 2-liter polypropylene container, and mixed to prepare an aqueous monomer solution (d1').

Next, the aqueous monomer solution (d1') was cooled with stirring. At a point in time at which the temperature of the aqueous monomer solution (d1') reached 39.5° C., 185.55 g of 48.5 weight % aqueous sodium hydroxide solution having the temperature adjusted to 40° C. was added and mixed to thereby prepare an aqueous monomer solution (d2). In so doing, the temperature of the aqueous monomer solution (d2) immediately after its preparation rose to 79.8° C. due to heat of neutralization at a second stage.

Next, 17.29 g of a 4.5 weight % aqueous sodium persulfate solution was added to the aqueous monomer solution (d2) while stirring was carried out. Immediately after that, the resulting solution was poured in an atmospheric air open system into a stainless steel vat-type vessel (with a bottom surface of 340 mm×340 mm and a height of 25 mm; inner surface: Teflon (registered trademark) coating). Pouring of the aqueous monomer solution (d2) into the vat-type vessel commenced 55 seconds after the start of the second-stage neutralization. The vat-type vessel was heated with use of a hot plate (NEO HOTPLATE HI-1000; Iuchi Seiei Do Ltd.) until surface temperature reached 40° C.

58 seconds after the aqueous monomer solution (d2) was poured into the vat-type vessel, a polymerization reaction started. In this polymerization reaction, a polymer that was generated gave off water vapor and swelled and foamed in various directions. The polymer then shrunk to a size slightly larger than the size of the vat-type vessel. 3 minutes after the start of the polymerization reaction, a hydrogel was taken out. Note that this series of operations was carried out in an atmospheric air open system.

The hydrogel obtained through the above polymerization reaction was subjected to gel-crushing with use of a meat chopper (HL-3225N; plate pore diameter: 10.0 mm; Remacom Co., Ltd.), to obtain a particulate hydrogel (2).

The hydrogel was introduced into the meat chopper at a rate of 230 g/min. The gel-crushing was carried out while deionized water having a temperature adjusted to 90° C. was being added at a rate of 50 g/min simultaneously with the introduction of the hydrogel.

The particulate hydrogel obtained through the above operation was spread on a stainless-steel metal gauze having a mesh size of 850 µm, and was dried by letting through 180° C. hot air for 30 minutes. Subsequently, a dried polymer (2) obtained through the drying treatment was pulverized with use of a roll mill (WML-type roll pulverizer; Inoguchi Giken Ltd.), and was then classified with use of JIS standard sieves having respective mesh sizes of 850 µm and 90 µm. This produced water-absorbing resin powder (b) which is a water-absorbing resin having a non-uniformly pulverized shape (solid content: 96 weight %). The water-absorbing resin powder (b) had a centrifuge retention capacity (CRC) of 42.1 g/g.

Production Example 3

421.3 g of acrylic acid, 1.040 g (0.034 mol % relative to carboxyl-group-containing unsaturated monomers) of polyethylene glycol diacrylate (molecular weight: 523) as an internal crosslinking agent, 2.58 g of a 1.0 weight % aqueous trisodium diethylenetriamine pentaacetate (DTPA•3Na) solution, 173.57 g of a 48.5 weight % aqueous sodium hydroxide solution, and 396.31 g of deionized water (ion-exchange water) were introduced into a 2-liter polypropylene container, and were mixed with one another to prepare an aqueous monomer solution (e1').

Next, the aqueous monomer solution (e1') was cooled with stirring. At a point in time at which the temperature of the aqueous monomer solution (e1') reached 39.8° C., 181.77 g of 48.5 weight % aqueous sodium hydroxide solution having the temperature adjusted to 40° C. was added and mixed to thereby prepare an aqueous monomer solution (e2). In so doing, the temperature of the aqueous monomer solution (e2) immediately after its preparation rose to 80.1° C. due to heat of neutralization at a second stage.

Next, 16.89 g of a 4.5 weight % aqueous sodium persulfate solution was added to the aqueous monomer solution (e2) while stirring was carried out. Immediately after that, the resulting solution was poured in an atmospheric air open system into a stainless steel vat-type vessel (with a bottom surface of 340 mm×340 mm and a height of 25 mm; inner surface: Teflon (registered trademark) coating). Pouring of the aqueous monomer solution (e2) into the vat-type vessel commenced 55 seconds after the start of the second-stage neutralization. The vat-type vessel was heated with use of a hot plate (NEO HOTPLATE HI-1000; Iuchi Seiei Do Ltd.) until surface temperature reached 40° C.

56 seconds after the aqueous monomer solution (e2) was poured into the vat-type vessel, a polymerization reaction started.

The rest of the operations were the same as those of Production Example 2. In this way, a dried polymer (3) was obtained.

The dried polymer (3) was pulverized with use of a roll mill (WML-type roll pulverizer; Inoguchi Giken Ltd.), and was then classified with use of JIS standard sieves having respective mesh sizes of 710 µm and 90 µm. This produced water-absorbing resin powder (c) which is a water-absorbing resin having a non-uniformly pulverized shape (solid content: 95 weight %). The water-absorbing resin powder (c) had a centrifuge retention capacity (CRC) of 44.3 g/g.

Production Example 4

Into a reactor formed by attaching a lid to a stainless steel twin-arm kneader (capacity: 10 L) having two sigma-type blades and a jacket, 374.3 g of acrylic acid, 3961.3 g of a 37 weight % aqueous sodium hydroxide solution, 637.3 g of deionized water, and 4.25 g (0.042 mol % relative to carboxyl-group-containing unsaturated monomers) of polyethylene glycol diacrylate (molecular weight: 523) were dissolved to obtain an aqueous monomer solution (f1). Next, the aqueous monomer solution (f1) was degassed in a nitrogen atmosphere for 20 minutes. Next, while the aqueous monomer solution (f1) was stirred, 12.47 g of a 10 weight % aqueous sodium persulfate solution and 10.39 g of a 0.1 weight % aqueous L-ascorbic acid solution were added thereto. Polymerization commenced approximately 1 minute thereafter. Polymerization was carried out at 20° C. to 95° C. while crushing a gel that was created. 30 minutes after polymerization started, a hydrogel was taken out. The hydrogel obtained thusly had been grain refined such that its particles were not more than approximately 5 mm in size. The grain-refined hydrogel was spread out on a metal gauze (50 mesh) and dried with hot air at 180° C. for 50 minutes. A resulting dried material was pulverized with use of a roll mill and then classified with use of a JIS standard sieve having a mesh size of 710 μm and a JIS standard sieve having a mesh size of 150 μm. In this way, water-absorbing resin powder (d) which is a water-absorbing resin having a non-uniformly pulverized shape (solid content: 95 weight %) was obtained. The water-absorbing resin powder (d) had a centrifuge retention capacity (CRC) of 40.5 g/g.

Production Example 5

The same operations as described in Production Example 2 were carried out, except that the classification was carried out with use of JIS standard sieves having a mesh size of 600 μm and a mesh size of 150 μm instead of the JIS standard sieves having a mesh size of 850 μm and a mesh size of 45 μm. In this way, water-absorbing resin powder (e) which is a water-absorbing resin having a non-uniformly pulverized shape (solid content: 96 weight %) was obtained. The water-absorbing resin powder (e) had a centrifuge retention capacity (CRC) of 42.4 g/g.

Production Example 6

The following aqueous monomer solution was prepared: an aqueous monomer solution containing 300 parts by weight of acrylic acid, 100 parts by weight of a 48 weight % aqueous sodium hydroxide solution, 0.94 parts by weight of polyethylene glycol diacrylate (average n number: 9), 16.4 parts by weight of a 0.1 weight % aqueous trisodium diethylenetriamine pentaacetate solution, and 314.3 parts by weight of deionized water.

Next, the aqueous monomer solution whose temperature had been adjusted to 38° C. was continuously supplied by a metering pump, and then 150.6 parts by weight of a 48 weight % aqueous sodium hydroxide solution was further continuously line-mixed with the aqueous monomer solution.

At this stage, the temperature of the aqueous monomer solution rose to 80° C. due to heat of neutralization.

Furthermore, 14.6 parts by weight of a 4 weight % aqueous sodium persulfate solution was continuously line-mixed with the aqueous monomer solution, and then a resultant mixture was continuously supplied into a continuous polymerization device, having a planar polymerization belt with dams at both ends, so that the supplied mixture had a thickness of 10 mm. Thereafter, polymerization (polymerization time: 3 minutes) was continuously carried out, so that a belt-shaped hydrogel was obtained. The belt-shaped hydrogel obtained was continuously cut at regular intervals in the width direction relative to the traveling direction of the polymerization belt so that the cut length was 300 mm. Thus, a hydrogel was obtained. The hydrogel had a CRC of 33.5 g/g and a solid content of 49.5 weight %.

The obtained hydrogel was supplied to a screw extruder and subjected to gel-crushing.

As the screw extruder, a meat chopper including a porous plate and a screw shaft was used. The porous plate was provided at a tip of the meat chopper and had a diameter of 100 mm, a pore diameter of 9.5 mm, 40 pores, an open ratio of 36.1%, and a thickness of 10 mm, and the screw shaft had an outer diameter of 86 mm. While the screw shaft of the meat chopper was being rotated at 130 rpm, the hydrogel was supplied at 4640 (g/min), and at the same time, water vapor was supplied at 83 (g/min). In this case, gel-grinding energy (GGE) was 26.9 (J/g), and GGE (2) was 13.6 (J/g). The hydrogel which had not been subjected to the gel-crushing had a temperature of 80° C., and the temperature rose to 85° C. in a crushed gel obtained after the gel-crushing, i.e., a particulate hydrogel.

The particulate hydrogel obtained through the above gel-crushing step had a resin solid content of 49.1 weight %, a weight average particle diameter (D50) of 994 μm, and a logarithmic standard deviation (σζ) of a particle size distribution of 1.01.

Next, the particulate hydrogel was dispersed onto a through-flow plate within 1 minute of the end of the gel-crushing (at this stage, the particulate hydrogel had a temperature of 80° C.), and dried at 185° C. for 30 minutes, so that a dried polymer was obtained. Hot air had an average air velocity of 1.0 (m/s) in the direction perpendicular to the traveling direction of the through-flow belt. The air velocity of the hot air was measured with use of Anemomaster 6162, which is a constant temperature thermal anemometer manufactured by Kanomax Japan Inc.

Subsequently, the dried polymer obtained through the above drying step, in its entirety, was supplied to a three-stage roll mill and pulverized (subjected to a pulverizing step). Thereafter, the dried polymer thus pulverized was further classified with use of JIS standard sieves having respective mesh sizes of 710 μm and 175 μm. Thus, water-absorbing resin powder (f) which is a water-absorbing resin (solid content: 94 weight %) was obtained. The water-absorbing resin powder (f) had a weight average particle diameter (D50) of 348 μm, a logarithmic standard deviation (σζ) of a particle size distribution of 0.32, a CRC of 42.1 g/g, and a proportion of 150 μm passing particles (a proportion of particles passing through a sieve having a mesh size of 150 μm) of 0.5 weight %.

Example 1

The water-absorbing resin powder (a) obtained in Production Example 1 was transferred to a rotary mixer manufactured by Gebrueder Loedige Maschinenbau Gmbh, and an aqueous surface-crosslinking agent solution containing 0.03 parts by weight of ethylene glycol diglycidyl ether (product name: DENACOL EX-810, manufactured by Nagase ChemteX Corporation), 1.0 part by weight of propylene glycol, and 3.0 parts by weight of water was mixed with 100 parts by weight of the water-absorbing resin powder (a) uniformly. Then, the resultant mixture was subjected to a heating treatment at 100° C. for 45 minutes. Then, the resultant mixture was passed through a JIS standard sieve having a mesh size of 850 μm to obtain surface-crosslinked water-absorbing resin particles (1).

To 100 parts by weight of the surface-crosslinked water-absorbing resin particles (1), 0.3 parts by weight of hydrotalcite (product name: DHT-6, manufactured by Kyowa Chemical Industry Co., Ltd., $Mg_6Al_2(OH)_{16}CO_3 \cdot 4H_2O$ [represented by General Formula (1) where x=0.25 and m=0.50], volume average particle diameter: 0.5 μm) was mixed. The mixing was carried out in the following manner: 30 g of the water-absorbing resin was put in a 225-milliliter mayonnaise bottle together with hydrotalcite and then mixed by shaking (at room temperature for 3 minutes) with use of a paint shaker (manufactured by Toyo Seiki Seisaku-sho, Ltd.). In this way, a particulate water-absorbing agent (1) was obtained. Physical properties of the particulate water-absorbing agent (1) are shown in Tables 7 and 8.

The obtained particulate water-absorbing agent (1) was fed and conveyed in accordance with "(A) Method of feeding using bulk solid pump (BSP)" in the following <Measurement method> section.

Example 2

The water-absorbing resin powder (b) obtained in Production Example 2 was transferred to a rotary mixer manufactured by Gebrueder Loedige Maschinenbau Gmbh, and an aqueous surface-crosslinking agent solution containing 0.385 parts by weight of ethylene carbonate, 0.644 parts by weight of propylene glycol, and 2.6 parts by weight of deionized water was mixed with 100 parts by weight of the water-absorbing resin powder (b) uniformly. Then, the resultant mixture was subjected to a heating treatment in a paddle mixer preheated to 200° C. An average time (retention time) that the mixture was retained in the paddle mixer was approximately 50 minutes. The heated material was cooled and subjected to classification with use of JIS standard sieves having respective mesh sizes of 850 μm and 150 μm, so that surface-crosslinked water-absorbing resin particles (2) were obtained.

Next, 1.0 part by weight of deionized water and 0.01 parts by weight of trisodium diethylenetriamine pentaacetate (called "DTPA•3Na" for short, CHELEST PC-45, manufactured by CHELEST CORPORATION) were mixed with 100 parts by weight of the surface-crosslinked water-absorbing resin particles (2) uniformly. After that, the resultant mixture was subjected to a heating treatment under a windless condition at 60° C. for 45 minutes, and then passed through a JIS standard sieve having a mesh size of 850 μm to obtain a particulate water-absorbing agent (2). Physical properties of the particulate water-absorbing agent (2) are shown in Tables 7 and 8.

The obtained particulate water-absorbing agent (2) was fed and conveyed in accordance with "(A) Method of feeding using bulk solid pump (BSP)" in the following <Measurement method> section.

Example 3

To 100 parts by weight of the particulate water-absorbing agent (2) obtained in Example 2, 0.3 parts by weight of zinc stearate (manufactured by KANTO CHEMICAL CO., INC.) was further mixed uniformly to obtain a particulate water-absorbing agent (3). Physical properties of the particulate water-absorbing agent (3) are shown in Tables 7 and 8.

The obtained particulate water-absorbing agent (3) was fed and conveyed in accordance with "(A) Method of feeding using bulk solid pump (BSP)" in the following <Measurement method> section.

Example 4

The same operations as described in Example 2 were carried out, except that the water-absorbing resin powder (d) obtained in Production Example 4 was used instead of the water-absorbing resin powder (b) and that a JIS standard sieve having a mesh size of 710 μm was used instead of the JIS standard sieve having a mesh size of 850 μm. In this way, surface-crosslinked water-absorbing resin particles (4) were obtained.

Next, 0.001 parts by weight of 10 weight % polyoxyethylene (20) sorbitan monostearate (product name: RHEODOL TW-S120V; manufactured by Kao Corporation), 0.01 parts by weight of trisodium diethylenetriamine pentaacetate (DTPA•3Na), and 1.0 part by weight of deionized water were uniformly mixed to 100 parts by weight of the surface-crosslinked water-absorbing resin particles (4). Then, the mixture was subjected to a heating treatment under a windless condition at 60° C. for 45 minutes, and then crushed to a size that can pass through a JIS standard sieve having a mesh size of 850 μm. In this way, a particulate water-absorbing agent (4) was obtained. Physical properties of the particulate water-absorbing agent (4) are shown in Tables 7 and 8.

The obtained particulate water-absorbing agent (4) was fed and conveyed in accordance with "(A) Method of feeding using bulk solid pump (BSP)" in the following <Measurement method> section.

Example 5

To 100 parts by weight of the water-absorbing resin powder (f) obtained in Production Example 6, the following aqueous surface-crosslinking agent solution was mixed uniformly: an aqueous (covalent) surface-crosslinking agent solution containing 0.025 parts by weight of ethylene glycol diglycidyl ether, 0.4 parts by weight of 1,4-butanediol, 0.6 parts by weight of propylene glycol, and 3.0 parts by weight of deionized water. The resultant mixture was subjected to a heating treatment at 190° C. for about 30 minutes in a paddle mixer so that the resulting water-absorbing resin powder (1) would have a CRC of 33 g/g. In this way, surface-crosslinked water-absorbing resin particles (5) were obtained. Then, the surface-crosslinked water-absorbing resin particles (5) were cooled, and, to 100 parts by weight of the surface-crosslinked water-absorbing resin particles (5), an aqueous solution containing 1 part by weight of water and 0.01 parts by weight of trisodium diethylenetriamine pentaacetate was mixed uniformly. The resultant mixture was dried at 60° C. for 1 hour, and then passed through a JIS standard sieve having a mesh size of 710 μm. In this way, a particulate water-absorbing agent (5) was obtained. Physical properties of the particulate water-absorbing agent (5) are shown in Tables 7 and 8.

The obtained particulate water-absorbing agent (5) was fed and conveyed in accordance with "(A) Method of

Example 6

To the particulate water-absorbing agent (5) obtained in Example 5, 0.3 parts by weight of silicon dioxide (product name: Aerosil 200, manufactured by Nippon Aerosil Co., Ltd.) was mixed uniformly to thereby obtain a particulate water-absorbing agent (6). Physical properties of the particulate water-absorbing agent (6) are shown in Tables 7 and 8.

The obtained particulate water-absorbing agent (6) was fed and conveyed in accordance with "(A) Method of feeding using bulk solid pump (BSP)" in the following <Measurement method> section.

Comparative Example 1

The following mixed solution was prepared: a mixed solution (1) containing 0.53 parts by weight of 27 weight % aqueous aluminum sulfate solution (8 weight % based on aluminum oxide) as a polyvalent metal cation, 0.16 parts by weight of 60 weight % aqueous sodium lactate solution, and 0.01 parts by weight of propylene glycol.

To 100 parts by weight of the particulate water-absorbing agent (2) obtained in Example 2, 0.7 parts by weight of the mixed solution (1) was added with stirring and mixed uniformly for 1 minute. Then, the mixture was dried under a windless condition at 60° C. for 30 minutes, and then passed through a JIS standard sieve having a mesh size of 850 μm. In this way, a comparative particulate water-absorbing agent (1) was obtained. Physical properties of the comparative particulate water-absorbing agent (1) are shown in Tables 7 and 8.

The obtained comparative particulate water-absorbing agent (1) was fed and conveyed in accordance with "(A) Method of feeding using bulk solid pump (BSP)" in the following <Measurement method> section.

Comparative Example 2

The water-absorbing resin powder (c) obtained in Production Example 3 was transferred to a rotary mixer manufactured by Gebrueder Loedige Maschinenbau Gmbh, and an aqueous surface-crosslinking agent solution containing 0.02 parts by weight of ethylene glycol diglycidyl ether (product name: DENACOL EX-810, manufactured by Nagase ChemteX Corporation), 0.3 parts by weight of ethylene carbonate, 0.5 parts by weight of propylene glycol, and 2.0 parts by weight of deionized water was mixed with 100 parts by weight of the water-absorbing resin powder (c) uniformly. Then, the mixture was subjected to a heating treatment in a paddle mixer preheated to 180° C. An average time (retention time) that the mixture was retained in the paddle mixer was approximately 50 minutes. The heated material was cooled and passed through a JIS standard sieve having a mesh size of 850 μm, so that comparative surface-crosslinked water-absorbing resin particles (1) were obtained.

Next, to 100 parts by weight of the comparative surface-crosslinked water-absorbing resin particles (1), 0.3 parts by weight of hydrophilic silicon dioxide (product name: Aerosil 200, manufactured by Nippon Aerosil Co., Ltd.) was mixed. The mixing was carried out in the same manner as the mixing of hydrotalcite in Example 1, and thereby a comparative particulate water-absorbing agent (2) was obtained. Physical properties of the comparative particulate water-absorbing agent (2) are shown in Tables 7 and 8.

The obtained comparative particulate water-absorbing agent (2) was fed and conveyed in accordance with "(A) Method of feeding using bulk solid pump (BSP)" in the following <Measurement method> section.

Comparative Example 3

The same operations as described in Example 2 were carried out, except that the water-absorbing resin powder (e) obtained in Production Example 5 was used instead of the water-absorbing resin powder (b). In this way, a comparative particulate water-absorbing agent (3') was obtained.

Next, to 100 parts by weight of the comparative particulate water-absorbing agent (3'), 0.7 parts by weight of the mixed solution (1) produced in Comparative Example 1 was added with stirring and mixed uniformly for 1 minute. Then, the mixture was dried under a windless condition at 60° C. for 30 minutes, and then passed through a JIS standard sieve having a mesh size of 850 μm. In this way, a comparative particulate water-absorbing agent (3) was obtained. Physical properties of the comparative particulate water-absorbing agent (3) are shown in Tables 7 and 8.

The obtained comparative particulate water-absorbing agent (3) was fed and conveyed in accordance with "(A) Method of feeding using bulk solid pump (BSP)" in the following <Measurement method> section.

<Measurement Method>

(A) Method of Feeding Using Bulk Solid Pump (BSP)

The feeding method was carried out with use of a bulk solid pump (model: K-ML-BSP-125) manufactured by Coperion K-tron. The weight of fed powder for use in calculation of feed rate was measured with use of a balance scale which is disposed below an outlet of the feeder and which is capable of measurement with an accuracy of 0.1 g (e.g., model GP-30K manufactured by A&D Company, Limited). Note that the temperature of an environment in which the feeding was carried out was 23.5° C. and the relative humidity of the environment was 38% RH.

20.0 kg of a water-absorbing agent was introduced into a hopper at the upper portion of the feeder, the mode of the feeder was set to gravimetric mode and the flow rate was set to 100 kg/hr., and the feeder was operated for 10 minutes. The gravimetric mode is such that the feed rate during operation is automatically measured by a scale that is included with the feeder, the measured feed rate is fed back to the feeder, the rotation speed of disks is automatically adjusted, and thereby a deviation from the set feed rate is automatically corrected. From the start of the operation of the feeder to the end of the operation of the feeder, the weight indicated by the balance scale (total weight (g) of discharged powder) was read and recorded every 10 seconds.

Among the total weights (g) of discharged powder recorded every 10 seconds, those obtained within a period from 1 minute after the start of the operation to 9 minutes after the start of the operation were used in calculation. First, based on the difference between two adjacent ones of the total weights (g) of discharged powder recorded every 10 seconds, the amount of increase in weight of powder per 10 seconds (i.e., weight increment) (g/10 sec.) was calculated. Next, each weight increment (g/10 sec.) of powder obtained through the above calculation was multiplied by 6 to obtain a feed amount per unit time (i.e., feed rate) (g/min.). Furthermore, the standard deviation (σ) of the feed amount per unit time (g/min.) was calculated.

The values of the standard deviation (σ) of the particulate water-absorbing agents of the present invention and the comparative particulate water-absorbing agents are shown in Table 8. Table 8 also shows the proportion of the standard deviation (σ) to average flow rate ((σ/average flow rate)×100, where the average flow rate is 100 kg/hr.=1667 g/min.). A smaller value of the standard deviation (σ), and a smaller proportion of the standard deviation (σ) to the average flow rate, mean that the fluctuation of the feed amount per unit time is small and that the powder is supplied more stably.

(B) Method of Measuring Parameters of Powder Properties

With use of a powder tester (model: PT-X) manufactured by HOSOKAWA MICRON CORPORATION, parameters (e.g., angle of repose, angle of fall, loose bulk density, tight bulk density, angle of spatula) of powder properties of each water-absorbing agent were measured. Note that the temperature in an environment in which the measurements were carried out was 23.5° C., and the relative humidity in the environment was 38% RH.

(1. Angle of Repose)

90 g of a well-mixed water-absorbing agent was weighed out in a 250-milliliter polypropylene container. A vat-fixing unit, a vat, an angle-of-repose-measuring table (product number: XS-24), and an angle-of-repose-measuring funnel 5 mm in diameter (product number: XS-26), which are included with the powder tester, were attached to the body of the powder tester, and the sample was poured into the tester from the top of the funnel. The sample was allowed to fall while the funnel was shaken with an amplitude of 1.5 mm to form an angle of repose. After all the sample had fallen, the shaking was stopped, and the angle of repose was measured.

(2. Angle of Fall)

After the angle of repose was measured as above, a shock was applied once to the table with use of an automatic shocker, and thereby an angle of fall was formed and measured.

(3. Angle of Difference)

The angle of difference was calculated in accordance with the following equation.

Angle of difference (degree)=Angle of repose−Angle of fall (4. Angle of Spatula)

A vat fixing unit, a vat, and an angle-of-spatula-measuring unit (product number: XS-29), which are included with the powder tester, were attached to the body of the powder tester, and a spatula frame (product number: XS-30) was placed on the vat such that the spatula blade resides in the middle of the vat. A well-mixed water-absorbing agent was supplied using a scoop onto the spatula blade so that the spatula frame would be totally filled with the water-absorbing agent and a sufficient heap would form. The vat was lowered, and the angle between the slope of the heap and the horizontal plane (before shock application) was measured. Next, a shock was applied once to the spatula blade with use of an automatic shocker, and the angle between the slope of the heap and the horizontal plane (after shock application) was measured. The average of these angles (angle before the shock application and angle after the shock application) was used as the angle of spatula.

(5. Loose Bulk Density)

A vat, a tapping lift bar, a stationary chute, a chute bracket, a chute for 25 cc, and a 25 cc bulk density measuring cup whose weight had been accurately measured to 0.01 g, which are included with the powder tester, were attached to the body of the powder tester. 50 g of a well-mixed water-absorbing agent was weighed out in a 250-milliliter polypropylene container, the tapping lift bar was raised, and then the sample was poured from the top of the chute until the sample overflowed from the measuring cup so that the sample would completely fill the measuring cup. The water-absorbing agent on the top of the measuring cup was leveled off with a metal blade that is included with the powder tester, the weight of the measuring cup containing the water-absorbing agent therein was accurately measured to 0.01 g, and loose bulk density was calculated. The loose bulk density is calculated using the following equation.

Loose bulk density (g/ml)=(Weight of cup containing water-absorbing agent therein−Weight of empty cup)/25

(6. Tight Bulk Density)

After the measurement of the loose bulk density, a cap which is included with the powder tester and which has the same inner diameter as the cup was attached to the cup, and the cup was attached to the powder tester. 50 g of a well-mixed water-absorbing agent was weighed out in a 250-milliliter polypropylene container, and the sample was poured from the top of the chute until the sample overflowed from the measuring cup so that the sample would completely fill the measuring cup. The number of taps was set to 180, and tapping was started. The length of stroke of each tap was fixed at 18 mm. After finishing tapping, the cap was removed, the water-absorbing agent on the top of the measuring cup was leveled off with the metal blade coming with the powder tester, the weight of the measuring cup containing the water-absorbing agent therein was measured accurately to 0.01 g, and tight bulk density was calculated. The tight bulk density is calculated using the following equation.

Tight bulk density (g/ml)=(Weight of cup containing water-absorbing agent therein after tapping−Weight of empty cup/25

(7. Compressibility Rate)

The compressibility rate was calculated in accordance with the following equation.

Compressibility rate (%)=(Tight bulk density−Loose bulk density)/Tight bulk density×100

(8. Degree of Uniformity)

The degree of uniformity is calculated in the following manner. Particle size distributions (60% undersize particle diameter (D60) and 10% undersize particle diameter (D10)) were measured using standard sieves in accordance with a measurement method disclosed in U.S. Pat. No. 7,638,570 or EDANA ERT420.2-02. The degree of uniformity is calculated from the 60% undersize particle diameter (D60) and 10% undersize particle diameter (D10) using the following equation.

Degree of uniformity=D60/D10

(9. Carr's Flowability Index)

A Carr's flowability index can be found in the following manner. The measured values of the foregoing powder properties are converted into indices proposed by Carr, and the Carr's flowability index can be found from the total sum of those values (angle of repose index+compressibility rate index+angle of spatula index+degree of uniformity index).

The Carr's indices were found with reference to the operation manual for the powder tester PT-X (HOSOKAWA MICRON CORPORATION) (reprint from Carr, R.L. Evaluating Flow Properties of Solids. Chem. Eng. 1965, 72, 163-168).

Each of the water-absorbing agents studied here had a degree of uniformity of 2 to 4, and degree of uniformity index was 23.

A study was carried out on optimization of the foregoing parameters, and it was found that the following is most appropriate:

K-index=100−(−438+3.6×angle of repose+3.5×angle of difference+7.9×compressibility rate+290× bulk density (EDANA method)).

The values of parameters and K-index of the particulate water-absorbing agents of the present invention and the comparative particulate water-absorbing agents are shown in Table 8. It was found that a water-absorbing agent satisfying K-index≥70 is excellent in stability of feeding using a feeder for use in the present invention (fluctuation of feed amount per unit time is small).

(C) Probe Insertion Test

[Measurement of Probe Insertion Work (PIW) and Probe Insertion Distance (PID)]

<Sample for Measurement (Measurement Sample)>

27 g to 30 g of a water-absorbing agent or water-absorbing resin was placed in a cylinder-type sample tube made of glass (outer diameter: 35 mm, inner diameter: 33 mm, height: 78 mm, e.g., Screw Vial No. 7 manufactured by Maruemu corporation), and shaken well. Then, the sample tube was tapped vertically (three times/second, amplitude: 10 mm) for 1 minute on an iron sheet, and thereby the water-absorbing agent or water-absorbing resin was brought into a condition in which the water-absorbing agent or water-absorbing resin is closely packed within the sample tube. Next, the amount of the water-absorbing agent or water-absorbing resin was adjusted by increasing or decreasing the amount as needed so that the water-absorbing agent or water-absorbing resin filled and closely packed in the sample tube (this water-absorbing agent or water-absorbing resin is hereinafter referred to as "particle bed") would have a height of 45±1.5 mm. In a case where the amount of the water-absorbing agent or water-absorbing resin was adjusted as described above, the sample tube was well shaken again and then, on the iron sheet, tapped vertically (three times/ second, amplitude: 10 mm) for 1 minute and thereby the water-absorbing agent or water-absorbing resin was brought into a condition in which it is closely filled. Note that the tapping was carried out so that the top surface of the particle bed after the tapping would be flat and horizontal.

In measurement of the PIW and PID, the average of three measured values is employed. Therefore, every time a measurement was completed, the sample tube having the particle bed formed therein was capped and shaken well, tapped vertically for 1 minute on the iron plate again in the foregoing manner, and thereby a sample for measurement in a state in which the top surface of the particle bed is flat and horizontal was obtained.

<Measurement Apparatus>

The PIW and PID were measured with use of a measurement apparatus illustrated in FIG. 5. The measurement apparatus (KES-G5 Handy Compression Tester, manufactured by KATO TECH CO., LTD., Head office: Minami-ku, Kyoto-shi, Japan) includes: a compression device 11; a control device 12 that controls the compression device 11; and a computer 13 that loads data obtained from the compression device 11 and the control device 12. The compression device 11, the control device 12, and the computer 13 are connected together by cables.

The compression device 11 includes, as illustrated in FIG. 6, a movable stage 3, an insertion probe (insertion member) 4, a movable load cell (force gage) 5, and a displaced distance detector 6.

The stage 3 is a stage on which a measurement sample 2 filled with a water-absorbing agent or water-absorbing resin (hereinafter "particle bed") 1 is to be placed, and is moveable relative to the insertion probe 4. The insertion probe 4 is a metal rod inserted into a particle bed 1 composed of a water-absorbing agent or water-absorbing resin of the measurement sample 2. In the present example, the insertion probe 4 is a positive electrode made of aluminum oxide having a diameter of 12.7 mm and a length of 40 mm with a spherically made end (round end) having a radius of 5 mm (see FIG. 7). Note that, with regard to a surface roughness of the insertion probe 4 standardized in accordance with JIS B0601-1994, usually, the maximum height is 0 μm to 10 μm, preferably 0 μm to 1 μm, ten-point average roughness is 0 μm to 10 μm, preferably 0 μm to 1 μm, and center line average roughness is 0 μm to 5 μm, preferably 0 μm to 1 μm. The insertion probe 4 is attached to (screwed to) the load cell 5 (FIG. 6) as is apparent from FIG. 7, and is movable together with the load cell 5.

The load cell 5 applies, to the particle bed 1 of the measurement sample 2 via the insertion probe 4, a load that varies in magnitude with an upper limit of 10 kg. The load cell 5 is joined to the displaced distance detector 6 as illustrated in FIG. 6, and is movable relative to the measurement sample 2. The displaced distance detector 6 detects the distance traveled by the load cell 5, i.e., displaced distance.

The control device 12 illustrated in FIG. 5 includes: an insertion speed regulator that regulates the speed of insertion of the insertion probe 4; a load regulator that regulates a load applied from the insertion probe 4 to the particle bed of the measurement sample 2; a displaced distance regulator that regulates the displaced distance of the load cell 5; a displaced distance indicator that indicates the displaced distance of the load cell 5; a load indicator that indicates a load applied to the particle bed of the measurement sample 2; and an integrator.

The computer 13 illustrated in FIG. 5 loads data obtained from the compression device 11 and the control device 12 as digital data. The computer 13 has recorded therein the displaced distance of the insertion probe 4 (i.e., load cell 5) that makes contact with the top surface of the particle bed 1 of the measurement sample 2, the load applied to the particle bed 1, and the like.

<Conditions Under which Measurement is Carried Out, and Measurement Method>

The measurement apparatus was placed on a horizontal, vibration-free testing bench, and the measurement of PIW and PID was carried out in the following manner in an environment in which the temperature and relative humidity had been adjusted to 25±1° C. and relative humidity 50±5%, respectively.

Specifically, the measurement sample 2 was prepared in the foregoing manner, and was placed on the stage 3 of the compression device 11 (FIG. 5) of the measurement apparatus while avoiding vibrations as much as possible. Next, the stage 3 was raised to a position at which the tip of the insertion probe 4 illustrated in FIG. 6 touches the top surface of the particle bed 1 of the measurement sample 2, and fixed. This position was used as a starting point (0 mm).

Then, the tip of the insertion probe 4 was allowed to enter the particle bed 1 at an insertion speed of 1 mm/second. Concurrently with the start of the entry of the insertion probe 4, a measurement was started at a data load interval of 0.1 seconds, and the distance the insertion probe 4 was inserted and the load required for the insertion probe 4 to insert were measured. Note that the distance the insertion probe 4 was inserted was within the range of from the starting point (0 mm) to 20 mm (error of the distance was within ±3%).

Furthermore, as shown in FIG. 8, a chart was created with the above-measured distance inserted (mm) on the horizontal axis and the measured load (gram force, or gf) on the vertical axis. The area between a curve connecting the obtained loads and the horizontal axis (this area is hatched in FIG. 8) was integrated within the range of from the distance 0 mm to 20 mm to obtain a probe insertion work (PIW), which is a work done when the insertion probe 4 is inserted by a distance of 0 mm to 20 mm.

The above measurement operation was carried out three times, the average of the obtained three values was used as a measured value. A water-absorbing agent of the particle bed 1, having a smaller PIW (determined in the above manner), can be considered more slidable as particles and better in handleability.

Note that the upper limit of the load was 10 kgf. In a case where the load reached 10 kgf before the distance the insertion probe 4 was inserted reached 20 mm, the PIW (gf×mm) and PID (mm) up to that point in time were calculated. The probe insertion works (PIW) and probe insertion distances (PID) are shown in Table 8.

TABLE 7

|  |  | Weight average particle diameter (D50) [μm] |
|---|---|---|
| Ex. 1 | P.W.A. agent (1) | 348 |
| Ex. 2 | P.W.A. agent (2) | 437 |
| Ex. 3 | P.W.A. agent (3) | 436 |
| Ex. 4 | P.W.A. agent (4) | 345 |
| Ex. 5 | P.W.A. agent (5) | 351 |
| Ex. 6 | P.W.A. agent (6) | 356 |
| Com. Ex. 1 | Com. P.W.A. agent (1) | 455 |
| Com. Ex. 2 | Com. P.W.A. agent (2) | 388 |
| Com. Ex. 3 | Com. P.W.A. agent (3) | 355 |

Note:
"Ex." stands for "Example", "Com. Ex." stands for "Comparative Example", "P.W.A. agent" stands for "particulate water-absorbing agent", "Com. P.W.A. agent" stands for "comparative particulate water-absorbing agent".

with "(e) Moisture content" of the foregoing [Measurement of physical properties of particulate water-absorbing agent or water-absorbing resin] section.

<Data Summary>

The "(σ/average flow rate)×100" was plotted against K-index and Carr's flowability index to obtain charts, with regard to the particulate water-absorbing agents of the present invention and the comparative particulate water-absorbing agents (see FIGS. 9 and 19, respectively). Furthermore, the logarithmic standard deviation σ was plotted against the PIW and Carr's flowability index to obtain charts (see FIGS. 11 and 12, respectively). It was found from the charts shown in FIGS. 9 to 12 that the logarithmic standard deviation σ, which indicates a fluctuation of flow amount per unit time at a BSP, has no correlation with the Carr's flowability index but has correlations with the K-index and PIW, and that, especially when K-index≥70 and PIW≤30000 gf×mm are satisfied, the logarithmic standard deviation σ has correlations with the K-index and PIW.

In the above descriptions, preferred embodiments of the present invention were used as illustrative examples of the present invention. It is to be understood, however, that the scope of the present invention shall be construed only from the scope of the claims. Furthermore, it is to be understood that patents, patent applications, and other literatures cited in the present specification are incorporated herein by reference as if specifically set forth herein.

INDUSTRIAL APPLICABILITY

According to the present invention, it is possible to provide a water-absorbing agent that causes no or little fluctuation of feed rate when fed with use of a feeder. Furthermore, according to the present invention, it is possible to provide a method for producing an absorbent article with use of a water-absorbing agent containing a water-absorbing resin (SAP) as a main component, the method including a method of continuously feeding, with use of a feeder, a water-absorbing agent containing a water-absorbing resin (SAP) as a main component. The present invention can be used in various fields, e.g., in the fields of hygienic materials such as disposable diapers and sanitary napkins, and also in the fields of sheets for pets and waterproofing material.

TABLE 8

| Example No. | Measured σ g/min. | σ/average flow rate × 100 [%] | Angle of repose [°] | Angle of difference [°] | Compressibility rate [%] | Bulk density (Edana) [g/mL] | K-Index | PIW [gf × mm] | PID [mm] | Moisture content [weight %] |
|---|---|---|---|---|---|---|---|---|---|---|
| Ex. 1 | 12.5 | 0.75 | 35.3 | 8.3 | 12.8 | 0.68 | 83.9 | 7274 | 20 | 9.2 |
| Ex. 2 | 25.4 | 1.52 | 37.1 | 10.4 | 13.3 | 0.65 | 74.7 | 19419 | 20 | 3.3 |
| Ex. 3 | 6.6 | 0.40 | 35.7 | 8.9 | 11.8 | 0.69 | 85.7 | 1503 | 20 | 3.0 |
| Ex. 4 | 26.5 | 1.59 | 30.9 | 13.3 | 10.2 | 0.77 | 75.7 | 4717 | 20 | 3.1 |
| Ex. 5 | 16.8 | 1.01 | 35.5 | 9.6 | 14.5 | 0.63 | 80.0 | 12012 | 20 | 2.8 |
| Ex. 6 | 27 | 1.62 | 36.5 | 9.7 | 15.9 | 0.60 | 72.0 | 39092 | 13 | 2.5 |
| Com. Ex. 1 | 33 | 1.98 | 34.2 | 11.4 | 13.9 | 0.69 | 64.8 | 59855 | 20 | 2.9 |
| Com. Ex. 2 | 47.7 | 2.86 | 36.1 | 10.9 | 16.2 | 0.67 | 48.6 | 36686 | 13 | 1.8 |
| Com. Ex. 3 | 47.8 | 2.87 | 38.5 | 7.6 | 15.2 | 0.66 | 60.9 | 37494 | 20 | 3.1 |

Average flow rate: 100 kg/hr = 1667 g/min
Note:
"Ex." stands for "Example", "Com. Ex." stands for "Comparative Example"

With regard to the moisture content (weight %) of each water-absorbing agent in Table 8, the measurement and calculation concerning the moisture content (weight %) of each water-absorbing agent were carried out in accordance

REFERENCE SIGNS LIST 1 particle bed
2 measurement sample 3 stage
4 insertion probe (insertion member)
5 load cell (force gage)
6 displaced distance detector
11 compression device
12 control device
13 computer

The invention claimed is:

1. A water-absorbing agent comprising a water-absorbing resin as a main component and a polyvalent metal salt in an amount of 0.001 to 10 parts by weight relative to 100 parts by weight of the water-absorbing resin, wherein said water-absorbing agent satisfies the following (a) and (b):
   (a) K-index is 70 or more; and
   (b) Moisture absorption blocking ratio, after 30 minutes of standing at a temperature of 25° C. and a relative humidity of 80% RH, is 70 weight % or less,
   the K-index being defined by the following equation:
   K-index=100−(−438+3.6×angle of repose+3.5×angle of difference+7.9×compressibility rate+290×bulk density (EDANA method)).

2. The water-absorbing agent according to claim 1, wherein the moisture absorption blocking ratio is 40 weight % or less.

3. The water-absorbing agent according to claim 1, wherein the moisture absorption blocking ratio is 30 weight % or less.

4. The water-absorbing agent according to claim 1, wherein a powder flowability of said water-absorbing agent is 10.0 g/s or more.

5. The water-absorbing agent according to claim 1, wherein a powder flowability of said water-absorbing agent is 11.0 g/s or more.

6. The water-absorbing agent according to claim 1, wherein a surface tension of said water-absorbing agent is 65 mN/m or more.

7. The water-absorbing agent according to claim 1, wherein diffusing absorbency, which is measured 10 minutes after a start of absorption of 0.9 weight % aqueous sodium chloride solution by said water-absorbing agent under a load of 1.96 kPa, is 15 g/g or more.

8. The water-absorbing agent according to claim 1, wherein a probe insertion work of said water-absorbing agent is 30000 gf×mm or less.

9. The water-absorbing agent according to claim 1, wherein a moisture content of said water-absorbing agent is 10 weight % or less.

10. The water-absorbing agent according to claim 1, further comprising a surfactant.

11. The water-absorbing agent according to claim 1, further comprising a hydrophilic polymer compound.

12. The water-absorbing agent according to claim 1, wherein said water-absorbing agent is in the form of particles having a non-uniformly pulverized shape.

13. An absorbent article comprising a water-absorbing agent recited in claim 1.

* * * * *